(12) United States Patent
Golebiowski et al.

(10) Patent No.: US 9,440,953 B2
(45) Date of Patent: Sep. 13, 2016

(54) SUBSTITUTED AMINO TRIAZOLES USEFUL AS ACIDIC MAMMALIAN CHITINASE INHIBITORS

(71) Applicant: OncoArendi Therapeutics Sp z o.o., Warsaw (PL)

(72) Inventors: Adam Golebiowski, Madison, CT (US); Robert Koralewski, Łodź (PL); Wojciech J. Czestkowski, Pabianice (PL); Krzysztof Matyszewski, Lodz (PL); Sylwia Olejniczak, Łodź (PL); Jacek Olczak, Łodź (PL); Paul Beckett, Yorktown Heights, NY (US)

(73) Assignee: OncoArendi Therapeutics Sp. z o.o., Warsaw (PL)

( * ) Notice: Subject to any disclaimer, the term of this patent is extended or adjusted under 35 U.S.C. 154(b) by 0 days.

(21) Appl. No.: 14/959,369

(22) Filed: Dec. 4, 2015

(65) Prior Publication Data

US 2016/0176843 A1    Jun. 23, 2016

Related U.S. Application Data

(60) Provisional application No. 62/094,446, filed on Dec. 19, 2014.

(51) Int. Cl.
*C07D 401/04* (2006.01)
*A61K 31/4196* (2006.01)

(52) U.S. Cl.
CPC .................... *C07D 401/04* (2013.01)

(58) Field of Classification Search
None
See application file for complete search history.

(56) References Cited

U.S. PATENT DOCUMENTS 4,276,297 A * 6/1981 Lipinski ............... C07D 213/79
514/340

FOREIGN PATENT DOCUMENTS

WO    WO-2015/095701 A1    6/2015

* cited by examiner

*Primary Examiner* — Zinna Northington Davis
(74) *Attorney, Agent, or Firm* — Dana M. Gordon; Foley Hoag LLP

(57) ABSTRACT

Disclosed are amino triazole compounds substituted by a carboxylate functional group or an bioisosteric polar functional group. Compounds having the carboxylate moiety or carboxylate bioisostere inhibit acidic mammalian chitinase. Also provided are methods of using the compounds to treat asthma reactions caused by allergens.

33 Claims, No Drawings

SUBSTITUTED AMINO TRIAZOLES USEFUL AS ACIDIC MAMMALIAN CHITINASE INHIBITORS

RELATED APPLICATIONS

This application claims the benefit of priority to U.S. Provisional Patent Application Ser. No. 62/094,446, filed Dec. 19, 2014.

BACKGROUND OF THE INVENTION

Acidic mammalian chitinase (AMCase; $M_r$=~52.2 kD) is a secreted enzyme, typically found in the stomach, salivary gland, and lungs. The enzyme catalyzes the hydrolysis of artificial chitin-like substrates, and is unique among mammalian enzymes in that it has an acidic pH optimum. It is induced during Th2 inflammation through an IL-13-dependent mechanism. Chitinases are believed to play a key role in the innate immunity to parasites and other infectious agents. When produced in a dysregulated fashion, the enzymes may also play an important role in the pathogenesis of allergy and/or asthma.

Asthma is a chronic inflammatory disease of the airways characterized by recurrent episodes of reversible airway obstruction and airway hyperresponsiveness (AHR). Typical clinical manifestations include shortness of breath, wheezing, coughing and chest tightness that can become life threatening or fatal. While existing therapies focus on reducing the symptomatic bronchospasm and pulmonary inflammation, there is a growing awareness of the role of long-term airway remodeling in the accelerated lung deterioration in asthmatics. Airway remodeling refers to a number of pathological features, including epithelial smooth muscle and myofibroblast hyperplasia and/or metaplasia, subepithelial fibrosis and matric deposition.

It is generally accepted that allergic asthma is initiated by an inappropriate inflammatory reaction to airborne allergens. The lungs of asthmatics demonstrate an intense infiltration of lymphocytes, mast cells and, especially, eosinophils. AMCase is prominently expressed in lungs from antigen-sensitized and challenged and IL-13-transgenic mice. AMCase mRNA is not readily detected in lung tissues from patients without known lung disease, but has been detected, histologically and morphometrically, in the epithelial cells and subepithelial cells in tissues from patients with asthma.

Preliminary published studies (Zhu Z, Zheng T, Homer R J, Kim Y K, Chen N Y, Cohn L, Hamid Q, and Elias J A. Acidic mammalian chitinase in asthmatic Th2 inflammation and IL-13 pathway activation. Science 304: 1678-1682, 2004; Matsumoto T, et al. Demethylallosamidin, a chitinase inhibitor, suppresses airway inflammation and hyperresponsiveness. Biochem Biophys Res Commun 390: 103-108, 2009) suggest that AMCase plays a role in the Th-2 driven inflammatory response in a murine model of allergic asthma. Th-1 responses do not seem to be involved. No therapeutic effect was observed in a mouse model that expresses Th-1, but not Th-2 (Fitz L J, et al. Acidic mammalian chitinase is not a critical target for allergic airway disease. Am J Respir Cell Mol Biol 46: 71-9, 2011). This result would be expected since Th-1 cells are primarily involved in host defense against pathogens.

There is a need to investigate the inhibition of AMCase, and to discover treatments for conditions associated with elevated expression of AMCase, such as asthma and allergic responses. In particular, there is a need to explore new molecular scaffolds that effectively inhibit AMCase and, therefore, can act as therapeutic agents for the treatment of these conditions.

SUMMARY OF THE INVENTION

In one aspect, the invention provides a compound represented by formula (I), or a pharmaceutically acceptable salt thereof:

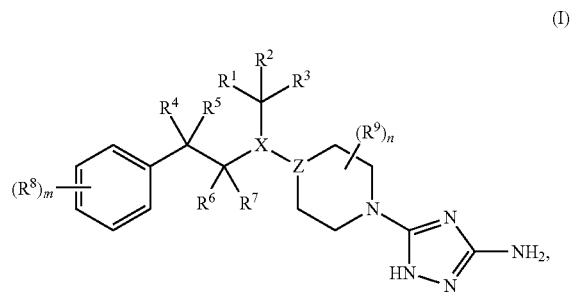

(I)

wherein:

X is N, and Z is $CR^{10}$; or X is $CR^{11}$, and Z is N;

$R^1$ is selected from the group consisting of Y, aryl substituted by Y, and ($C_1$-$C_6$)alkyl substituted by Y;

Y is —$CO_2H$, —C(O)O($C_1$-$C_6$)alkyl, —C(O)N(H)OH, —C(O)N(H)CN, —C(O)$NH_2$, —C(O)NH(($C_1$-$C_6$)alkyl), —C(O)N(($C_1$-$C_6$)alkyl)$_2$, —C(O)NH(aryl), —C(O)N(aryl)(($C_1$-$C_6$)alkyl), —C(O)N(aryl)$_2$, —C(O)NH(($C_1$-$C_6$)haloalkyl), —S(O)$_2$$NH_2$, —S(O)$_2$NH(($C_1$-$C_6$)alkyl), —S(O)$_2$NH(($C_1$-$C_6$)haloalkyl), —S(O)$_2$NH(aryl), —S(O)$_2$NHC(O)($C_1$-$C_6$)alkyl, —S(O)$_2$NHC(O)($C_1$-$C_6$)haloalkyl, —S(O)$_2$NHC(O)aryl, —N(H)S(O)$_2$($C_1$-$C_6$)alkyl, —N(H)S(O)$_2$aryl, N(H)S(O)$_2$($C_1$-$C_6$)haloalkyl, —NHC(O)(($C_1$-$C_6$)alkyl), —NHC(O)(($C_1$-$C_6$)haloalkyl), —NHC(O)(aryl), —NHC(O)NH($C_1$-$C_6$)alkyl, —NHC(O)NHaryl, —C(O)N(H)S(O)$_2$($C_1$-$C_6$)alkyl, —C(O)N(H)S(O)$_2$aryl, C(O)N(H)S(O)$_2$(($C_1$-$C_6$)haloalkyl), —P(O)(OH)$_2$,

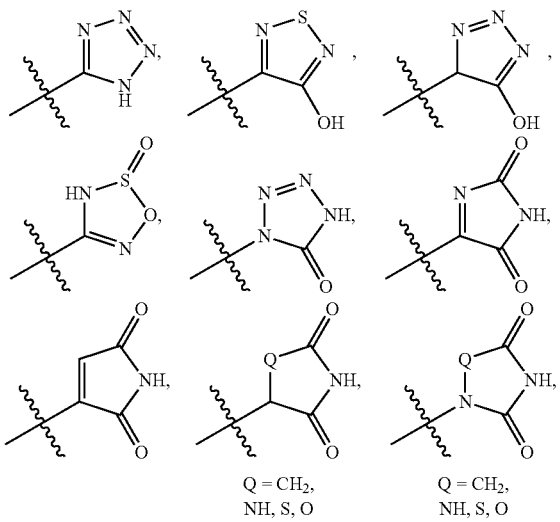

Q = $CH_2$, NH, S, O

Q = $CH_2$, NH, S, O

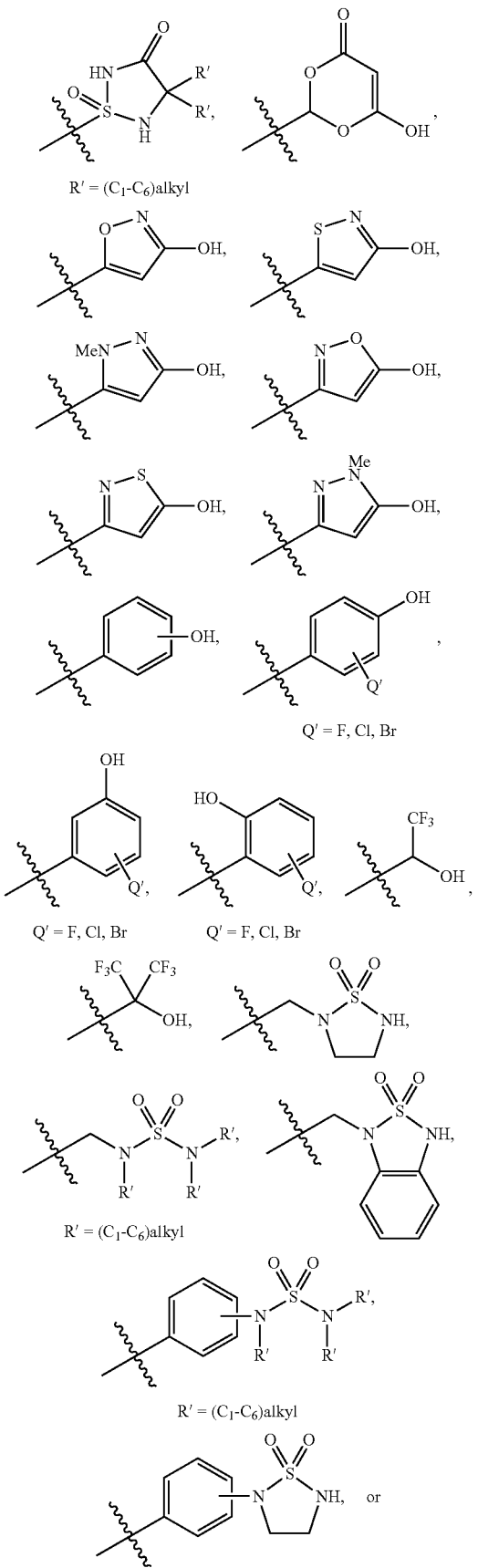

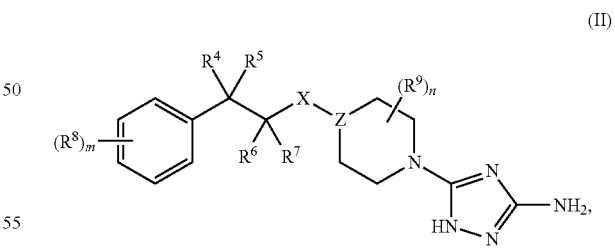

R' = (C₁-C₆)alkyl $R^2$, $R^3$, $R^4$, $R^5$, $R^6$, and $R^7$ are each independently H, $(C_1-C_6)$alkyl, aryl$(C_1-C_6)$alkyl, or aryl; or $R^2$, taken together with $R^6$ or $R^7$, forms a 5- or 6-membered ring;

$R^8$ is selected from the group consisting of halo, $(C_1-C_6)$ alkyl, $(C_1-C_6)$haloalkyl, and $(C_3-C_6)$cycloalkyl;

$R^9$ is selected from the group consisting of OH, $(C_1-C_6)$ alkyl, $(C_3-C_6)$cycloalkyl, aryl$(C_1-C_6)$alkyl, aryl, $(C_1-C_6)$ alkoxyl, $(C_1-C_6)$haloalkyl, $(C_1-C_6)$hydroxyalkyl, heteroaryl, and heteroaryl$(C_1-C_6)$alkyl;

$R^{10}$ and $R^{11}$ are each independently selected from H and $(C_1-C_6)$alkyl;

m is an integer from 0-5;

n is an integer from 0-2;

further wherein any occurrence of $(C_1-C_6)$alkyl, aryl$(C_1-C_6)$ alkyl, aryl, $(C_3-C_6)$cycloalkyl, $(C_1-C_6)$alkoxyl, $(C_1-C_6)$ haloalkyl, $(C_1-C_6)$hydroxyalkyl, heteroaryl, or heteroaryl $(C_1-C_6)$alkyl is optionally and independently substituted by one or more substituents selected from the group consisting of halo, $(C_1-C_6)$alkyl, $(C_1-C_6)$haloalkyl, aryl, —NH₂, —NH$((C_1-C_6)$alkyl), —N$((C_1-C_6)$alkyl)₂, —OH, $(C_3-C_6)$cycloalkyl, $(C_1-C_6)$alkoxyl, $(C_1-C_6)$haloalkoxyl, —SH, —S$((C_1-C_6)$alkyl), $(C_1-C_6)$hydroxyalkyl, and $(C_1-C_6)$alkoxy$(C_1-C_6)$alkyl, —CN, —CF₃, —C(O)NH₂, —C(O)NH($R^{12}$), —C(O)N($R^{12}$)₂, —N(H)C(O)($R^{12}$), —N($R^{12}$)C(O)($R^{12}$), —S(O)₂NH₂, —S(O)₂NH($R^{12}$), —S(O)₂N($R^{12}$)₂, —N(H)S(O)₂($R^{12}$), —N($R^{12}$)S(O)₂ ($R^{12}$), —NHC(O)NH₂, —NHC(O)NH($R^{12}$), and —NHC(O)N($R^{12}$)₂; and each occurrence of $R^{12}$ is independently selected from the group consisting of $(C_1-C_6)$alkyl), aryl, and aryl$(C_1-C_6)$ alkyl.

In another aspect, the invention provides a compound represented by formula (II) or a pharmaceutically acceptable salt thereof:

(II)

wherein:

X is NH or N(C($R^1$)($R^2$)($R^3$)), and Z is CR¹⁰; or X is CHR¹¹ or C($R^{11}$)(C($R^1$)($R^2$)($R^3$)), and Z is N;

$R^1$, $R^2$, $R^3$, $R^4$, $R^5$, $R^6$, and $R^7$ are each independently H, $(C_1-C_6)$alkyl, aryl$(C_1-C_6)$alkyl, or aryl; or $R^2$, taken together with $R^6$ or $R^7$, forms a 5- or 6-membered ring;

$R^8$ is selected from the group consisting of halo, $(C_1-C_6)$ alkyl, $(C_1-C_6)$haloalkyl and $(C_3-C_6)$cycloalkyl;

$R^9$ is selected from the group consisting of Y, aryl substituted by Y, and $(C_1-C_6)$alkyl substituted by Y;

Y is —CO$_2$H, —C(O)O(C$_1$-C$_6$)alkyl, —C(O)N(H)OH, —C(O)N(H)CN, —C(O)NH$_2$, —C(O)NH((C$_1$-C$_6$)alkyl), —C(O)N((C$_1$-C$_6$)alkyl)$_2$, —C(O)NH(aryl), —C(O)N(aryl)((C$_1$-C$_6$)alkyl), —C(O)N(aryl)$_2$, —C(O)NH((C$_1$-C$_6$)haloalkyl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)(C$_1$-C$_6$)alkyl, —S(O)$_2$NHC(O)(C$_1$-C$_6$)haloalkyl, —S(O)$_2$NHC(O)aryl, —N(H)S(O)$_2$(C$_1$-C$_6$)alkyl, —N(H)S(O)$_2$aryl, N(H)S(O)$_2$(C$_1$-C$_6$)haloalkyl, —NHC(O)((C$_1$-C$_6$)alkyl), —NHC(O)((C$_1$-C$_6$)haloalkyl), —NHC(O)(aryl), —NHC(O)NH(C$_1$-C$_6$)alkyl, —NHC(O)NHaryl, —C(O)N(H)S(O)$_2$(C$_1$-C$_6$)alkyl, —C(O)N(H)S(O)$_2$aryl, C(O)N(H)S(O)$_2$((C$_1$-C$_6$)haloalkyl), —P(O)(OH)$_2$,

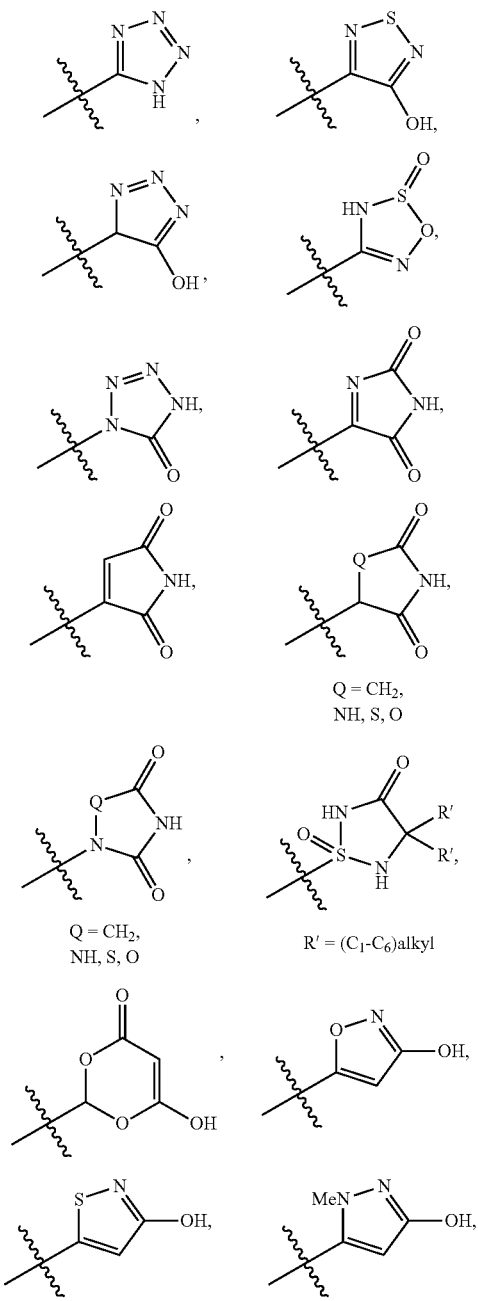
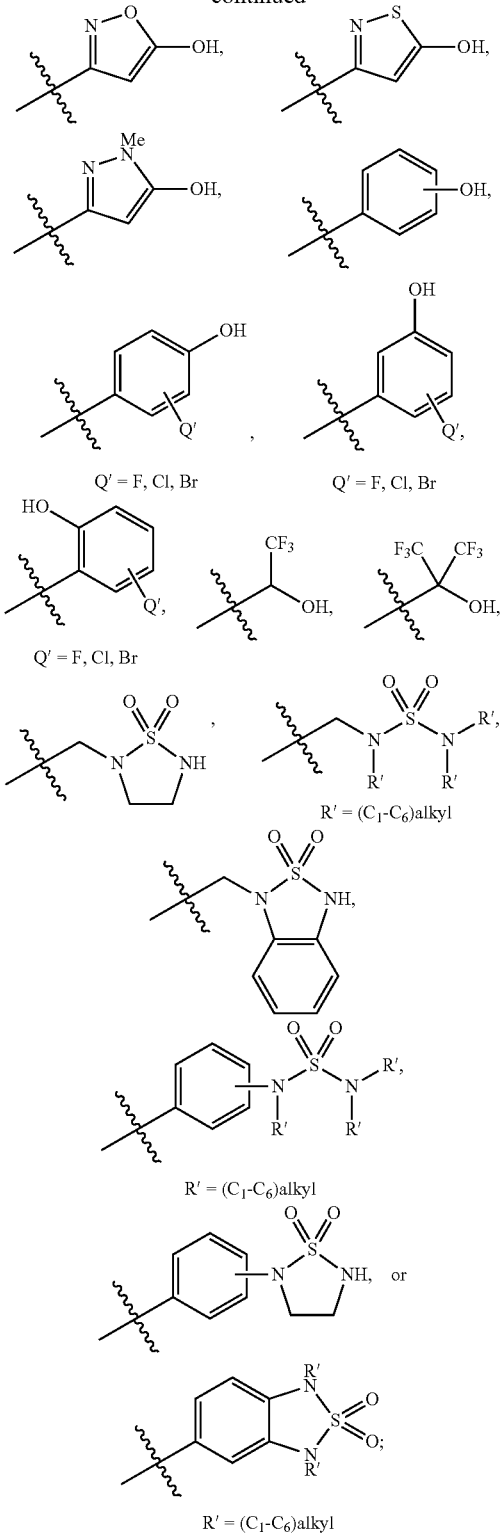

R$^{10}$ and R$^{11}$ are each independently selected from H and (C$_1$-C$_6$)alkyl;
m is an integer from 0-5;
n is 1 or 2;
further wherein any occurrence of (C$_1$-C$_6$)alkyl, aryl(C$_1$-C$_6$)alkyl, aryl, (C$_3$-C$_6$)cycloalkyl, (C$_1$-C$_6$)alkoxyl, (C$_1$-C$_6$)haloalkyl, (C$_1$-C$_6$)hydroxyalkyl, heteroaryl, or heteroaryl (C₁-C₆)alkyl is optionally and independently substituted by one or more substituents selected from the group consisting of halo, (C₁-C₆)alkyl, (C₁-C₆)haloalkyl, aryl, —NH₂, —NH((C₁-C₆)alkyl), —N((C₁-C₆)alkyl)₂, —OH, (C₃-C₆)cycloalkyl, (C₁-C₆)alkoxyl, (C₁-C₆)haloalkoxyl, —SH, —S((C₁-C₆)alkyl), (C₁-C₆)hydroxyalkyl, and (C₁-C₆)alkoxy(C₁-C₆)alkyl, —CN, —CF₃, —C(O)NH₂, —C(O)NH(R¹²), —C(O)N(R¹²)₂, —N(H)C(O)(R¹²), —N(R¹²)C(O)(R¹²), —S(O)₂NH₂, —S(O)₂NH(R¹²), —S(O)₂N(R¹²)₂, —N(H)S(O)₂(R¹²), —N(R¹²)S(O)₂(R¹²), —NHC(O)NH₂, —NHC(O)NH(R¹²), and —NHC(O)N(R¹²)₂; and each occurrence of R¹² is independently selected from the group consisting of (C₁-C₆)alkyl), aryl, and aryl(C₁-C₆)alkyl.

In another aspect, the invention provides a compound represented by formula (III), or a pharmaceutically acceptable salt thereof,

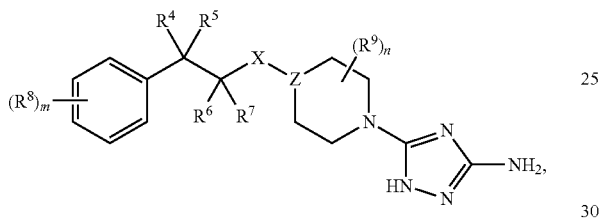

(III)

wherein:
X is NH or N(C(R¹)(R²)(R³)), and Z is CR¹⁰; or X is CHR¹¹ or C(R¹¹)(C(R¹)(R²)(R³)), and Z is N;
R¹, R², R³, R⁴, R⁵, and R⁷ are each independently H, (C₁-C₆)alkyl, aryl(C₁-C₆)alkyl, or aryl; or R¹ or R², taken together with R⁷, forms a 5- or 6-membered ring;
R⁶ is selected from the group consisting of Y, aryl substituted by Y, and (C₁-C₆)alkyl substituted by Y;
Y is —CO₂H, —C(O)O(C₁-C₆)alkyl, —C(O)N(H)OH, —C(O)N(H)CN, —C(O)NH₂, —C(O)NH((C₁-C₆)alkyl), —C(O)N((C₁-C₆)alkyl)₂, —C(O)NH(aryl), —C(O)N(aryl)((C₁-C₆)alkyl), —C(O)N(aryl)₂, —C(O)NH((C₁-C₆)haloalkyl), —S(O)₂NH₂, —S(O)₂NH((C₁-C₆)alkyl), —S(O)₂NH((C₁-C₆)haloalkyl), —S(O)₂NH(aryl), —S(O)₂NHC(O)(C₁-C₆)alkyl, —S(O)₂NHC(O)(C₁-C₆)haloalkyl, —S(O)₂NHC(O)aryl, —N(H)S(O)₂(C₁-C₆)alkyl, —N(H)S(O)₂aryl, N(H)S(O)₂(C₁-C₆)haloalkyl, —NHC(O)((C₁-C₆)alkyl), —NHC(O)((C₁-C₆)haloalkyl), —NHC(O)(aryl), —NHC(O)NH(C₁-C₆)alkyl, —NHC(O)NHaryl, —C(O)N(H)S(O)₂(C₁-C₆)alkyl, —C(O)N(H)S(O)₂aryl, C(O)N(H)S(O)₂((C₁-C₆)haloalkyl), —P(O)(OH)₂,

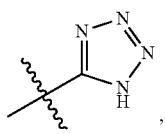 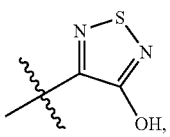

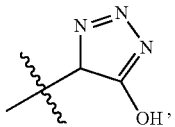 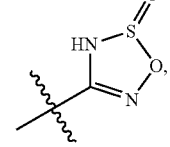

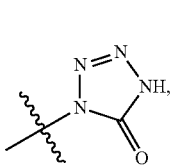 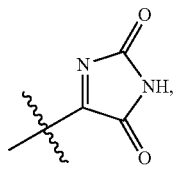

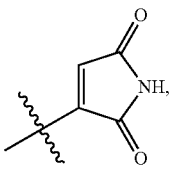 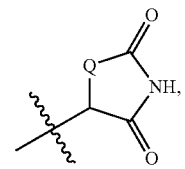

Q = CH₂, NH, S, O

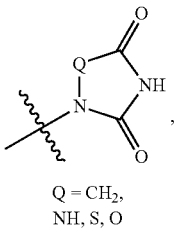 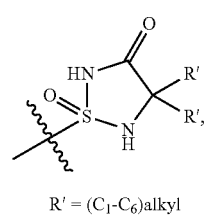

Q = CH₂, NH, S, O

R' = (C₁-C₆)alkyl

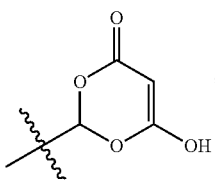 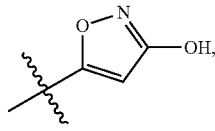

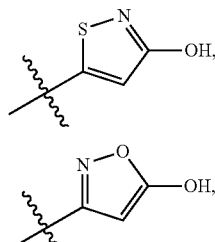 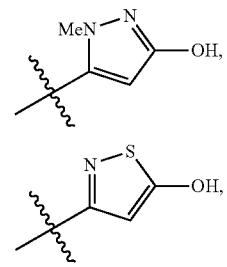

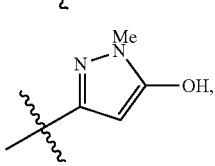 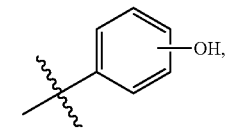

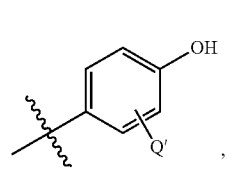 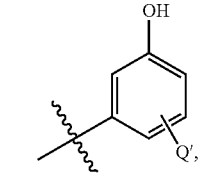

Q' = F, Cl, Br       Q' = F, Cl, Br

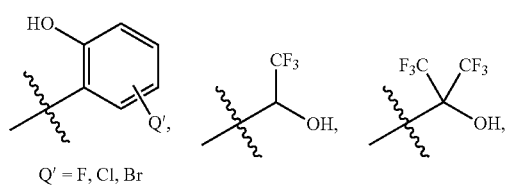

Q' = F, Cl, Br

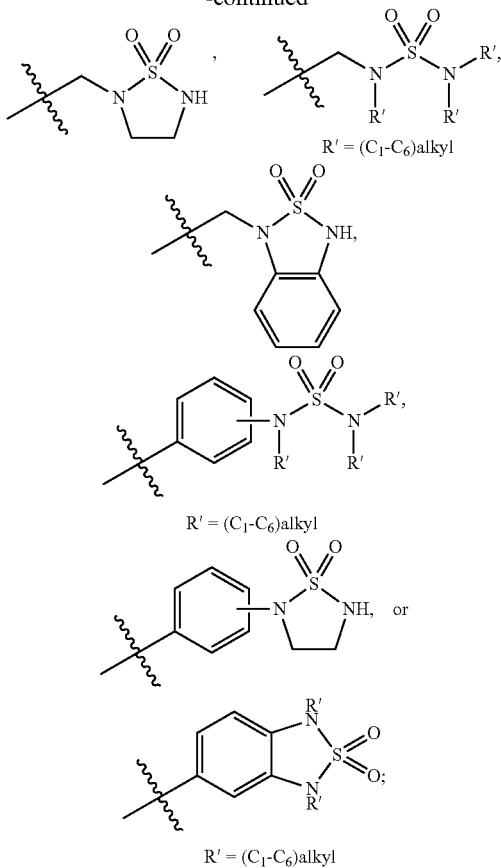

R' = (C₁-C₆)alkyl

R⁸ is selected from the group consisting of halo, (C₁-C₆)alkyl, (C₁-C₆)haloalkyl and (C₃-C₆)cycloalkyl;

R⁹ is selected from the group consisting of OH, (C₁-C₆)alkyl, (C₃-C₆)cycloalkyl, aryl(C₁-C₆)alkyl, aryl, (C₁-C₆)alkoxyl, (C₁-C₆)haloalkyl, (C₁-C₆)hydroxyalkyl, heteroaryl, and heteroaryl(C₁-C₆)alkyl;

R¹⁰ and R¹¹ are each independently selected from H and (C₁-C₆)alkyl;

m is an integer from 0-5; and n is an integer from 0-2;

further wherein any occurrence of (C₁-C₆)alkyl, aryl(C₁-C₆)alkyl, aryl, (C₃-C₆)cycloalkyl, (C₁-C₆)alkoxyl, (C₁-C₆)haloalkyl, (C₁-C₆)hydroxyalkyl, heteroaryl, or heteroaryl (C₁-C₆)alkyl is optionally and independently substituted by one or more substituents selected from the group consisting of halo, (C₁-C₆)alkyl, (C₁-C₆)haloalkyl, aryl, —NH₂, —NH((C₁-C₆)alkyl), —N((C₁-C₆)alkyl)₂, —OH, (C₃-C₆)cycloalkyl, (C₁-C₆)alkoxyl, (C₁-C₆)haloalkoxyl, —SH, —S((C₁-C₆)alkyl), (C₁-C₆)hydroxyalkyl, and (C₁-C₆)alkoxy(C₁-C₆)alkyl, —CN, —CF₃, —C(O)NH₂, —C(O)NH(R¹²), —C(O)N(R¹²)₂, —N(H)C(O)(R¹²), —N(R¹²)C(O)(R¹²), —S(O)₂NH₂, —S(O)₂NH(R¹²), —S(O)₂N(R¹²)₂, —N(H)S(O)₂(R¹²), —N(R¹²)S(O)₂(R¹²), —NHC(O)NH₂, —NHC(O)NH(R¹²), and —NHC(O)N(R¹²)₂; and each occurrence of R¹² is independently selected from the group consisting of (C₁-C₆)alkyl), aryl, and aryl(C₁-C₆)alkyl.

Also provided herein are pharmaceutical compositions, comprising a compound of the invention; and a pharmaceutically acceptable carrier.

Also provided herein are methods for treating asthma, comprising administering to a subject in need thereof a therapeutically effective amount of a compound of the invention.

Also provided herein are methods for treating a reaction caused by an allergen, comprising administering to a subject in need thereof a therapeutically effective amount of a compound of the invention.

In another aspect, the invention provides methods for treating a fungal or parasitic infection, comprising administering to a subject in need thereof a therapeutically effective amount of a compound of the invention.

In another aspect, the invention provides methods for assessing the efficacy of an agent for treating asthma in a subject, comprising:

a) detecting in a subject sample at a first point in time, the expression level of acidic mammalian chitinase protein;

b) repeating step a) at one or more subsequent points in time after administration of the agent; and c) comparing expression level of acidic mammalian chitinase protein detected in step a) with the expression level detected in step b), wherein a higher expression level of acidic mammalian chitinase protein at the first point in time relative to at least one subsequent point in time indicates that the agent is efficacious in treating asthma.

The invention also provides methods for identifying an agent for treating asthma, comprising:

a) contacting a sample comprising acidic mammalian chitinase protein with the agent; and b) determining the ability of the agent to inhibit activity of acidic mammalian chitinase protein, wherein decreased activity of acidic mammalian chitinase protein identifies an agent for treating asthma.

DETAILED DESCRIPTION

The present invention is based on the unexpected discovery that chemical modification of an amino triazole small molecule with a carboxylate functional group or an bioisosteric polar functional group produces a compound effective as an inhibitor of AMCase.

The amino triazole compounds having substitution by a carboxylate functional group, or by an bioisosteric functional group, effectively inhibit AMCase, and are useful in the treatment of disorders associated with upregulated and dysregulated AMCase activity, such as asthma and allergic reactions.

DEFINITIONS

The articles "a" and "an" are used herein to refer to one or to more than one (i.e., to at least one) of the grammatical object of the article. By way of example, "an element" means one element or more than one element.

The terms used herein may be preceded and/or followed by a single dash "—", or a double dash "=", to indicate the bond order of the bond between the named substituent and its parent moiety; a single dash indicates a single bond and a double dash indicates a double bond. In the absence of a single or double dash, it is understood that a single bond is formed between the substituent and its parent moiety; further, substituents are intended to be read "from left to right," unless a dash indicates otherwise. For example, (C₁-C₆)-alkoxycarbonyloxy and —OC(O)(C₁-C₆)alkyl indicate the same functionality; similarly arylalkyl and -alkylaryl indicate the same functionality.

The term "heteroatom" is art-recognized and refers to an atom of any element other than carbon or hydrogen. Illustrative heteroatoms include boron, nitrogen, oxygen, phosphorus, sulfur and selenium.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, 10 or fewer, or preferably 1-6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" means mono- or bicyclic or bridged saturated or partially saturated carbocyclic rings, each having from 3 to 12 carbon atoms. Certain cycloalkyls have from 3-8, or from 3-6 carbon atoms in their ring structure. Certain cycloalkyls have from 5-12 carbon atoms in their ring structure, and may have 6-10 carbons in the ring structure. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "heterocyclyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 14, or 3 to 12 atoms including at least one heteroatom, such as nitrogen, oxygen, or sulfur. More preferred heterocycloalkyl groups have from 5-10 ring members where from 1-4 of the ring members are hetero atoms selected from the group consisting of O, N, and S, the remaining ring atoms being C. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinicludinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group is optionally substituted by one or more substituents as described below.

As used herein, the term "heterocyclylene" refers to a bivalent heterocyclyl (heterocycloalkyl) group, i.e., a cyclic alkylene group, having from 3-10 members and from 1-4 hetero atoms selected from S, O, and N. An example is piperidine-2,3-dicarboxylic acid, i.e., in that compound, the piperidine ring is a heterocyclyl group.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "cycloalkylalkyl" as used herein refers to an alkyl group substituted with one or more cycloalkyl groups.

The term "heterocycloalkylalkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

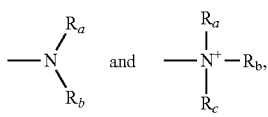

wherein $R_a$, $R_b$, and $R_c$ each independently represent a hydrogen, an alkyl, an alkenyl, —$(CH_2)_x$—$R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —$(CH_2)_x$—$R_d$. In certain embodiments, the term "amino" refers to $NH_2$.

The term "amido", as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

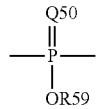

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

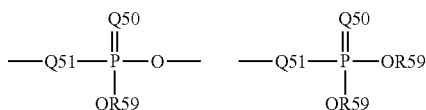

wherein Q50 and R59, each independently, are defined above, and Q51 represents O, S or N; for example, —O—P(O)(OH)Me or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "azide" or "azido", as used herein, means an $N_3$ group.

The term "carbonyl" as used herein refers to —C(=O)—.
The term "thiocarbonyl" as used herein refers to —C(=S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—.
The term "carboxy", as used herein, means a —CO$_2$H group.

The term "aryl" is a term of art and as used herein refers to includes monocyclic, bicyclic and polycyclic aromatic hydrocarbon groups, for example, benzene, naphthalene, anthracene, 1,2,3,4-tetrahydronaphthalene, indene, 2,3-dihydroindene, and pyrene. The aromatic ring may be substituted at one or more ring positions with one or more substituents, such as halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. Representative examples of the polcyclic aryl ring systems include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-6-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl, or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted. In certain embodiments, the term "aryl" refers to a phenyl group.

The term "heteroaryl" is a term of art and as used herein refers to a monocyclic, bicyclic, and polycyclic aromatic group having 3 to 14, 5 to 14, or 3 to 12 total atoms including one or more heteroatoms such as nitrogen, oxygen, or sulfur in the ring structure. More preferred heteroaryl groups have from 5-10 ring members where from 1-4 of the ring members are hetero atoms selected from the group consisting of O, N, and S. Exemplary heteroaryl groups include, for example, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. Any heteroaryl or bicyclic heteroaryl can be optionally substituted as detailed below.

The term "aralkyl", "arylalkyl", or "aryl($C_1$-$C_6$)alkyl" is a term of art and as used herein refers to an alkyl group, for example a $C_1$-$C_6$ alkyl group, substituted with an aryl group, wherein the moiety is appended to the parent molecule through the alkyl group.

The term "heteroaralkyl", "heteroarylalkyl", or "heteroaryl($C_1$-$C_6$)alkyl" is a term of art and as used herein refers to an alkyl group, for example a $C_1$-$C_6$ alkyl group, substituted with a heteroaryl group, appended to the parent molecular moiety through the alkyl group.

The term "alkoxy" or "alkoxyl" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2$=CH—$CH_2$—O—) and vinyloxy (i.e., $CH_2$=CH—O—).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The terms "cyano" and "nitrile" is a term of art and as used herein refers to —CN.

The term "nitro", as used herein, means —$NO_2$.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms. The term "haloalkoxyl" refers to an alkoxy group, as defined herein, wherein some or all of the hydrogens are replaced with halogen atoms. An exemplary haloalkyl group is trifluoromethyl.

The term "hydroxy" is a term of art and as used herein refers to OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3Si$—) group (i.e., (hydrocarbyl)$_3Si$—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or other substitutents described above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$* ed.; Wiley: New York, 1991). Protected forms of the inventive compounds are included within the scope of this invention.

A "saturated" or "fully saturated" compound means that the referenced chemical structure does not contain any multiple carbon-carbon bonds. For example, a saturated cycloalkyl group as defined herein includes cyclohexyl, cyclopropyl, and the like.

A "unsaturated" or "partially saturated" compound means that the referenced chemical structure may contains on or more multiple carbon-carbon bonds, but is not aromatic. For example, a unsaturated cycloalkyl group as defined herein includes cyclohexenyl, cyclopentenyl, cyclohexadienyl, and the like.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

As used herein, a protic solvent is a solvent that has a hydrogen atom bound to an oxygen (as in a hydroxyl group) or a nitrogen (as in an amine group). In general terms, any solvent that contains labile H⁺ is called a protic solvent. The molecules of such solvents readily donate protons (H⁺) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, t-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

"Modulating" or "modulate" refers to the treating, prevention, suppression, enhancement or induction of a function, condition or disorder.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, "subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Compounds of the Invention

In certain embodiments, the invention relates to a compound represented by formula (I), or a pharmaceutically acceptable salt thereof,

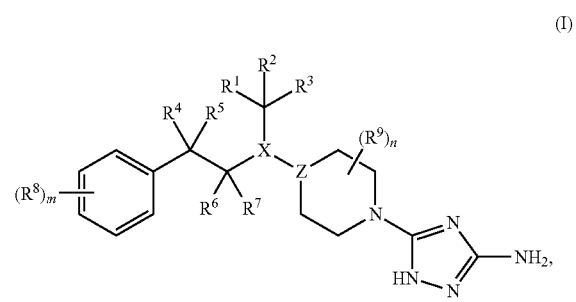

(I)

wherein:

X is N, and Z is $CR^{10}$; or X is $CR^{11}$, and Z is N;

$R^1$ is selected from the group consisting of Y, aryl substituted by Y, and $(C_1\text{-}C_6)$alkyl substituted by Y;

Y is —$CO_2H$, —$C(O)O(C_1\text{-}C_6)$alkyl, —C(O)N(H)OH, —C(O)N(H)CN, —C(O)NH$_2$, —C(O)NH(($C_1\text{-}C_6$)alkyl), —C(O)N(($C_1\text{-}C_6$)alkyl)$_2$, —C(O)NH(aryl), —C(O)N(aryl)(($C_1\text{-}C_6$)alkyl), —C(O)N(aryl)$_2$, —C(O)NH(($C_1$-$C_6$)haloalkyl), —S(O)$_2$NH$_2$, —S(O)$_2$NH(($C_1\text{-}C_6$)alkyl), —S(O)$_2$NH(($C_1\text{-}C_6$)haloalkyl), —S(O)$_2$NH(aryl), —S(O)$_2$NHC(O)($C_1\text{-}C_6$)alkyl, —S(O)$_2$NHC(O)($C_1\text{-}C_6$)haloalkyl, —S(O)$_2$NHC(O)aryl, —N(H)S(O)$_2$($C_1\text{-}C_6$)alkyl, —N(H)S(O)$_2$aryl, N(H)S(O)$_2$($C_1\text{-}C_6$)haloalkyl, —NHC(O)(($C_1\text{-}C_6$)alkyl), —NHC(O)(($C_1\text{-}C_6$)haloalkyl), —NHC(O)(aryl), —NHC(O)NH($C_1\text{-}C_6$)alkyl, —NHC(O)NHaryl, —C(O)N(H)S(O)$_2$($C_1\text{-}C_6$)alkyl, —C(O)N(H)S(O)$_2$aryl, C(O)N(H)S(O)$_2$(($C_1\text{-}C_6$)haloalkyl), —P(O)(OH)$_2$,

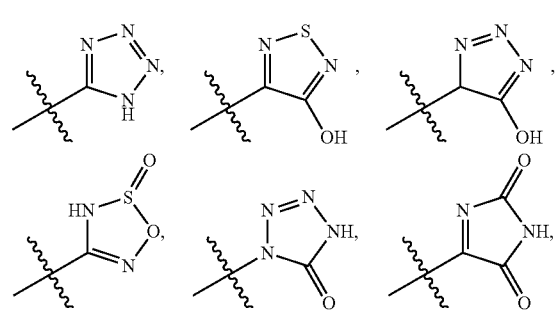

R², R³, R⁴, R⁵, R⁶, and R⁷ are each independently H, $(C_1-C_6)$alkyl, aryl$(C_1-C_6)$alkyl, or aryl; or R², taken together with R⁶ or R⁷, forms a 5- or 6-membered ring;

R⁸ is selected from the group consisting of halo, $(C_1-C_6)$alkyl, $(C_1-C_6)$haloalkyl, and $(C_3-C_6)$cycloalkyl;

R⁹ is selected from the group consisting of OH, $(C_1-C_6)$alkyl, $(C_3-C_6)$cycloalkyl, aryl$(C_1-C_6)$alkyl, aryl, $(C_1-C_6)$alkoxyl, $(C_1-C_6)$haloalkyl, $(C_1-C_6)$hydroxyalkyl, heteroaryl, and heteroaryl$(C_1-C_6)$alkyl;

R¹⁰ and R¹¹ are each independently selected from H and $(C_1-C_6)$alkyl;

m is an integer from 0-5;

n is an integer from 0-2;

further wherein any occurrence of $(C_1-C_6)$alkyl, aryl$(C_1-C_6)$alkyl, aryl, $(C_3-C_6)$cycloalkyl, $(C_1-C_6)$alkoxyl, $(C_1-C_6)$haloalkyl, $(C_1-C_6)$hydroxyalkyl, heteroaryl, or heteroaryl$(C_1-C_6)$alkyl is optionally and independently substituted by one or more substituents selected from the group consisting of halo, $(C_1-C_6)$alkyl, $(C_1-C_6)$haloalkyl, aryl, —NH₂, —NH(($C_1-C_6$)alkyl), —N(($C_1-C_6$)alkyl)₂, —OH, $(C_3-C_6)$cycloalkyl, $(C_1-C_6)$alkoxyl, $(C_1-C_6)$haloalkoxyl, —SH, —S(($C_1-C_6$)alkyl), $(C_1-C_6)$hydroxyalkyl, and $(C_1-C_6)$alkoxy$(C_1-C_6)$alkyl, —CN, —CF₃, —C(O)NH₂, —C(O)NH(R¹²), —C(O)N(R¹²)₂, —N(H)C(O)(R¹²), —N(R¹²)C(O)(R¹²), —S(O)₂NH₂, —S(O)₂NH(R¹²), —S(O)₂N(R¹²)₂, —N(H)S(O)₂(R¹²), —N(R¹²)S(O)₂(R¹²), —NHC(O)NH₂, —NHC(O)NH(R¹²), and —NHC(O)N(R¹²)₂; and each occurrence of R¹² is independently selected from the group consisting of $(C_1-C_6)$alkyl), aryl, and aryl$(C_1-C_6)$alkyl.

In certain embodiments, R¹ is Y.

In certain embodiments, R¹ is aryl substituted by Y.

In certain embodiments, R¹ is $(C_1-C_6)$alkyl substituted by Y.

In certain embodiments, Y is —CO₂H, —C(O)NH₂, —C(O)NH($C_1-C_6$)alkyl, —C(O)N(($C_1-C_6$)alkyl)₂, —C(O)NH(aryl), C(O)N(aryl)(($C_1-C_6$)alkyl), C(O)N(aryl)₂, —C(O)NH(($C_1-C_6$)haloalkyl), —S(O)₂NH₂, —S(O)₂NH(($C_1-C_6$)alkyl), —S(O)₂NH(($C_1-C_6$)haloalkyl), —S(O)₂NH(aryl), —S(O)₂NHC(O)($C_1-C_6$)alkyl, —S(O)₂NHC(O)($C_1-C_6$)haloalkyl, —S(O)₂NHC(O)aryl, —N(H)S(O)₂($C_1-C_6$)alkyl, —N(H)S(O)₂aryl, —N(H)S(O)₂($C_1-C_6$)haloalkyl, —NHC(O)(($C_1-C_6$)alkyl), —NHC(O)(($C_1-C_6$)haloalkyl), —NHC(O)(aryl), —NHC(O)NH($C_1$-$C_6$)alkyl, —NHC(O)NHaryl, —C(O)N(H)S(O)$_2$($C_1$-$C_6$)alkyl, —C(O)N(H)S(O)$_2$aryl, C(O)N(H)S(O)$_2$(($C_1$-$C_6$)haloalkyl), or 1H-tetrazolyl.

In certain embodiments, the invention relates to a compound of formula (I), wherein $R^1$ is selected from the group consisting of:
- $CO_2H$;
- $C(O)NH_2$;
- $C(O)NH((C_1$-$C_6)$alkyl);
- C(O)NH(aryl);
- 1H-tetrazolyl;
- aryl substituted by —$CO_2H$, —C(O)NH$_2$, —C(O)NH($C_1$-$C_6$)alkyl, —C(O)NH(aryl), —S(O)$_2$NH$_2$, —S(O)$_2$NH(($C_1$-$C_6$)alkyl), —S(O)$_2$NH(($C_1$-$C_6$)haloalkyl), —S(O)$_2$NH(aryl), —S(O)$_2$NHC(O)($C_1$-$C_6$)alkyl, —S(O)$_2$NHC(O)($C_1$-$C_6$)haloalkyl, —S(O)$_2$NHC(O)aryl, —N(H)S(O)$_2$($C_1$-$C_6$)alkyl, —N(H)S(O)$_2$aryl, —C(O)N(H)S(O)$_2$($C_1$-$C_6$)alkyl, —C(O)N(H)S(O)$_2$aryl, or 1H-tetrazolyl; and
- ($C_1$-$C_6$)alkyl substituted by $CO_2H$, —NHC(O)($C_1$-$C_6$)alkyl, —NHC(O)($C_1$-$C_6$)haloalkyl, —NHC(O)aryl, —NHC(O)NH($C_1$-$C_6$)alkyl, —NHC(O)NHaryl, —N(H)S(O)$_2$($C_1$-$C_6$)alkyl, —N(H)S(O)$_2$aryl, —S(O)$_2$NH$_2$, —S(O)$_2$NH($C_1$-$C_6$)alkyl, —S(O)$_2$NH($C_1$-$C_6$)haloalkyl, —S(O)$_2$NHaryl, —S(O)$_2$NHC(O)($C_1$-$C_6$)alkyl, or —S(O)$_2$NHC(O)aryl.

In certain embodiments, $R^1$ is selected from the group consisting of:
- 1H-tetrazolyl;
- aryl substituted by —$CO_2H$, —C(O)NH$_2$, —C(O)NH($C_1$-$C_6$)alkyl, —S(O)$_2$NH$_2$, —S(O)$_2$NH(($C_1$-$C_6$)haloalkyl), —S(O)$_2$NHC(O)($C_1$-$C_6$)alkyl, —N(H)S(O)$_2$($C_1$-$C_6$)alkyl, —C(O)N(H)S(O)$_2$($C_1$-$C_6$)alkyl, or 1H-tetrazolyl; and
- ($C_1$-$C_6$)alkyl substituted by $CO_2H$, —NHC(O)aryl, —N(H)S(O)$_2$($C_1$-$C_6$)alkyl, —N(H)S(O)$_2$aryl, —S(O)$_2$NH($C_1$-$C_6$)alkyl, or —S(O)$_2$NHC(O)($C_1$-$C_6$)alkyl.

In certain embodiments, the invention relates to a compound of formula (I), wherein $R^2$ and $R^3$ are each independently selected from the group consisting of H and aryl. In certain embodiments, $R^2$ and $R^3$ are both H.

In certain embodiments, $R^2$, taken together with $R^6$ or $R^7$, forms a 5- or 6-membered ring, preferably, a 6-membered ring.

In certain embodiments, X is N; and Z is CH. In alternative embodiments, X is CH and Z is N.

In certain embodiments, $R^8$ is selected from the group consisting of halo, ($C_1$-$C_6$)haloalkyl, and ($C_1$-$C_6$)alkyl. In certain embodiments, $R^8$ is halo.

In certain embodiments, there is one occurrence of $R^8$ on the aromatic ring, i.e., m is 1.

In certain embodiments, $R^4$, $R^5$, $R^6$, and $R^7$ are each independently selected from the group consisting of H and ($C_1$-$C_6$)alkyl. In certain embodiments, $R^4$, $R^5$, $R^6$, and $R^7$ are each H.

In certain embodiments, $R^9$ is selected from the group consisting of ($C_1$-$C_6$)alkyl, ($C_3$-$C_6$)cycloalkyl, and aryl($C_1$-$C_6$)alkyl.

In certain embodiments, n is 0.

In certain embodiments, the invention relates to a compound of any one of the following structural formulae:

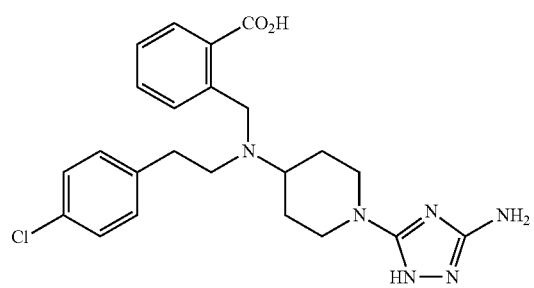

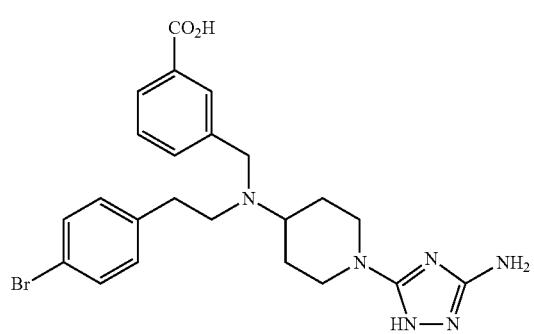

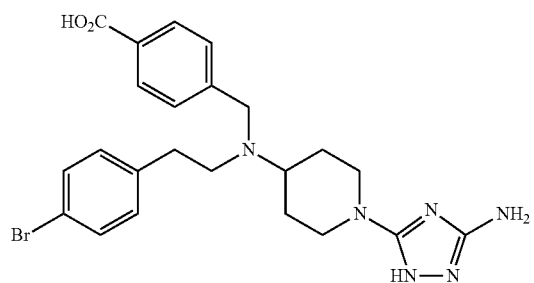

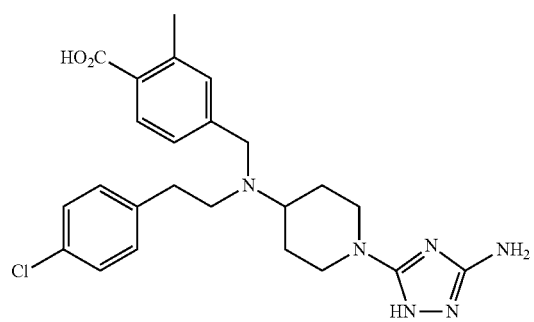

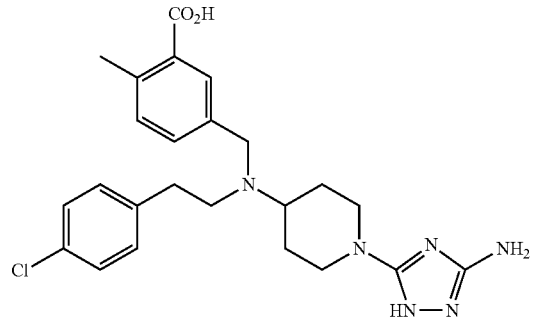

25
-continued
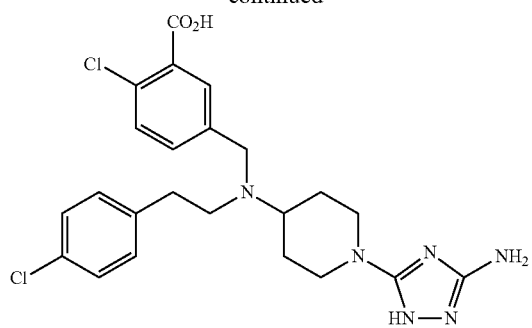
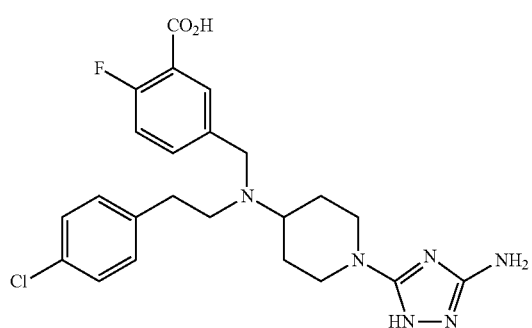
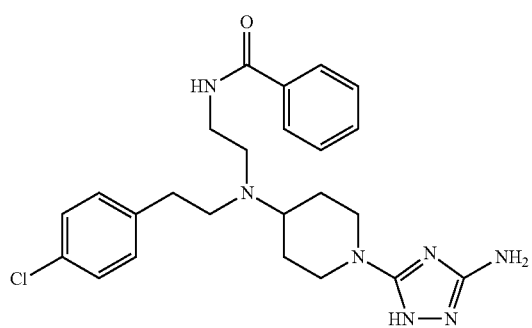
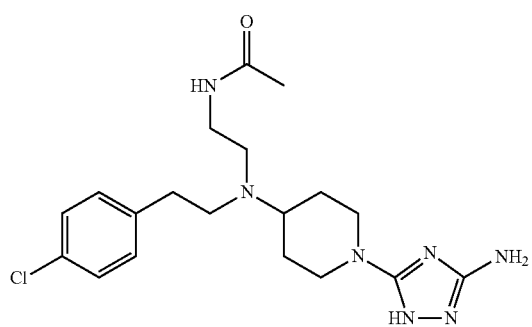
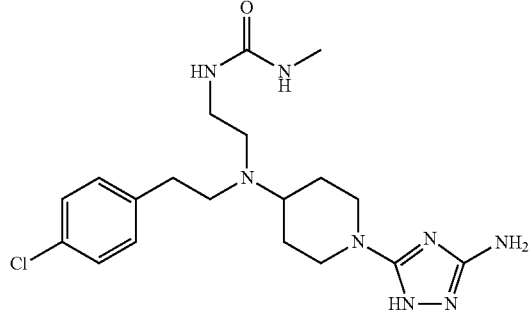
26
-continued
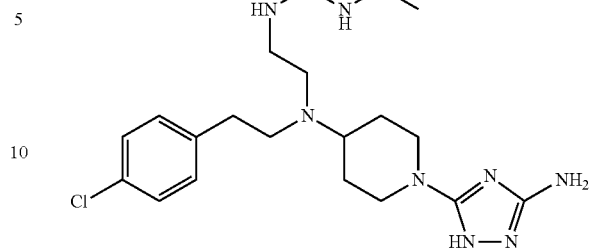
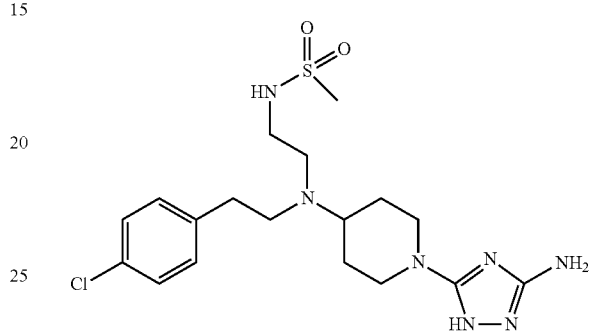
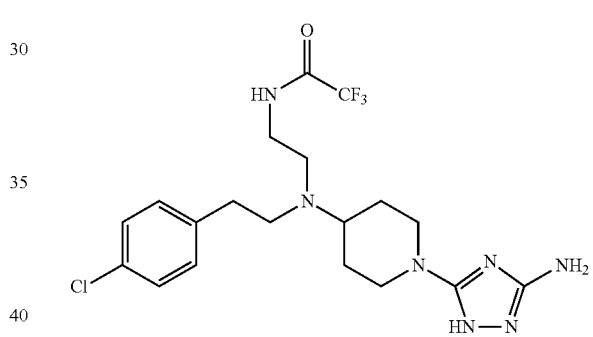
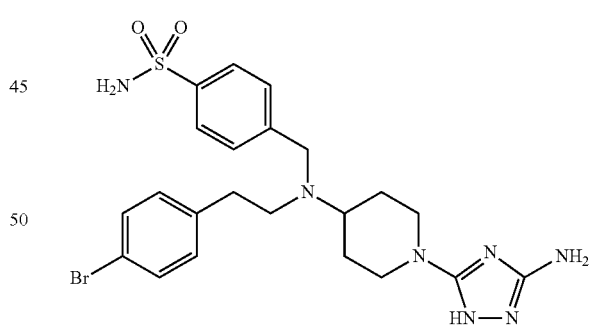
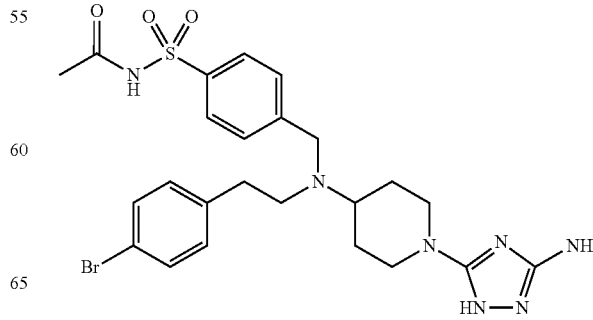

27
-continued
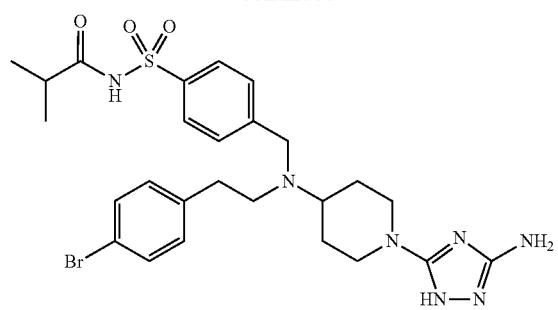
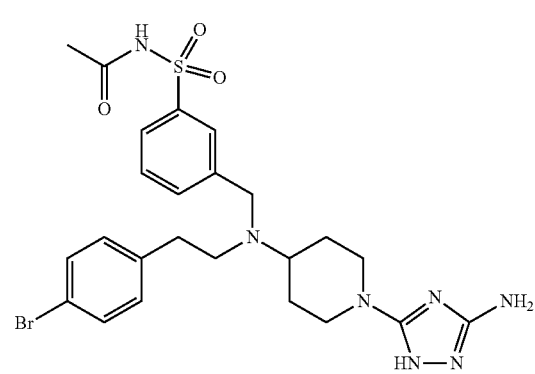
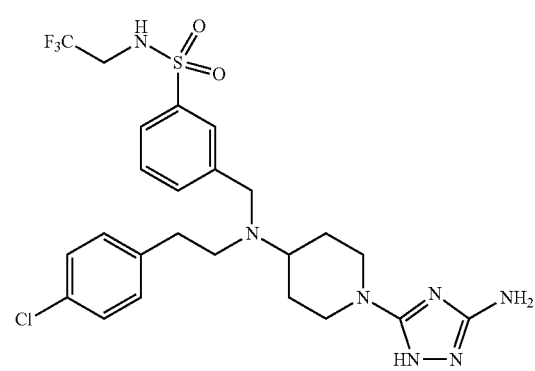
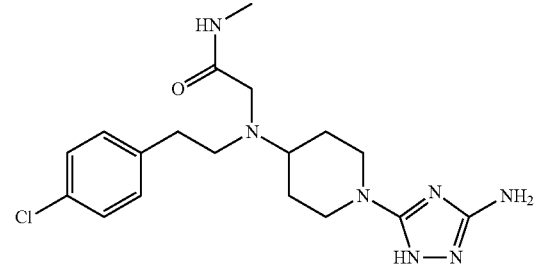
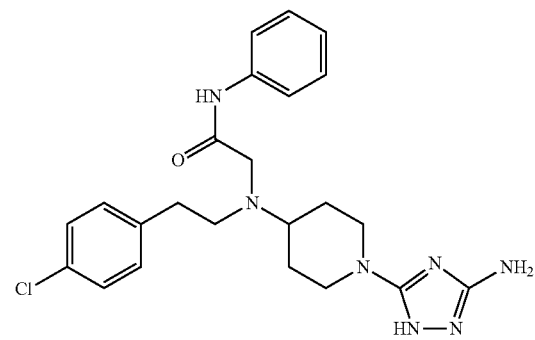
28
-continued
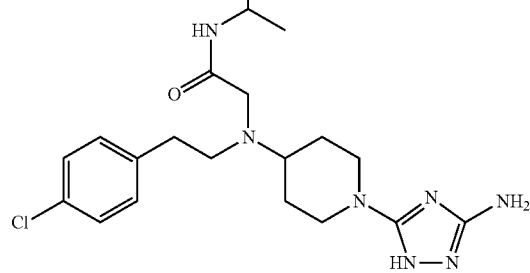
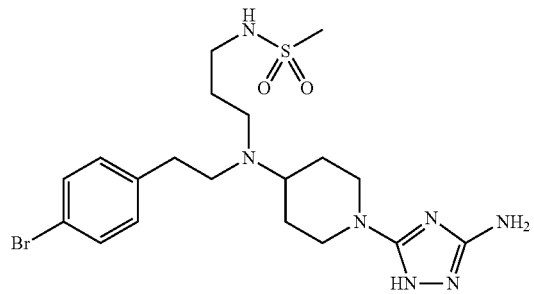
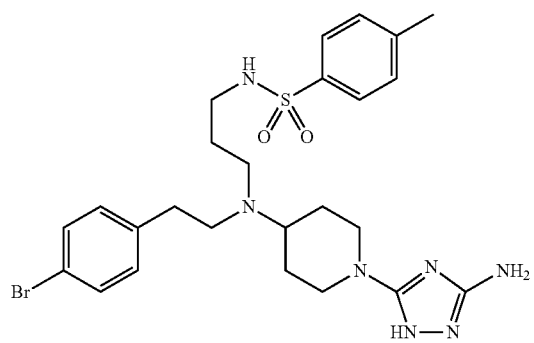
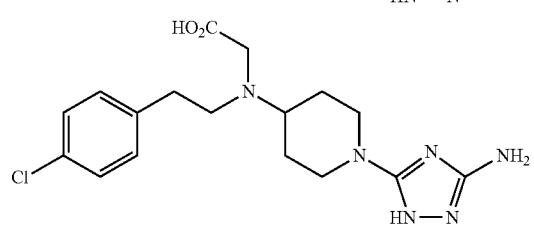
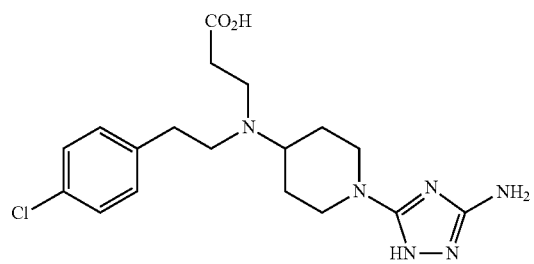
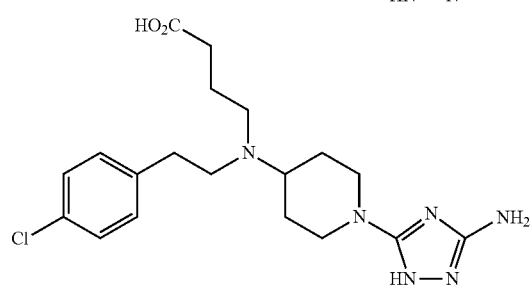

-continued
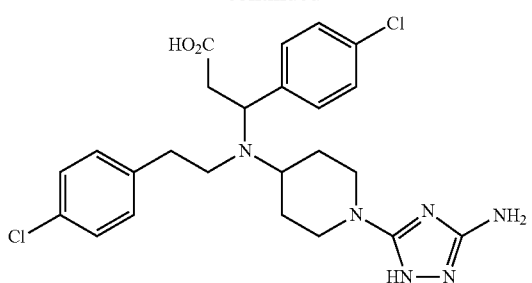
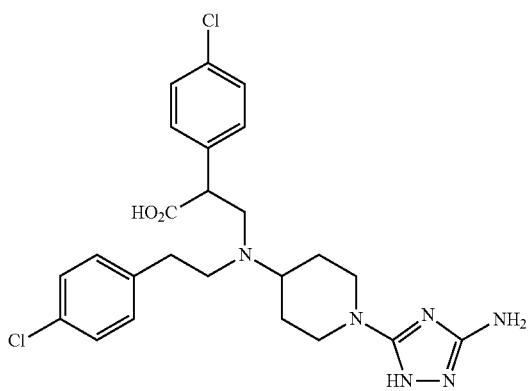
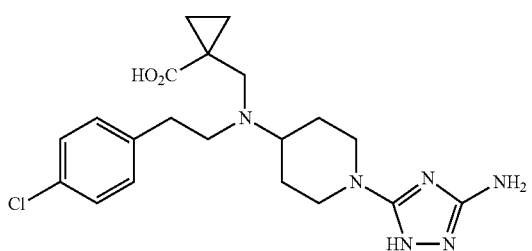
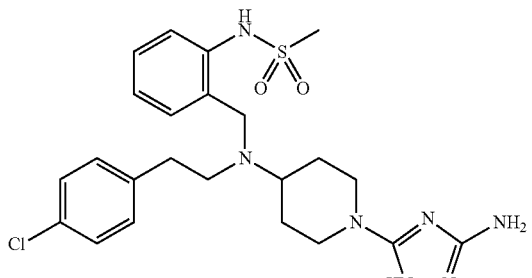
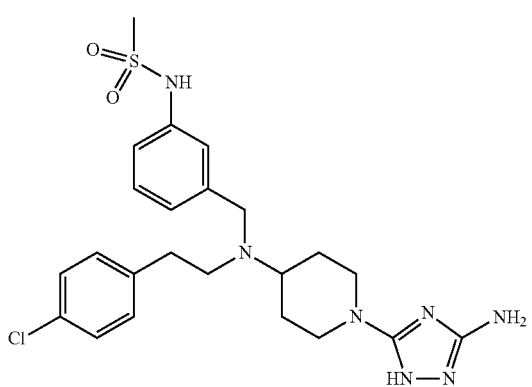
-continued
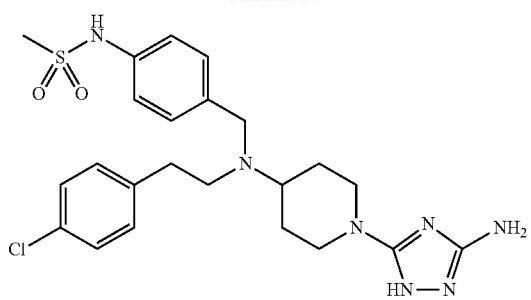
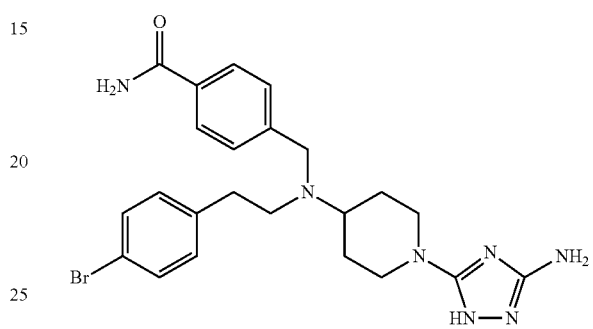
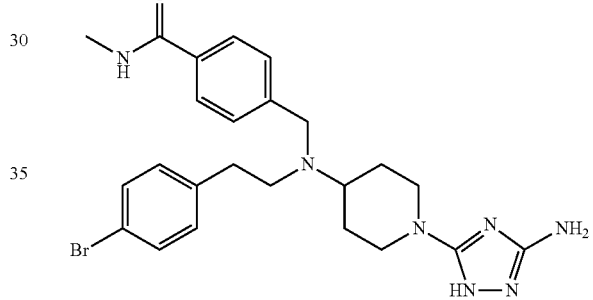
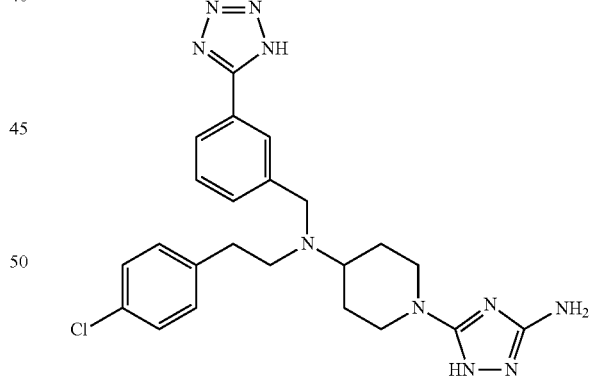
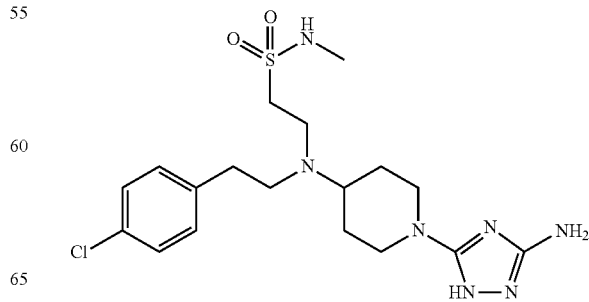

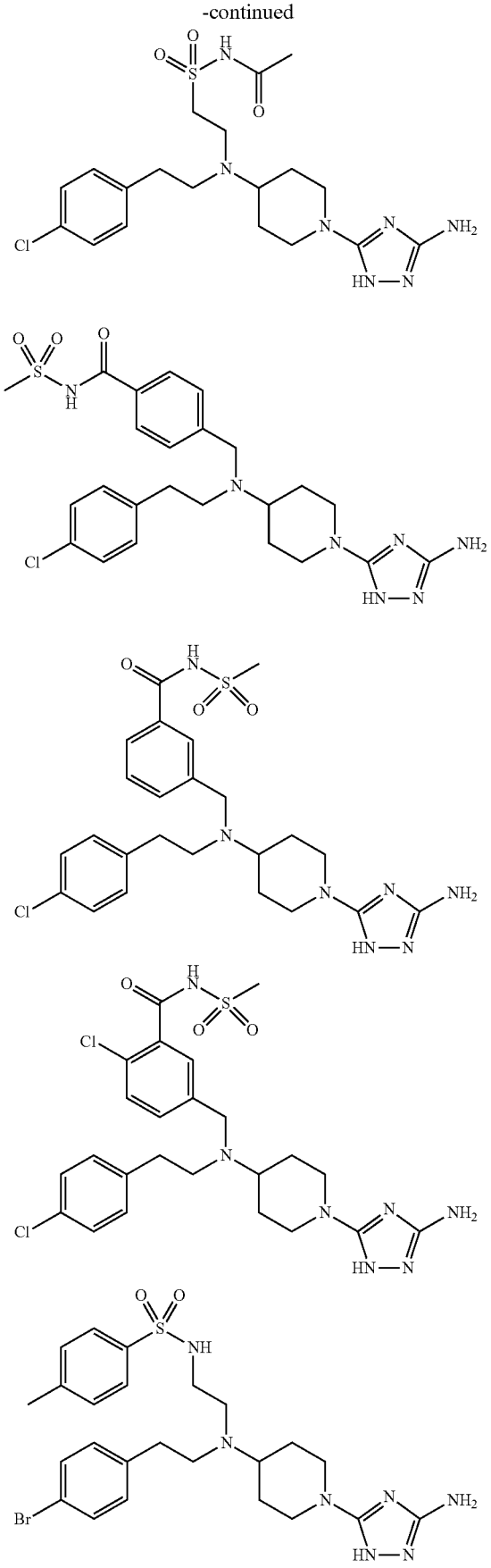

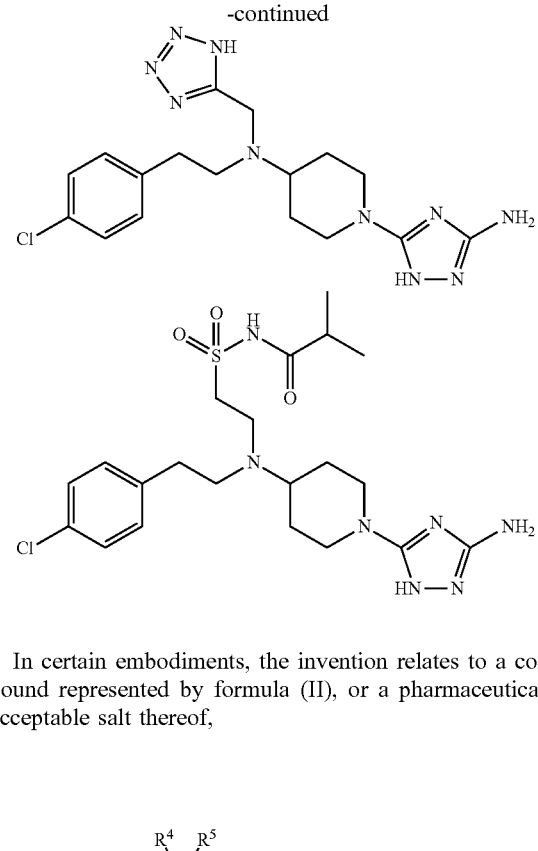

In certain embodiments, the invention relates to a compound represented by formula (II), or a pharmaceutically acceptable salt thereof,

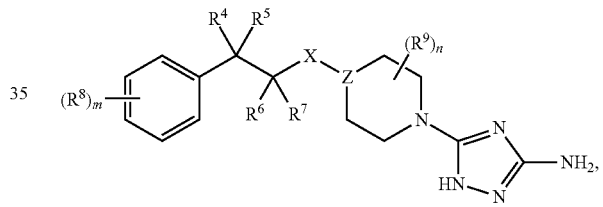

wherein:

X is NH or N(C(R$^1$)(R$^2$)(R$^3$)), and Z is CR$^{10}$; or X is CHR$^{11}$ or C(R$^{11}$)(C(R$^1$)(R$^2$)(R$^3$)), and Z is N;

R$^1$, R$^2$, R$^3$, R$^4$, R$^5$, R$^6$, and R$^7$ are each independently H, (C$_1$-C$_6$)alkyl, aryl(C$_1$-C$_6$)alkyl, or aryl; or R$^2$, taken together with R$^6$ or R$^7$, forms a 5- or 6-membered ring;

R$^8$ is selected from the group consisting of halo, (C$_1$-C$_6$) alkyl, (C$_1$-C$_6$)haloalkyl, and (C$_3$-C$_6$)cycloalkyl;

R$^9$ is selected from the group consisting of Y, aryl substituted by Y, and (C$_1$-C$_6$)alkyl substituted by Y;

Y is —CO$_2$H, —C(O)O(C$_1$-C$_6$)alkyl, —C(O)N(H)OH, —C(O)N(H)CN, —C(O)NH$_2$, —C(O)NH((C$_1$-C$_6$)alkyl), —C(O)N((C$_1$-C$_6$)alkyl)$_2$, —C(O)NH(aryl), —C(O)N(aryl)((C$_1$-C$_6$)alkyl), —C(O)N(aryl)$_2$, —C(O)NH((C$_1$-C$_6$)haloalkyl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)(C$_1$-C$_6$)alkyl, —S(O)$_2$NHC(O)(C$_1$-C$_6$)haloalkyl, —S(O)$_2$NHC(O)aryl, —N(H)S(O)$_2$(C$_1$-C$_6$)alkyl, —N(H)S(O)$_2$aryl, N(H)S(O)$_2$(C$_1$-C$_6$)haloalkyl, —NHC(O)((C$_1$-C$_6$)alkyl), —NHC(O)((C$_1$-C$_6$)haloalkyl), —NHC(O)(aryl), —NHC(O)NH(C$_1$-C$_6$)alkyl, —NHC(O)NHaryl, —C(O)N(H)S(O)$_2$(C$_1$-C$_6$)alkyl, —C(O)N(H)S(O)$_2$aryl, C(O)N(H)S(O)$_2$((C$_1$-C$_6$)haloalkyl), —P(O)(OH)$_2$,

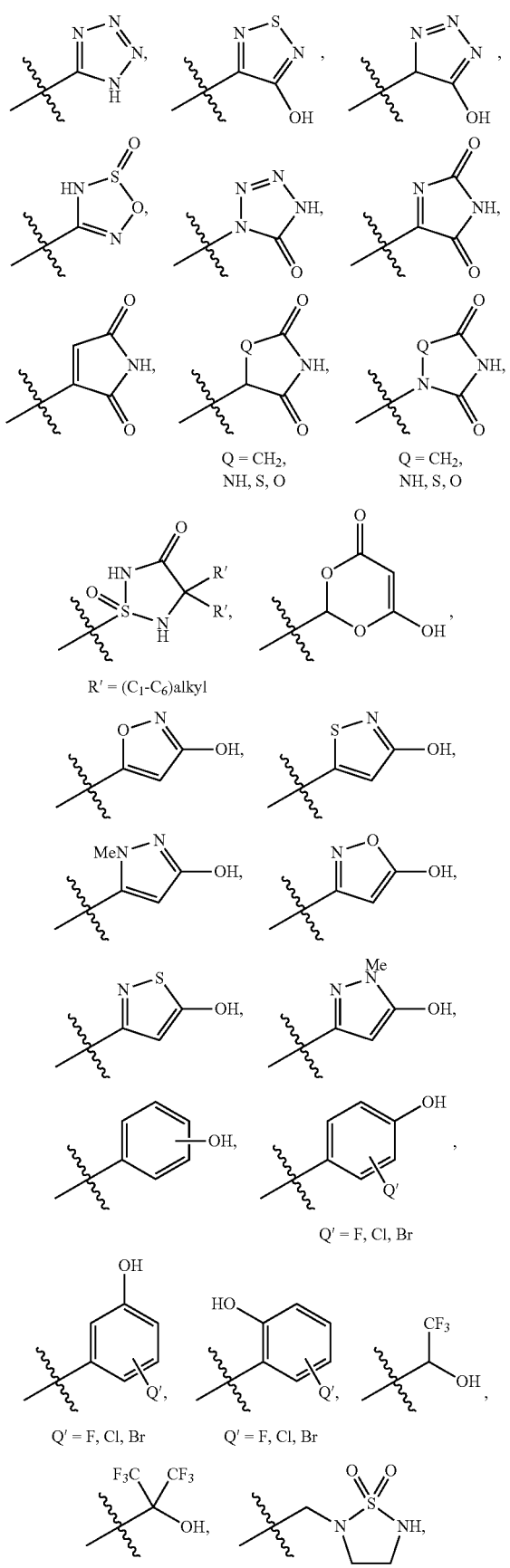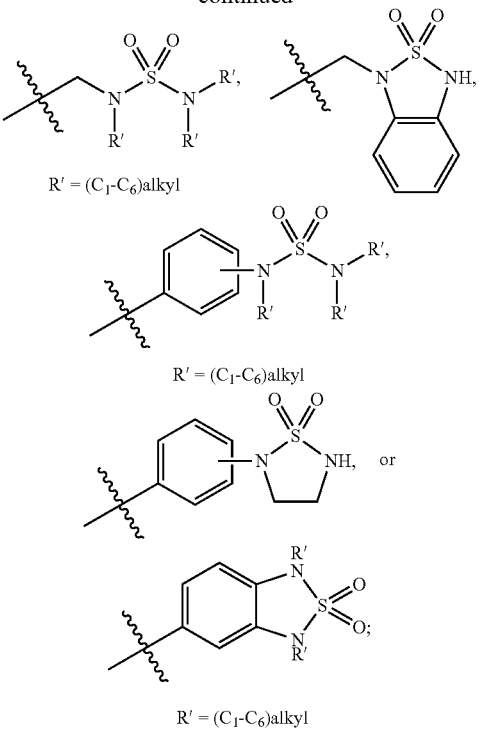

$R^{10}$ and $R^{11}$ are each independently selected from H and $(C_1-C_6)$alkyl;

m is an integer from 0-5; and n is 1 or 2;

further wherein any occurrence of $(C_1-C_6)$alkyl, aryl$(C_1-C_6)$alkyl, aryl, $(C_3-C_6)$cycloalkyl, $(C_1-C_6)$alkoxyl, $(C_1-C_6)$haloalkyl, $(C_1-C_6)$hydroxyalkyl, heteroaryl, or heteroaryl$(C_1-C_6)$alkyl is optionally and independently substituted by one or more substituents selected from the group consisting of halo, $(C_1-C_6)$alkyl, $(C_1-C_6)$haloalkyl, aryl, —$NH_2$, —NH$((C_1-C_6)$alkyl), —N$((C_1-C_6)$alkyl$)_2$, —OH, $(C_3-C_6)$cycloalkyl, $(C_1-C_6)$alkoxyl, $(C_1-C_6)$haloalkoxyl, —SH, —S$((C_1-C_6)$alkyl), $(C_1-C_6)$hydroxyalkyl, and $(C_1-C_6)$alkoxy$(C_1-C_6)$alkyl, —CN, —$CF_3$, —C(O)$NH_2$, —C(O)NH($R^{12}$), —C(O)N($R^{12})_2$, —N(H)C(O)($R^{12}$), —N($R^{12}$)C(O)($R^{12}$), —S(O)$_2NH_2$, —S(O)$_2$NH($R^{12}$), —S(O)$_2$N($R^{12})_2$, —N(H)S(O)$_2$($R^{12}$), —N($R^{12}$)S(O)$_2$($R^{12}$), —NHC(O)$NH_2$, —NHC(O)NH($R^{12}$), and —NHC(O)N($R^{12})_2$; and each occurrence of $R^{12}$ is independently selected from the group consisting of $(C_1-C_6)$alkyl), aryl, and aryl$(C_1-C_6)$alkyl.

In certain embodiments, $R^9$ is Y.

In certain embodiments, $R^9$ is aryl substituted by Y.

In certain embodiments, $R^9$ is $(C_1-C_6)$alkyl substituted by Y.

In certain embodiments, the invention relates to a compound of formula (II), wherein Y is —$CO_2H$, —C(O)$NH_2$, —C(O)NH$(C_1-C_6)$alkyl, —C(O)N$((C_1-C_6)$alkyl$)_2$, —C(O)NH(aryl), C(O)N(aryl)$((C_1-C_6)$alkyl), C(O)N(aryl)$_2$, —C(O)NH$((C_1-C_6)$haloalkyl), —S(O)$_2NH_2$, —S(O)$_2$NH$((C_1-C_6)$alkyl), —S(O)$_2$NH$((C_1-C_6)$haloalkyl), —S(O)$_2$NH(aryl), —S(O)$_2$NHC(O)$(C_1-C_6)$alkyl, —S(O)$_2$NHC(O)$(C_1-C_6)$haloalkyl, —S(O)$_2$NHC(O)aryl, —N(H)S(O)$_2(C_1-C_6)$alkyl, —N(H)S(O)$_2$aryl, —N(H)S(O)$_2(C_1-C_6)$haloalkyl, —NHC(O)$((C_1-C_6)$alkyl), —NHC(O)$((C_1-C_6)$haloalkyl), —NHC(O)(aryl), —NHC(O)NH$(C_1-C_6)$alkyl, —NHC(O)

NHaryl, —C(O)N(H)S(O)$_2$(C$_1$-C$_6$)alkyl, —C(O)N(H)S(O)$_2$aryl, C(O)N(H)S(O)$_2$((C$_1$-C$_6$)haloalkyl), or 1H-tetrazolyl.

In certain embodiments, the invention relates to a compound of formula (II), wherein R$^9$ is selected from the group consisting of:

CO$_2$H;

C(O)NH$_2$;

C(O)NH((C$_1$-C$_6$)alkyl);

C(O)NH(aryl);

1H-tetrazolyl;

aryl substituted by —CO$_2$H, —C(O)NH$_2$, —C(O)NH(C$_1$-C$_6$)alkyl, —C(O)NH(aryl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)(C$_1$-C$_6$)alkyl, —S(O)$_2$NHC(O)(C$_1$-C$_6$)haloalkyl, —S(O)$_2$NHC(O)aryl, —N(H)S(O)$_2$(C$_1$-C$_6$)alkyl, —N(H)S(O)$_2$aryl, —C(O)N(H)S(O)$_2$(C$_1$-C$_6$)alkyl, —C(O)N(H)S(O)$_2$aryl, or 1H-tetrazolyl; and (C$_1$-C$_6$)alkyl substituted by CO$_2$H, —NHC(O)(C$_1$-C$_6$)alkyl, —NHC(O)(C$_1$-C$_6$)haloalkyl, —NHC(O)aryl, —NHC(O)NH(C$_1$-C$_6$)alkyl, —NHC(O)NHaryl, —N(H)S(O)$_2$(C$_1$-C$_6$)alkyl, —N(H)S(O)$_2$aryl, —S(O)$_2$NH$_2$, —S(O)$_2$NH(C$_1$-C$_6$)alkyl, —S(O)$_2$NH(C$_1$-C$_6$)haloalkyl, —S(O)$_2$NHaryl, —S(O)$_2$NHC(O)(C$_1$-C$_6$)alkyl, or —S(O)$_2$NHC(O)aryl.

In certain embodiments, there is one occurrence of R$^9$, i.e., n is 1.

In certain embodiments, X is NH; and Z is CH.

In certain alternative embodiments, X is N(C(R$^1$)(R$^2$)(R$^3$)); and Z is CH. In certain such embodiments, R$^2$ and R$^3$ are both H. In certain such embodiments, R$^1$ is H or (C$_1$-C$_6$)alkyl.

In certain embodiments, R$^2$, taken together with R$^6$ or R$^7$, forms a 5- or 6-membered ring, preferably, a 6-membered ring.

In other embodiments, X is CH$_2$; and Z is N.

In certain embodiments, R$^8$ is selected from the group consisting of halo, (C$_1$-C$_6$)haloalkyl, and (C$_1$-C$_6$)alkyl. In certain embodiments, R$^8$ is halo.

In certain embodiments, there is one occurrence of R$^8$ on the aromatic ring, i.e., m is 1.

In certain embodiments, R$^4$, R$^5$, R$^6$, and R$^7$ are each independently selected from the group consisting of H and (C$_1$-C$_6$)alkyl. In certain embodiments, R$^4$, R$^5$, R$^6$, and R$^7$ are each H.

In certain embodiments, the invention relates to a compound represented by formula (III), or a pharmaceutically acceptable salt thereof,

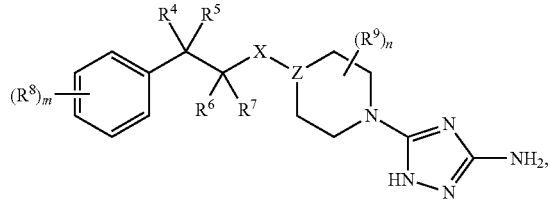

wherein:

X is NH or N(C(R$^1$)(R$^2$)(R$^3$)), and Z is CR$^{19}$; or X is CHR$^{11}$ or C(R$^{11}$)(C(R$^1$)(R$^2$)(R$^3$)), and Z is N;

R$^1$, R$^2$, R$^3$, R$^4$, R$^5$, and R$^7$ are each independently H, (C$_1$-C$_6$)alkyl, aryl(C$_1$-C$_6$)alkyl, or aryl; or R$^1$ or R$^2$, taken together with or R$^7$, forms a 5- or 6-membered ring;

R$^6$ is selected from the group consisting of Y, aryl substituted by Y, and (C$_1$-C$_6$)alkyl substituted by Y;

Y is —CO$_2$H, —C(O)O(C$_1$-C$_6$)alkyl, —C(O)N(H)OH, —C(O)N(H)CN, —C(O)NH$_2$, —C(O)NH((C$_1$-C$_6$)alkyl), —C(O)N((C$_1$-C$_6$)alkyl)$_2$, —C(O)NH(aryl), —C(O)N(aryl)((C$_1$-C$_6$)alkyl), —C(O)N(aryl)$_2$, —C(O)NH((C$_1$-C$_6$)haloalkyl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)(C$_1$-C$_6$)alkyl, —S(O)$_2$NHC(O)(C$_1$-C$_6$)haloalkyl, —S(O)$_2$NHC(O)aryl, —N(H)S(O)$_2$(C$_1$-C$_6$)alkyl, —N(H)S(O)$_2$aryl, N(H)S(O)$_2$(C$_1$-C$_6$)haloalkyl, —NHC(O)((C$_1$-C$_6$)alkyl), —NHC(O)((C$_1$-C$_6$)haloalkyl), —NHC(O)(aryl), —NHC(O)NH(C$_1$-C$_6$)alkyl, —NHC(O)NHaryl, —C(O)N(H)S(O)$_2$(C$_1$-C$_6$)alkyl, —C(O)N(H)S(O)$_2$aryl, C(O)N(H)S(O)$_2$((C$_1$-C$_6$)haloalkyl), —P(O)(OH)$_2$,

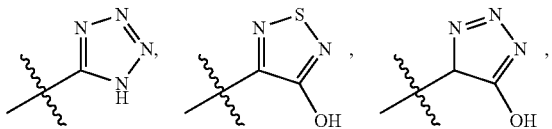

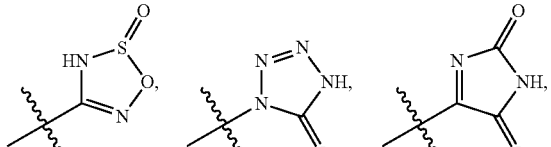

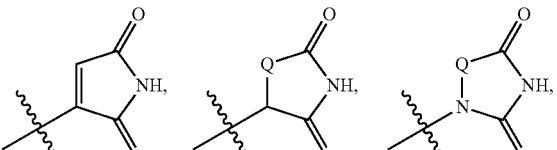

Q = CH$_2$, NH, S, O

Q = CH$_2$, NH, S, O

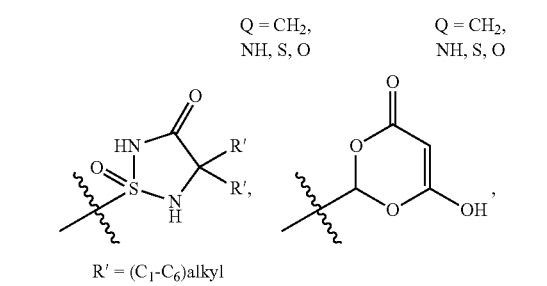

R' = (C$_1$-C$_6$)alkyl

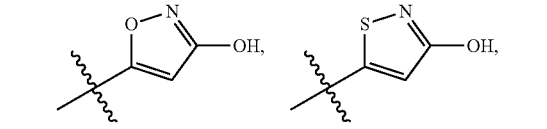

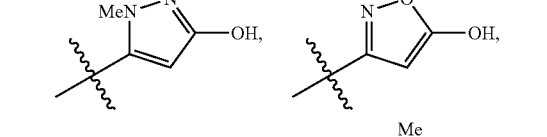

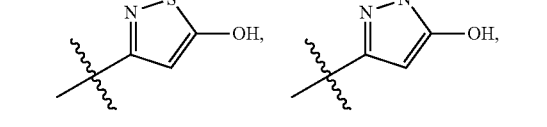

-continued

Q' = F, Cl, Br

Q' = F, Cl, Br

R' = (C₁-C₆)alkyl

R' = (C₁-C₆)alkyl

R' = (C₁-C₆)alkyl

R' = (C₁-C₆)alkyl $R^8$ is selected from the group consisting of halo, $(C_1-C_6)$ alkyl, $(C_1-C_6)$haloalkyl, and $(C_3-C_6)$cycloalkyl;

$R^9$ is selected from the group consisting of OH, $(C_1-C_6)$ alkyl, $(C_3-C_6)$cycloalkyl, aryl$(C_1-C_6)$alkyl, aryl, $(C_1-C_6)$ alkoxyl, $(C_1-C_6)$haloalkyl, $(C_1-C_6)$hydroxyalkyl, heteroaryl, and heteroaryl$(C_1-C_6)$alkyl;

$R^{10}$ and $R^{11}$ are each independently selected from H and $(C_1-C_6)$alkyl;

m is an integer from 0-5; and n is an integer from 0-2;

further wherein any occurrence of $(C_1-C_6)$alkyl, aryl$(C_1-C_6)$ alkyl, aryl, $(C_3-C_6)$cycloalkyl, $(C_1-C_6)$alkoxyl, $(C_1-C_6)$ haloalkyl, $(C_1-C_6)$hydroxyalkyl, heteroaryl, or heteroaryl $(C_1-C_6)$alkyl is optionally and independently substituted by one or more substituents selected from the group consisting of halo, $(C_1-C_6)$alkyl, $(C_1-C_6)$haloalkyl, aryl, —NH₂, —NH$((C_1-C_6)$alkyl), —N$((C_1-C_6)$alkyl)₂, —OH, $(C_3-C_6)$cycloalkyl, $(C_1-C_6)$alkoxyl, $(C_1-C_6)$haloalkoxyl, —SH, —S$((C_1-C_6)$alkyl), $(C_1-C_6)$hydroxyalkyl, and $(C_1-C_6)$alkoxy$(C_1-C_6)$alkyl, —CN, —CF₃, —C(O)NH₂, —C(O)NH$(R^{12})$, —C(O)N$(R^{12})_2$, —N(H)C(O)$(R^{12})$, —N$(R^{12})$C(O)$(R^{12})$, —S(O)₂NH₂, —S(O)₂NH$(R^{12})$, —S(O)₂N$(R^{12})_2$, —N(H)S(O)₂$(R^{12})$, —N$(R^{12})$S(O)₂ $(R^{12})$, —NHC(O)NH₂, —NHC(O)NH$(R^{12})$, and —NHC(O)N$(R^{12})_2$; and each occurrence of $R^{12}$ is independently selected from the group consisting of $(C_1-C_6)$alkyl), aryl, and aryl$(C_1-C_6)$ alkyl.

In certain embodiments, $R^6$ is Y.

In certain embodiments, $R^6$ is aryl substituted by Y.

In certain embodiments, $R^6$ is $(C_1-C_6)$alkyl substituted by Y.

In certain embodiments, the invention relates to a compound of formula (III), wherein Y is —CO₂H, —C(O)NH₂, —C(O)NH$(C_1-C_6)$alkyl, —C(O)N$((C_1-C_6)$alkyl)₂, —C(O) NH(aryl), C(O)N(aryl)$((C_1-C_6)$alkyl), C(O)N(aryl)₂, —C(O)NH$((C_1-C_6)$haloalkyl), —S(O)₂NH₂, —S(O)₂NH $((C_1-C_6)$alkyl), —S(O)₂NH$((C_1-C_6)$haloalkyl), —S(O)₂NH (aryl), —S(O)₂NHC(O)$(C_1-C_6)$alkyl, —S(O)₂NHC(O)$(C_1-C_6)$haloalkyl, —S(O)₂NHC(O)aryl, —N(H)S(O)₂$(C_1-C_6)$ alkyl, —N(H)S(O)₂aryl, —N(H)S(O)₂$(C_1-C_6)$haloalkyl, —NHC(O)$((C_1-C_6)$alkyl), —NHC(O)$((C_1-C_6)$haloalkyl), —NHC(O)(aryl), —NHC(O)NH$(C_1-C_6)$alkyl, —NHC(O) NHaryl, —C(O)N(H)S(O)₂$(C_1-C_6)$alkyl, —C(O)N(H) S(O)₂aryl, C(O)N(H)S(O)₂$((C_1-C_6)$haloalkyl), or 1H-tetrazolyl.

In certain embodiments, the invention relates to a compound of formula (III), wherein $R^6$ is selected from the group consisting of:

CO₂H;

C(O)NH₂;

C(O)NH$((C_1-C_6)$alkyl);

C(O)NH(aryl);

1H-tetrazolyl;

aryl substituted by —CO₂H, —C(O)NH₂, —C(O)NH$(C_1-C_6)$alkyl, —C(O)NH(aryl), —S(O)₂NH₂, —S(O)₂NH $((C_1-C_6)$alkyl), —S(O)₂NH$((C_1-C_6)$haloalkyl), —S(O)₂NH(aryl), —S(O)₂NHC(O)$(C_1-C_6)$alkyl, —S(O)₂NHC(O)$(C_1-C_6)$haloalkyl, —S(O)₂NHC(O) aryl, —N(H)S(O)₂$(C_1-C_6)$alkyl, —N(H)(SO₂)aryl, —C(O)N(H)S(O)₂$(C_1-C_6)$alkyl, —C(O)N(H) S(O)₂aryl, or 1H-tetrazolyl; and $(C_1-C_6)$alkyl substituted by CO₂H, —NHC(O)$(C_1-C_6)$ alkyl, —NHC(O)$(C_1-C_6)$haloalkyl, —NHC(O)aryl, —NHC(O)NH$(C_1-C_6)$alkyl, —NHC(O)NHaryl, —N(H)S(O)₂$(C_1-C_6)$alkyl, —N(H)S(O)₂aryl, —S(O)₂NH₂, —S(O)₂NH$(C_1-C_6)$alkyl, —S(O)₂NH $(C_1-C_6)$haloalkyl, —S(O)₂NHaryl, —S(O)₂NHC(O) $(C_1-C_6)$alkyl, or —S(O)₂NHC(O)aryl.

In certain embodiments, n is 1.

In certain embodiments, X is NH; and Z is CH.

In certain alternative embodiments, X is N(C($R^1$)($R^2$) ($R^3$)); and Z is CH. In certain such embodiments, $R^2$ and $R^3$ are both H. In certain such embodiments, $R^1$ is H or $(C_1-C_6)$alkyl.

In certain embodiments, or $R^1$ or $R^2$, taken together with or $R^7$, forms a 5- or 6-membered ring, preferably a 6-membered ring.

In other embodiments, X is CH₂; and Z is N.

In certain embodiments, $R^8$ is selected from the group consisting of halo, $(C_1-C_6)$haloalkyl, and $(C_1-C_6)$alkyl. In certain embodiments, $R^8$ is halo.

In certain embodiments, there is one occurrence of $R^8$ on the aromatic ring, i.e., m is 1.

In certain embodiments, $R^4$, $R^5$, and $R^7$ are each independently selected from the group consisting of H and $(C_1-C_6)$alkyl. In certain embodiments, $R^4$, $R^5$, and $R^7$ are each H.

In certain embodiments, $R^9$ is selected from the group consisting of $(C_1-C_6)$alkyl, $(C_3-C_6)$cycloalkyl, and aryl$(C_1-C_6)$alkyl.

In certain embodiments, n is 0.

The compounds described herein are useful in treating inflammatory diseases such as esophageal eosinophilic inflammation, keratoconjunctivitis, seasonal allergic conjunctivitis, dry eye syndrome, or chronic rhinosinusitis with nasal polyps. The compounds can be used in treating diseases caused by infectious agents, such as fungi, worms and parasites. The compounds can be used in treating chronic obstructive pulmonary disease (COPD) or autoimmune diseases including but not restricted to inflammatory bowel disease or rheumatoid arthritis.

Pharmaceutical Compositions of the Invention

Another aspect of the invention provides a pharmaceutical composition of a compound of the invention (e.g., a compound of any of formulae (I), (II), or (III)), and a pharmaceutically acceptable carrier.

The exact nature of the carrier, or, for example excipient or diluent, will depend upon the desired use for the composition, and may be suitable or acceptable for veterinary use and/or suitable or acceptable for human use. The composition may optionally include one or more additional compounds, including one or more additional therapeutic agents.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents that may be administered with the compounds of the invention include steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.0001 milligrams/kg per day, 0.001 milligrams/kg per day, or 0.01 milligrams/kg per day to about 100 milligrams/kg per day or 1000 milligrams/kg per day. It is expected that oral doses in the range of 0.5 to 50 milligrams/kg, in one or several administrations per day, will yield the desired results. Dosage may be adjusted appropriately to achieve desired drug levels sufficient to achieve or maintain a desired therapeutic effect, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds. The compounds may be administered once per week, several times per week (e.g., every other day), once per day or multiple times per day, depending upon, among other things, the mode of administration, the specific indication being treated and the judgment of the prescribing physician.

In one embodiment, intravenous administration of a compound of the invention may typically be from 0.1 mg/kg/day to 20 mg/kg/day.

Determination of an effective dosage of a compound for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions comprising the compound of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, buccal, nasal, rectal, vaginal, ocular, topical, intravenous, intramuscular, intraperitoneal, subcutaneous, transdermal, direct injection (for example, into an abscess), mucosal, inhalation, and insufflation.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, lozenges, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, binding agents, fillers, lubricants, disintegrants, and wetting agents. Suitable fillers include sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) ($\alpha$1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as sterile suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, buffer, dextrose solution, before use. To this end, the active compound may be dried by any art-known technique, such as lyophilization, and reconstituted prior to use.

The compounds may also be formulated in rectal or vaginal compositions such as suppositories or retention enemas, e.g., containing conventional suppository bases such as cocoa butter or other glycerides.

For transmucosal administration, penetrants appropriate to the barrier to be permeated are used in the formulation. Such penetrants are known in the art.

For ocular administration, the compound(s) may be formulated as a solution, emulsion, suspension, etc. suitable for administration to the eye. A variety of vehicles suitable for administering compounds to the eye are known in the art.

In addition to the formulations described above, for prolonged delivery, the compounds may also be formulated as a depot preparation for administration by, for example, implantation or intramuscular injection. Such long acting formulations may be formulated with suitable polymeric or hydrophobic materials (for example as an emulsion in an acceptable oil) or ion exchange resins, or as sparingly soluble derivatives, for example, as a sparingly soluble salt. Alternatively, transdermal delivery systems manufactured as an adhesive disc or patch which slowly releases the compound for percutaneous absorption may be used. To this end, permeation enhancers may be used to facilitate transdermal penetration of the compound.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Typically, such salts are more soluble in aqueous solutions than the corresponding free acids and bases, but salts having lower solubility than the corresponding free acids and bases may also be formed.

The compounds may alternatively be formulated in the pharmaceutical composition per se, or in the form of a hydrate, solvate, or N-oxide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

Methods of the Invention

Another aspect of the invention is a method for treating asthma, comprising administering to a subject in need thereof a therapeutically effective amount of a compound of the invention, for example a compound of any one of formulae (I), (II), and (III).

The invention also provides methods for treating a reaction caused by an allergen, comprising administering to a subject in need thereof a therapeutically effective amount of a compound of the invention, for example a compound of any one of formulae (I), (II), and (III).

In certain embodiments, the reaction caused by an allergen is allergic rhinitis or atopic dermatitis.

In certain embodiments, the reaction caused by an allergen is characterized by the occurrence of one or more symptoms, which can include red eyes, itchiness, runny nose, eczema, impaired hearing, hives, an asthma attack, increased mucus production in the lungs, coughing, wheezing, and shortness of breath.

In certain embodiments, the allergen is mold, mammal dander, pollen, spores, fungus, dust mites, insects (e.g., cockroaches), or a chemical (e.g., an isocyanate).

In certain embodiments, the invention provides methods for treating a fungal or parasitic infection, comprising administering to a subject in need thereof a therapeutically effective amount of a compound of the invention (e.g., a compound of any one of formulae (I), (II), and (III)). In certain embodiments, the infections treated in the methods of the invention include infections caused by fungi, worms, or parasites.

In another aspect, the invention provides methods for assessing the efficacy of an agent for treating asthma in a subject, comprising the steps of:

a) detecting in a subject sample collected at a first point in time, the expression level of acidic mammalian chitinase protein;

b) repeating step a) at one or more subsequent points in time after administration of the agent; and c) comparing expression level of acidic mammalian chitinase protein detected in step a) with the expression level(s) detected in step b), wherein a higher expression level of acidic mammalian chitinase protein at the first point in time relative to at least one subsequent point in time indicates that the agent is efficacious in treating asthma.

In certain embodiments, an agent identified by such a method is efficacious in treating asthma, hay fever, allergic rhinitis, atopic dermatitis, allergic reactions, or a disorder associated with Th-2.

Alternatively, the efficacy of an agent for treating asthma or an allergic reaction can be assessed via measuring the expression level of an inflammatory mediator such as IL-13, IL-5, IL-4, eotaxin, IgE, or measuring the amount of inflammatory cells such as eosinophils, neutrophils, or lymphocytes in brocho-alveolar washings, sputum, or tissues obtained from a mammal. In certain such embodiments, the expression level can be measured prior to and after administration of an agent. When the expression level of the inflammatory mediator or the level of inflammatory cells decreases after administration of an agent, such an agent is efficacious in treating asthma, hay fever, allergic rhinitis, atopic dermatitis, allergic reactions, or a disorder associated with Th-2.

Another aspect of the invention provides methods of identifying an agent for treating asthma, comprising:

a) contacting a sample comprising acidic mammalian chitinase protein with the agent; and b) determining the ability of the agent to inhibit activity of acidic mammalian chitinase protein, wherein decreased activity of acidic mammalian chitinase protein identifies an agent for treating asthma.

In certain embodiments, the activity of acidic mammalian chitinase protein is assessed by fluorescence assay using a reagent that is hydrolyzed by acidic mammalian chitinase protein. In certain embodiments, the reagent is 4-methylumbelliferyl B-D-N,N'-diacetylchitobioside hydrate.

EXAMPLES

The present invention is further illustrated by the following examples, which in no way should be construed as limiting the scope of the claimed invention.

Materials and Methods
Methods of Preparation and Characterization

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below.

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, *March's Advanced Organic Chemistry*: Reactions, Mechanisms, and Structure, Fifth Edition, Wiley-lnterscience, 2001; or Vogel, *A Textbook of Practical Organic Chemistry, Including Qualitative Organic Analysis*, Fourth Edition, New York: Longman, 1978).

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "*Protective Groups in Organic Chemistry*," Plenum Press, London and New York 1973, in T. W. Greene and P. G. M. Wuts, "*Protective Groups in Organic Synthesis*," Third edition, Wiley, New York 1999, in "*The Peptides*;" Volume 3 (editors: E. Gross and J. Meienhofer), Academic Press, London and New York 1981, in "*Methoden der organischen Chemie*," Houben-Weyl, 4th edition, Vol. 15/1, Georg Thieme Verlag, Stuttgart 1974, in H.-D. Jakubke and H. Jescheit, "*Aminosauren, Peptide, Proteine*," Verlag Chemie, Weinheim, Deerfield Beach, and Basel 1982, and/or in Jochen Lehmann, "*Chemie der Kohlenhydrate: Monosaccharide and Derivate*," Georg Thieme Verlag, Stuttgart 1974. The protecting groups may be removed at a convenient subsequent stage using methods known from the art. The disclosures of all articles and references mentioned in this application, including patents, are incorporated herein by reference in their entirety.

Representative synthetic procedures for the preparation of compounds of the invention are outlined below. Substituents carry the same meaning as defined above, unless otherwise noted.

Starting materials can be obtained from commercial sources or prepared by well-established literature methods known to those skilled in the art.

All solvents, substrates and reagents that were commercially available were used without further purification. TLC analysis was performed using pre-coated glass plates (0.2±0.03 mm thickness, GF-254, particle size 0.01-0.04 mm) from Fluorochem Ltd, UK. Column chromatography was performed using high-purity grade silica gel (pore size 60 Å, 220-440 mesh particle size, 35-75 μm particle size) from Fluka.

$^1$H and $^{13}$C NMR spectra were recorded on a 500 MHz AVANCE DRX500 or 600 MHz AVANCE DRX600 Bruker NMR spectrometers.

$^{19}$F NMR spectra were recorded on a 200 MHz AVANCE Bruker NMR spectrometer.

All spectra were recorded in appropriate deuterated solvents (CDCl$_3$, DMSO-d$_6$, D$_2$O, CD$_3$OD, etc.) that were commercially available.

Resonances are given in parts per million relative to tetramethylsilane. Data are reported as follows: chemical shift, multiplicity (s=singlet, d=doublet, t=triplet, m=multiplet, bs=broad singlet), coupling constants (Hz) and integration.

ESI-MS spectra were obtained on a Waters Alliance 2695 separation module with a PDA 1996 UV detector and Waters Micromass ZQ 2000 mass detector equipped with Kinetex 2.1/50 mm, 2.6 μm C18 column eluted with 0.3 mL/min flow of 3-100% gradient (over 6 min) of acetonitrile in water.

Human AMCase Activity Assay

An enzymatic assay with recombinant human AMCase was used in order to establish inhibitory activity of the compounds (Boot et al., 2001, *JBC*: 276). The assay was run in the 96-well plate format, each reaction in the total volume of 100 μL. 4-Methylumbelliferyl B-D-N,N'-diacetylchitobioside hydrate was used as a substrate for the enzyme. Upon hydrolysis by AMCase, the substrate releases 4-methylumbelliferyl (4MU) that, when ionized in basic pH, emits fluorescence at 460 nm.

Briefly, 40 μL of a substrate was added to each well, followed by 10 μL of compound dilution and 50 μL of hAMCase recombinant enzyme solution. The reaction was carried out in citrate buffer, pH 5.2, in the dark, at 37° C. for 60 minutes with shaking After that time the reaction was stopped by adding 195 μl of Stop Buffer (pH 10.5) to each well. The fluorescence of the reaction product was measured in Perkin Elmer Envision fluorescent plate reader at an excitation wavelength of 355 nm.

The IC$_{50}$ values (noted for compounds below as "activity") were calculated using GraphPad Prism and divided into the following groups: Activity hAMCase IC$_{50}$: A=1-10 nM; B=10-100 nM; C=0.1-1 μM; D=1-10 μM; E>10 μM.

Example 1

General Synthetic Procedures

Procedure 1:

Reductive Amination—preparation of compounds of the general formula:

wherein: X=Cl or Br; R is an alkyl, substituted by a polar functional group (e.g., carboxylic acid, ester, sulfonamide, nitrile, tetrazole etc.)

Procedure 1A

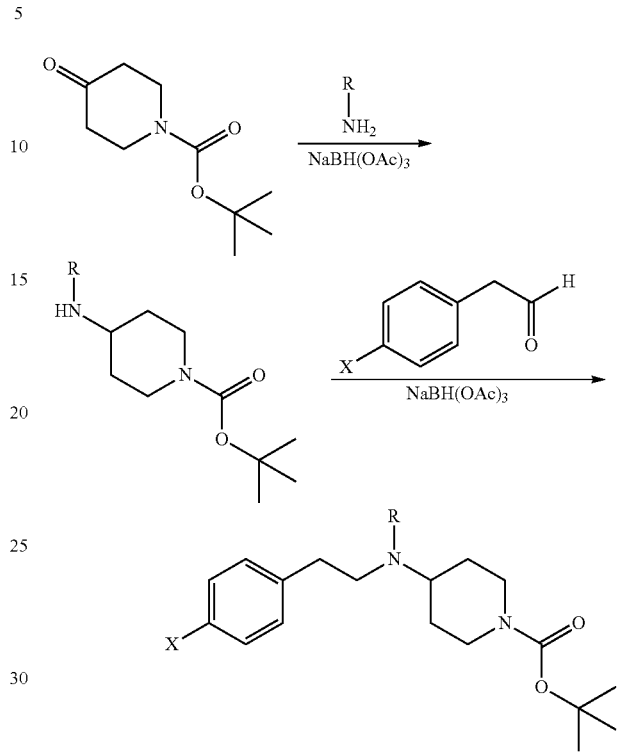

To the solution of N-Boc-piperid-4-one in dichloroethane (DCE) (2 mL/mmol) or in DCE/AcOH (10:1 v/v, 2 mL/mmol), a primary alkyl amine R—NH$_2$ (1 equiv), substituted by a polar functionality on the alkyl group (e.g., carboxylic acid, ester, sulfonamide, nitrile, tetrazole, etc.), is added, followed by addition of NaBH(OAc)$_3$ (2 equiv). The reaction mixture is stirred for an appropriate period of time (typically 1-15 hours) at room temperature, and (4-(halo)-phenyl)acetaldehyde (1.5 equiv) is then added, followed by another portion of NaBH(OAc)$_3$ (2 equiv). The reaction mixture is stirred for another 5 hours at room temperature after which time it is partitioned between 5% NaHCO$_3$ and EtOAc (10 mL/mmol). The organic layer is washed once again with 5% NaHCO$_3$, then brine (2×) and then is dried over MgSO$_4$. After filtration of the drying agent and stripping the solvent, the desired product is purified either by crystallization or by flash column chromatography over silica gel.

Procedure 1B

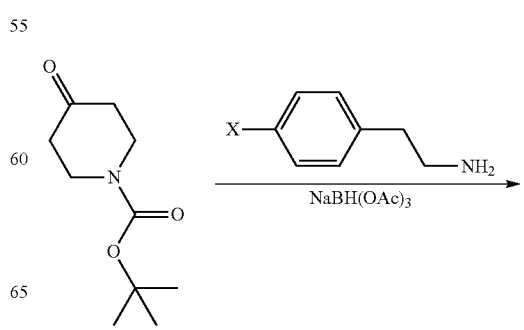

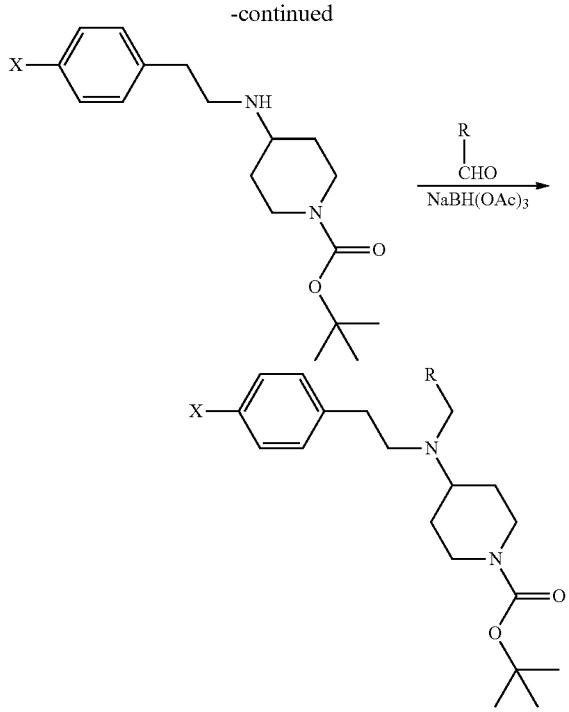

To the solution of N-Boc-piperid-4-one in DCE (2 mL/mmol), 2-(4-(halo)-phenyl)ethylamine (1 equiv) is added followed by addition of NaBH(OAc)$_3$ (2 equiv). The reaction mixture is stirred for an appropriate period of time (typically 1-15 hours) at room temperature, after which time the aldehyde (1.5 equiv) containing a polar functionality (e.g., carboxylic acid, ester, sulfonamide, nitrile, tetrazole, etc.) is added, followed by addition of NaBH(OAc)$_3$ (2 equiv). The reaction mixture is stirred for another 5 hours at room temperature after which time it is partitioned between 5% NaHCO$_3$ and EtOAc (10 mL/mmol). The organic layer is washed once again with 5% NaHCO$_3$, then brine (2×) and then is dried over MgSO$_4$. After filtration of the drying agent and stripping the solvent, the desired product is purified either by crystallization or flash column chromatography over silica gel.

Procedure 2:

Deprotection—Preparation of compounds of the general formula:

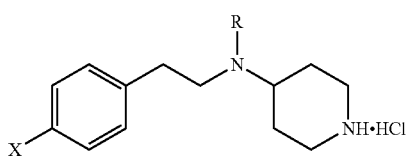

The product of reductive amination described in Procedure 1 is treated with a 4 N solution of HCl (4 mL/mmol of starting material) in appropriate organic solvent (e.g., EtOAc, 1,4-dioxane, MeOH, DCM, etc.) for the time necessary for complete consumption of the starting material (typically 30 min 2 hrs). The volatiles are then removed in vacuo providing the desired compound in the form of its hydrochloride salt that is directly taken to the next step without any further purification.

Procedure 3:

Preparation of the triazolyl compounds of the general formula:

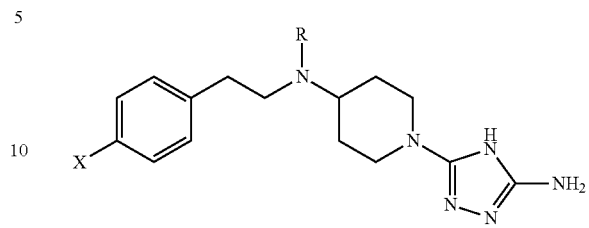

The product of the protecting group removal described in Procedure 2, anhydrous K$_2$CO$_3$ (2 equiv) and S,S'-dimethyl-N-cyano-dithioiminocarbonate (1.2 equiv) are added to acetonitrile (2 mL/mmol of starting material) and the reaction is refluxed for 1-7 hours (monitoring by TLC). Hydrazine monohydrate (3-5 equiv) is then added and the mixture is further refluxed for another 2-5 hours after which time it is cooled to room temperature and solids are filtered off. The filtrate is concentrated in vacuo and the crude product is purified either by crystallization from appropriate solvent or chromatography over regular silica gel or a reversed phase C-18 bed.

Example 2

2-(((1-(3-amino-1H-1,2,4-triazol-5-yl)piperidin-4-yl)(4-chlorophenethyl)amino-)methyl)benzoic acid

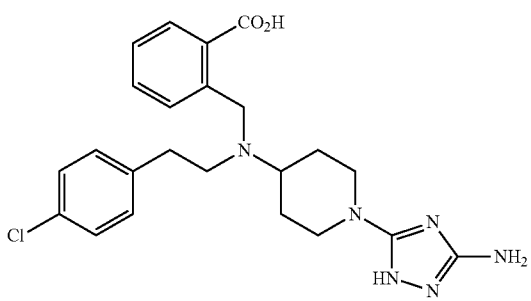 [SMILES: Nc1n[nH]c(N2CCC(N(CCc3ccc(Cl)cc3)Cc3ccccc3C(=O)O)CC2)n1]

Step 1: tert-butyl 4-((4-chlorophenethyl)(2-(methoxycarbonyl)benzyl)amino)piperidine-1-carboxylate

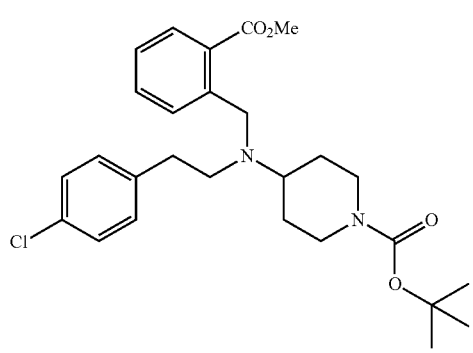 [SMILES: COC(=O)c1ccccc1CN(CCc1ccc(Cl)cc1)C1CCN(C(=O)OC(C)(C)C)CC1]

The title compound was obtained in a manner described in Procedure 1B from N-Boc-piperid-4-one, 2-(4-chlorophenyl)ethylamine, and methyl 2-formylbenzoate. ESI MS for $C_{27}H_{35}ClN_2O_4$: calculated 487.04. found 487.3/489.3 (M+1), 485.3/487.3 (M−1).

Step 2: methyl 2-(((4-chlorophenethyl)(piperidin-4-yl)amino)methyl)benzoate hydrochloride

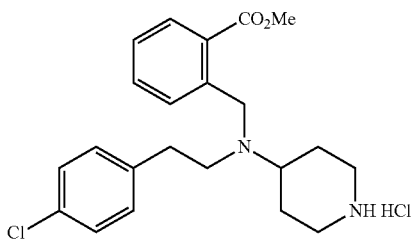

tert-Butyl 4-((4-chlorophenethyl)(2-(methoxycarbonyl)benzyl)amino)piperidine-1-carboxylate obtained in Step 1 was subjected to the deprotection reaction as described in Procedure 2 (4 N HCl in AcOEt).

Step 3: Methyl 2-(((1-(5-amino-4H-1,2,4-triazol-3-yl)piperidin-4-yl)(4-chlorophenethyl)amino)-methyl)benzoate

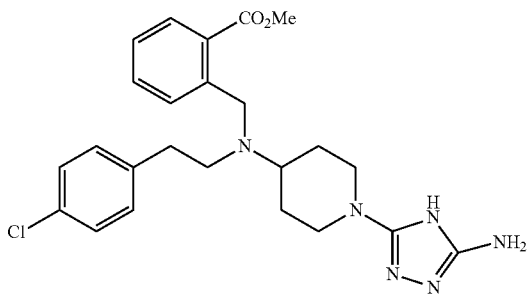 [SMILES: COC(=O)c1ccccc1CN(CCc1ccc(Cl)cc1)C1CCN(c2nnc(N)[nH]2)CC1]

Methyl 2-(((4-chlorophenethyl)(piperidin-4-yl)amino)methyl)benzoate hydrochloride obtained in Step 2 was reacted with $K_2CO_3$ and S,S'-dimethyl-N-cyano-dithioiminocarbonate, followed by the cyclization of the intermediate (N-cyanopiperazine-1-carbimidothioate) with hydrazine monohydrate in a manner described in Procedure 3. ESI MS for $C_{24}H_{29}ClN_6O_2$: calculated 468.99. found 469.4/471.4 (M+1), 467.3/469.3 (M−1).

Step 4: 2-(((1-(3-amino-1H-1,2,4-triazol-5-yl)piperidin-4-yl)(4-chlorophenethyl)amino)methyl) benzoic acid Methyl 2-(((1-(5-amino-4H-1,2,4-triazol-3-yl)piperidin-4-yl)(4-chlorophenethyl)amino)-methyl)benzoate obtained in Step 3 was dissolved in methanol (10 mL) and 3 mL of 1 N NaOH (aq) was added. The reaction mixture was stirred for 5 hours at room temperature after which time the starting material was no longer present. pH of the reaction mixture was brought to 7 by means of careful addition of 1 N HCl and the solvents were stripped off. The solid residue was passed through the reversed phase C-18 column and the product containing fractions were combined and freeze-dried to give the desired product in a form of white solid (95 mg, 22% yield)

$^1$H NMR (DMSO-d$_6$, 500 MHz) δ[ppm]: 8.00 (d, 2H, J=7.5 Hz), 7.84 (d, 1H, J=7.5 Hz), 7.66 (t, 1H, J=7.5 Hz), 7.58 (t, 1H, J=7.5 Hz), 7.30 (d, 2H, J=8.5 Hz), 7.11 (d, 2H, J=8.0 Hz), 3.98 (m, 2H), 3.71 (t, 1H, J=11.5 Hz), 3.34 (q, 2H, J=7.0 Hz), 3.21 (brs, 3H), 3.00 (t, 2H, J=12.0 Hz), 2.90 (brs, 1H), 2.17 (d, 2H, J=11.0 Hz), 1.91 (m, 2H), 1.05 (t, 1H, J=7.0 Hz).

ESI-MS for $C_{23}H_{27}ClN_6O_2$ expected 454.96. found 455.3/457.3 (M+1), 453.3/455.3 (M−1).

| Ex # | Activity | Structure |
|---|---|---|
| 2 | C | 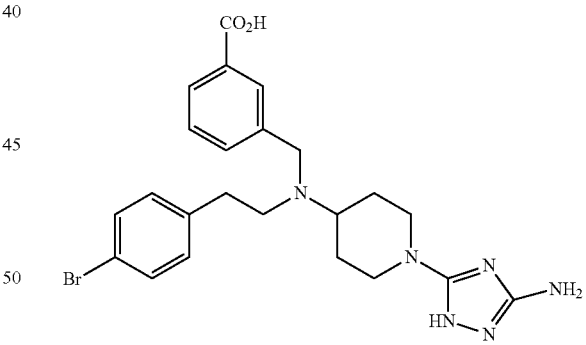 |

Example 3

3-(((1-(3-amino-1H-1,2,4-triazol-5-yl)piperidin-4-yl)(4-bromophenethyl)amino)-methyl)benzoic acid The title compound was prepared exactly in the same manner as Example 2 (all steps) starting from N-Boc-piperid-4-one, 2-(4-bromophenyl)ethylamine, and methyl 3-formylbenzoate.

$^1$H NMR (D$_2$O, 500 MHz) δ[ppm]: 7.77 (s, 1H), 7.73 (d, 1H, J=7.5 Hz), 7.42 (d, 1H, J=7.7 Hz), 7.38 (d, 1H, J=7.9 Hz), 7.35 (d, 2H, J$_{AA'BB'}$=8.3 Hz), 6.97 (d, 2H, J$_{AA'BB'}$=8.5 Hz), 3.75 (d, 2H, J=12.6 Hz), 3.71 (s, 2H), 2.73-2.78 (m, 1H), 2.62-2.73 (m, 4H), 2.55-2.59 (m, 2H), 1.90 (d, 2H, J=12.2 Hz), 1.56 (ddd, 2H, J=24.7 Hz, J=12.4 Hz, J=3.4 Hz).

ESI-MS for $C_{23}H_{27}BrN_6O_2$ calculated 499.41. found 499.2/501.3 (M+1), 497.2/499.3 (M−1).

| Ex # | Activity | Structure |
|---|---|---|
| 3 | A | 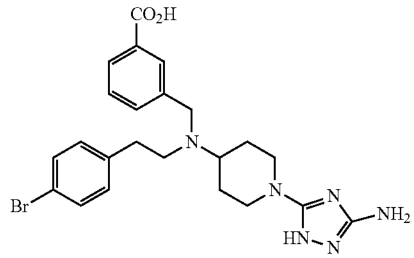 [SMILES: Nc1n[nH]c(N2CCC(N(CCc3ccc(Br)cc3)Cc3cccc(C(=O)O)c3)CC2)n1] |

Example 4

4-(((1-(3-amino-1H-1,2,4-triazol-5-yl)piperidin-4-yl)(4-bromophenethyl)-amino)methyl)benzoic acid

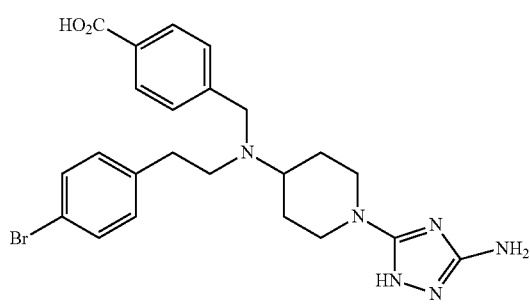 [SMILES: Nc1n[nH]c(N2CCC(N(CCc3ccc(Br)cc3)Cc3ccc(C(=O)O)cc3)CC2)n1]

The title compound was prepared exactly in the same manner as Example 2 (all steps) starting from N-Boc-piperid-4-one, 2-(4-bromophenyl)ethylamine, and methyl 4-formylbenzoate.

$^1$H NMR (D$_2$O, 500 MHz) δ[ppm]: 7.21 (d, 2H, J$_{AA'BB'}$=8.5 Hz); 6.78 (d, 2H, J$_{AA'BB'}$=8.3 Hz); 6.58 (d, 2H, J$_{AA'BB'}$=8.3 Hz); 6.17 (d, 2H, J$_{AA'BB'}$=8.3 Hz); 3.80 (d, 1H, J=13.3 Hz); 3.55 (d, 1H, J=13.3 Hz); 3.02-3.07 (m, 2H), 2.90-2.94 (m, 1H); 2.66-2.69 (m, 1H); 2.52-2.55 (m, 1H); 2.26-2.35 (m, 2H); 2.12-2.18 (m, 1H), 1.92-1.99 (m, 1H), 1.40-1.45 (m, 2H), 1.14-1.22 (m, 2H).

ESI-MS for C$_{23}$H$_{27}$BrN$_6$O$_2$ calculated 499.41. found 499.0/501.0 (M+1), 497.1/499.1 (M−1).

| Ex # | Activity | Structure |
|---|---|---|
| 4 | A | 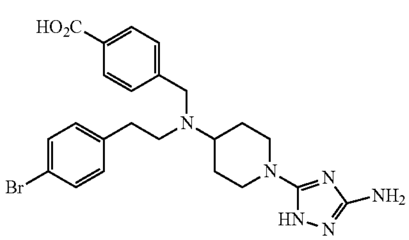 [SMILES: Nc1n[nH]c(N2CCC(N(CCc3ccc(Br)cc3)Cc3ccc(C(=O)O)cc3)CC2)n1] |

Example 5

4-(((1-(3-amino-1H-1,2,4-triazol-5-yl)piperidin-4-yl)(4-chlorophenethyl)amino)-methyl)-2-methylbenzoic acid

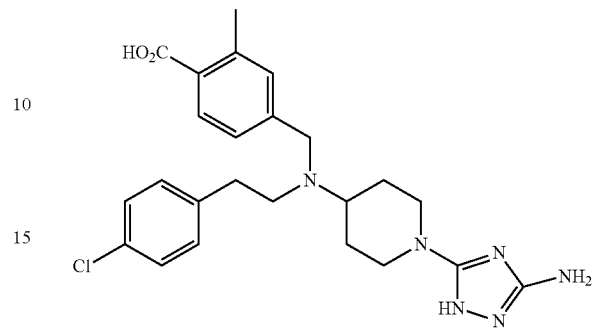

The title compound was prepared exactly in the same manner as Example 2 (all steps) starting from N-Boc-piperid-4-one, 2-(4-chlorophenyl)ethylamine, and methyl 4-formyl-2-methylbenzoate.

$^1$H NMR (DMSO-d$_6$, 500 MHz) δ[ppm]: 9.87 (brs, 1H), 7.84 (brs, 1H), 7.47 (brs, 1H), 7.33 (d, J$_{AB}$=7.9 Hz, 2H), 7.18 (d, J$_{AB}$=7.9 Hz, 2H), 4.53 (brs, 1H), 4.30 (brs, 1H), 3.90-3.80 (m, 2H), 3.57 (brs, 1H), 3.25 (brs, 1H), 3.16 (brs, 1H), 2.97 (brs, 1H), 2.93-2.86 (m, 2H), 2.80 (brs, 1H), 2.50 (s, 3H), 2.11 (brs, 2H), 1.82 (brs, 2H).

ESI-MS for C$_{24}$H$_{29}$ClN$_6$O$_2$ calculated 468.99. found 469.0/471.0 (M+1), 467.1/469.2 (M−1).

| Ex # | Activity | Structure |
|---|---|---|
| 5 | A | 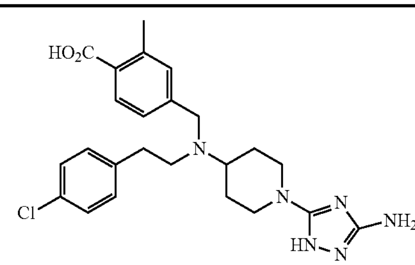 |

Example 6

5-(((1-(3-amino-1H-1,2,4-triazol-5-yl)piperidin-4-yl)(4-chlorophenethyl)-amino)methyl)-2-methylbenzoic acid

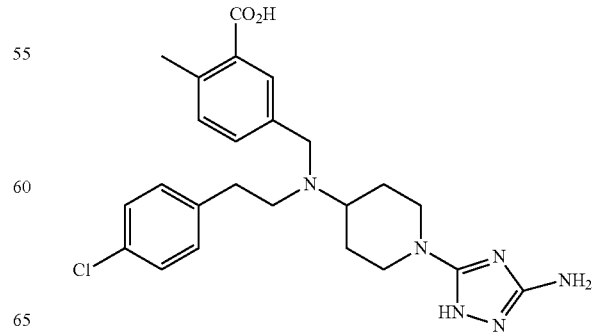

The title compound was prepared exactly in the same manner as Example 2 (all steps) starting from N-Boc-piperid-4-one, 2-(4-chlorophenyl)ethylamine, and methyl 5-formyl-2-methylbenzoate.

$^1$H NMR (DMSO-d$_6$, 500 MHz) δ[ppm]: 12.85 (brs, 1H), 9.75 (brs, 1H), 8.04 (brs, 1H), 7.62 (brs, 1H), 7.37 (d, J=7.3 Hz, 1H), 7.32 (d, J$_{AB}$=8.3 Hz, 2H), 7.16 (d, J$_{AB}$=8.3 Hz, 2H), 4.59-4.50 (m, 1H), 4.34 (brs, 1H), 3.88-3.79 (m, 2H), 3.55 (brs, 1H), 3.25 (brs, 1H), 3.12 (brs, 1H), 2.97 (brs, 1H), 2.92-2.85 (m, 2H), 2.76 (brs, 1H), 2.51 (s, 3H), 2.11 (brs, 2H), 1.18 (brs, 2H).

ESI-MS for C$_{24}$H$_{29}$ClN$_6$O$_2$ calculated 468.99. found 469.0/471.0 (M+1), 467.2/469.2 (M−1).

| Ex # | Activity | Structure |
|---|---|---|
| 6 | B | 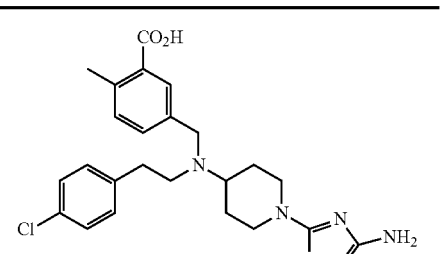 |

Example 7

5-(((1-(3-amino-1H-1,2,4-triazol-5-yl)piperidin-4-yl)(4-chlorophenethyl)amino)-methyl)-2-chlorobenzoic acid

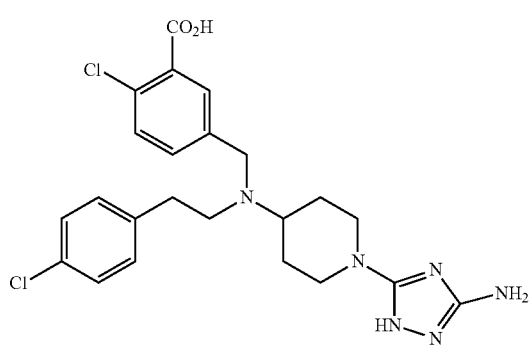 [SMILES: Nc1n[nH]c(N2CCC(N(CCc3ccc(Cl)cc3)Cc3ccc(Cl)c(C(=O)O)c3)CC2)n1]

The title compound was prepared exactly in the same manner as Example 2 (all steps) starting from N-Boc-piperid-4-one, 2-(4-chlorophenyl)ethylamine, and methyl 2-chloro-5-formylbenzoate.

$^1$H NMR (DMSO-d$_6$, 500 MHz) δ[ppm]: 13.19 (brs, 1H), 10.81 (brs, 1H), 8.09 (brs, 1H), 7.85 (brs, 1H), 7.62 (brs, 1H), 7.33 (d, J=7.5 Hz, 2H), 7.18 (d, J=7.5 Hz, 2H), 4.53 (brs, 1H), 4.37 (brs, 1H), 3.89 (brs, 1H), 3.21 (brs, 1H), 3.07 (brs, 1H), 2.90 (brs, 3H), 2.18 (brs, 2H), 1.89 (brs, 2H).

ESI-MS for C$_{23}$H$_{26}$Cl$_2$N$_6$O$_2$ calculated 489.41. found 489.0/491.0 (M+1), 487.2/489.2 (M−1).

| Ex # | Activity | Structure |
|---|---|---|
| 7 | A | 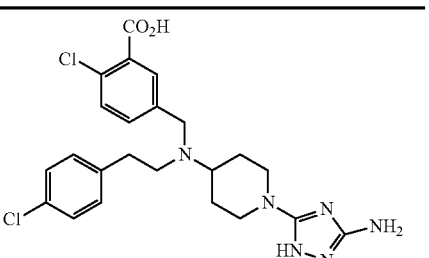 |

Example 8

5-(((1-(3-amino-1H-1,2,4-triazol-5-yl)piperidin-4-yl)(4-chlorophenethyl)amino)-methyl)-2-fluorobenzoic acid

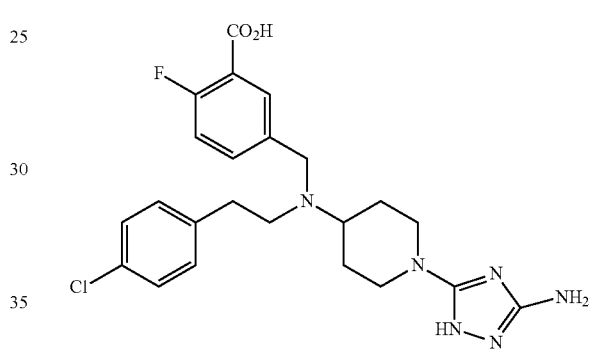

The title compound was prepared exactly in the same manner as Example 2 (all steps) starting from N-Boc-piperid-4-one, 2-(4-chlorophenyl)ethylamine, and methyl 2-fluoro-5-formylbenzoate.

$^1$H NMR (DMSO-d$_6$, 500 MHz) δ[ppm]: 10.60 (brs, 1H), 8.15 (brs, 1H), 7.94 (brs, 1H), 7.42-7.36 (m, 1H), 7.32 (d, J$_{AB}$=8 Hz, 2H), 7.18 (d, J$_{AB}$=8 Hz, 2H), 4.58-4.49 (brs, 1H), 4.41-4.32 (brs, 1H), 3.91-3.80 (brs, 2H), 3.58-3.49 (brs, 1H), 3.30-3.18 (brs, 1H), 3.14-3.00 (brs, 2H), 2.98-2.87 (brs, 2H), 2.87-2.78 (brs, 1H), 2.27-2.12 (brs, 2H), 1.92-1.80 (brs, 2H).

$^{19}$F NMR (DMSO-d$_6$, 500 MHz), −73.77 ppm.

ESI-MS for C$_{23}$H$_{26}$ClFN$_6$O$_2$ calculated 472.95. found 473.2/475.2 (M+1), 471.4/473.4 (M−1).

| Ex # | Activity | Structure |
|---|---|---|
| 8 | B | 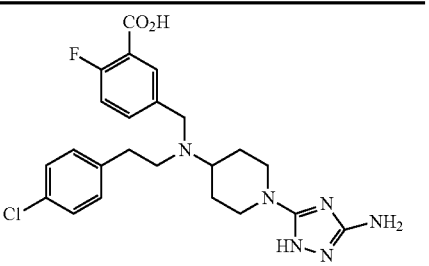 |

Example 9

N-(2-((1-(3-amino-1H-1,2,4-triazol-5-yl)piperidin-4-yl)(4-chlorophenethyl)amino)-ethyl)benzamide

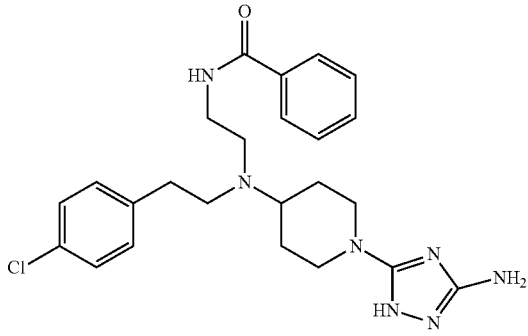 [SMILES: Nc1n[nH]c(N2CCC(N(CCNC(=O)c3ccccc3)CCc3ccc(Cl)cc3)CC2)n1]

Step 1: Allyl 4-((2-((tert-butoxycarbonyl)amino)ethyl)(4-chlorophenethyl)amino)piperidine-1-carboxylate

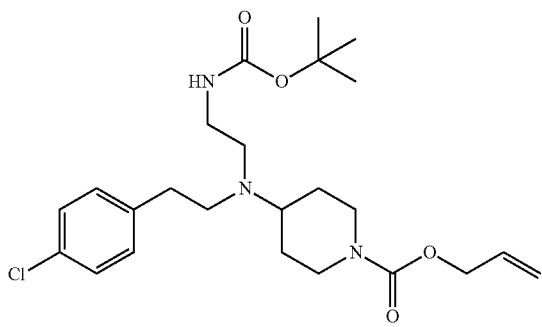 [SMILES: C=CCOC(=O)N1CCC(N(CCNC(=O)OC(C)(C)C)CCc2ccc(Cl)cc2)CC1]

To the solution of N-alloc-piperid-4-one in dichloroethane (DCE) (2 mL/mmol), tert-butyl 2-aminoethylcarbamate (N-Boc-ethylenediamine) (1 equiv) was added followed by addition of NaBH(OAc)$_3$ (2 equiv). The reaction mixture was stirred for 5 hours at room temperature. (4-Chlorophenyl)acetaldehyde (1.5 equiv) was then added, followed by another portion of NaBH(OAc)$_3$ (2 equiv). The reaction mixture was stirred for another 15 hours at room temperature after which time it was taken between 5% NaHCO$_3$ and EtOAc (10 mL/mmol of starting N-alloc-piperid-4-one). The organic layer was washed once again with 5% NaHCO$_3$, then brine (2×) and then it was dried over MgSO$_4$. After filtration of the drying agent and stripping the solvent, the desired product was purified by flash column chromatography over silica gel (yield 75%).

Step 2: Allyl 4-((2-aminoethyl)(4-chlorophenethyl)amino)piperidine-1-carboxylate hydrochloride

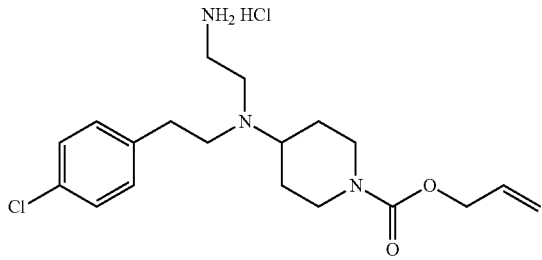

1-Allyloxycarbonyl-N-[2-(tert-butoxycarbonylamino)ethyl]-N-[2-(4-chlorophenyl)ethyl]-piperidin-4-amine obtained in Step 1 was subjected to the deprotection reaction as described in Procedure 2 (4 N HCl in EtOAc). The crude product that was obtained in this step was used in the synthesis of Examples 8-13 without any further purification.

Step 3: Allyl 4-((2-benzamidoethyl)(4-chlorophenethyl)amino)piperidine-1-carboxylate

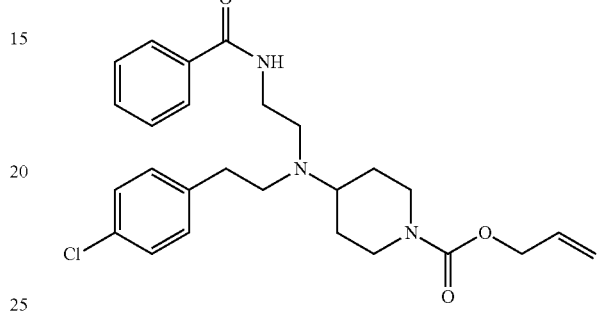

Allyl 4-((2-aminoethyl)(4-chlorophenethyl)amino)piperidine-1-carboxylate hydrochloride obtained in Step 2 was suspended in dichloromethane (4 mL/mmol), the suspension was cooled to −15° C. and DIPEA (2.2 equiv) followed by benzoyl chloride (1.05 equiv) were added dropwise over 5 minutes. The cooling bath was removed and the reaction mixture was allowed to warm to ambient temperature. After 2 h TLC revealed no presence of starting material. The reaction mixture was diluted with EtOAc (10 mL/mmol of starting material), washed with 1 M NaOH (2×), water (2×) and brine (2×) and dried over anhydrous MgSO$_4$. After filtration of the drying agent the solvent was stripped off and the crude product was purified by column chromatography.

Step 4: N-(2-((4-chlorophenethyl)(piperidin-4-yl)amino)ethyl)benzamide

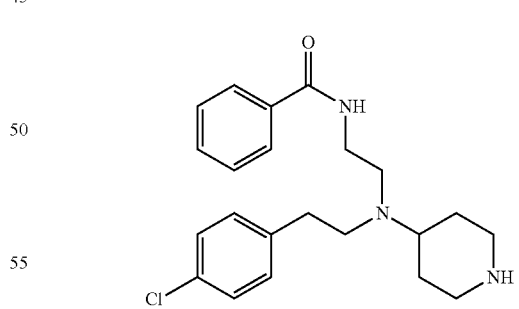

The solution of allyl 4-((2-benzamidoethyl)(4-chlorophenethyl)amino)piperidine-1-carboxylate, PhSiH$_3$ (5 equiv) in DCM (8 mL/mmol) was degassed for 10 min by bubbling argon through the inserted needle, prior to the addition of Pd(Ph$_3$P)$_4$ (5 mol %). After 20 min TLC indicated completion of reaction. The reaction was concentrated and was purified by column chromatography in DCM/MeOH solvent system (gradient 100:1 to 10:1) to give pure product in a form of an off-white solid.

Step 5: N-(2-((1-(3-amino-1H-1,2,4-triazol-5-yl) piperidin-4-yl)(4-chlorophenethyl)amino)-ethyl) benzamide N-(2-((4-Chlorophenethyl)(piperidin-4-yl)amino)ethyl) benzamide obtained in Step 4 was reacted with K$_2$CO$_3$ and S,S'-dimethyl-N-cyano-dithioiminocarbonate, followed by the cyclization of the intermediate (N-cyanopiperazine-1-carbimidothioate) with hydrazine monohydrate in a manner described in Procedure 3. Purification over silica gel provided pure product.

$^1$H NMR (DMSO-d$_6$, 600 MHz) δ[ppm]: 9.08 (brs, 1H), 7.94-7.91 (m, 2H), 7.54-7.5 (m, 1H), 7.47-7.43 (m, 2H), 7.35 (d, 2H, J=7.7 Hz), 7.32 (d, 2H, J=7.7 Hz), 3.9 (brs, 2H), 3.77-3.7 (m, 3H), 3.44 (brs, 1H), 3.36 (brs, 1H) 3.32-3.24 (m, 2H), 3.18-3.12 (m, 2H), 3.04-2.9 (m, 2H), 2.22-2.13 (m, 2H), 1.82-1.74 (m, 2H).

ESI-MS for C$_{24}$H$_{30}$ClN$_7$O calculated 468.01. found 468.2/470.1 (M+1), 466.3/468.3 (M−1).

| Ex # | Activity | Structure |
|---|---|---|
| 9 | B | 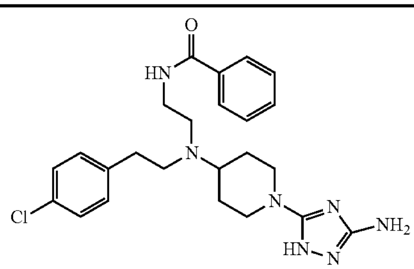 |

Example 10

N-(2-((1-(3-amino-1H-1,2,4-triazol-5-yl)piperidin-4-yl)(4-chlorophenethyl)-amino)ethyl)acetamide

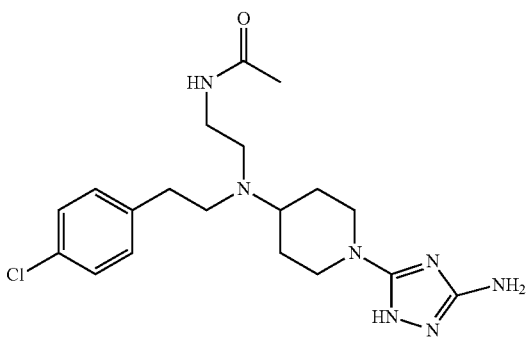 [SMILES: CC(=O)NCCN(CCc1ccc(Cl)cc1)C1CCN(c2nc(N)n[nH]2)CC1]

Allyl 4-((2-amino ethyl)(4-chlorophenethyl)amino)piperidine-1-carboxylate hydrochloride described in Example 9, Step 2, was carried on to the title compound in a similar manner as described for Example 9, Steps 3-5, using acetyl chloride instead of benzoyl chloride in the acylation step (Step 3).

$^1$H NMR (DMSO-d$_6$, 600 MHz) δ[ppm]: 8.41 (t, 1H, J=5.6 Hz), 7.39 (d, 2H, J=8.3 Hz), 7.35 (d, 2H, J=8.3 Hz), 3.98-3.92 (m, 2H), 3.71-3.64 (m, 1H), 3.52-3.47 (m, 2H), 3.39-3.23 (m, 3H), 3.2-3.1 (m, 3H), 3.03 (brs, 2H), 2.21-2.12 (m, 2H), 1.81 (s, 3H), 1.82-1.75 (m, 2H).

ESI-MS for C$_{19}$H$_{28}$ClN$_7$O calculated 405.93. found 406.1/408.1 (M+1), 404.3/406.3 (M−1).

| Ex # | Activity | Structure |
|---|---|---|
| 10 | C | 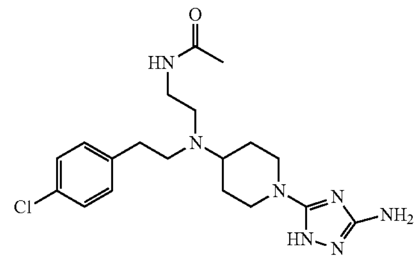 [SMILES: CC(=O)NCCN(CCc1ccc(Cl)cc1)C1CCN(c2nc(N)n[nH]2)CC1] |

Example 11

1-(2-((1-(3-amino-1H-1,2,4-triazol-5-yl)piperidin-4-yl)(4-chlorophenethyl)-amino)ethyl)-3-methylurea Allyl 4-((2-aminoethyl)(4-chlorophenethyl)amino)piperidine-1-carboxylate hydrochloride described in Example 9, Step 2, was carried on to the title compound in a similar manner as described for Example 9, Steps 3-5, using methyl isocyanate instead of benzoyl chloride in the urea formation step (Step 3).

$^1$H NMR (DMSO-d$_6$, 500 MHz): 10.78 (s, 1H), 7.40 (d, 2H, J=8.5 Hz), 7.37 (d, 2H, J=8.5 Hz), 6.95 (brs, 1H), 6.60 (brs, 1H), 6.42 (brs, 1H), 3.93 (d, 2H, J=12.5 Hz), 3.63 (t, 1H, J=11 Hz), 3.42-3.26 (m, 5H), 3.11-3.08 (m, 3H), 2.91 (t, 2H, J=12 Hz), 2.56 (s, 3H), 2.08 (t, 3H, J=8.5 Hz), 1.78-1.71 (m, 2H).

ESI-MS for C$_{19}$H$_{29}$ClN$_8$O calculated 420.95. found 421.2/423.1 (M+1), 419.4/421.4 (M−1).

| Ex # | Activity | Structure |
|---|---|---|
| 11 | D | 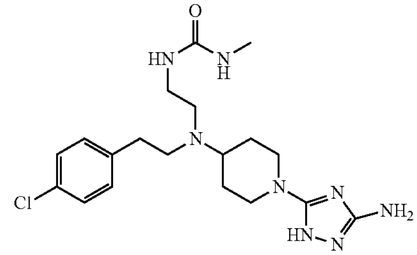 [SMILES: CNC(=O)NCCN(CCc1ccc(Cl)cc1)C1CCN(c2nc(N)n[nH]2)CC1] |

Example 12

1-(2-((1-(3-amino-1H-1,2,4-triazol-5-yl)piperidin-4-yl)(4-chlorophenethyl)-amino)ethyl)-3-isopropylurea

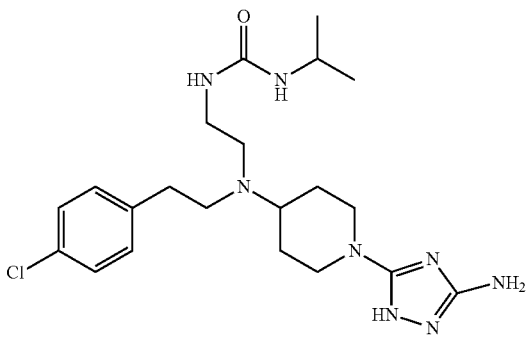 [SMILES: CC(C)NC(=O)NCCN(CCc1ccc(Cl)cc1)C1CCN(c2nc(N)n[nH]2)CC1]

Allyl 4-((2-aminoethyl)(4-chlorophenethyl)amino)piperidine-1-carboxylate hydrochloride described in Example 9, Step 2, was carried on to the title compound in a similar manner as described for Example 9, Steps 3-5, using isopropyl isocyanate instead of benzoyl chloride in the urea formation step (Step 3).

$^1$H NMR (DMSO-d$_6$, 500 MHz) δ[ppm]: 12.75 (br s, 1H), 10.97 (s, 1H), 7.53 (br s, 1H), 7.40-7.36 (m, 4H), 6.47 (s, 2H), 3.96-3.93 (m, 2H), 3.68-3.64 (m, 3H), 3.24-3.04 (m, 11H), 2.15-2.08 (m, 2H), 1.01 (two doublets, 6H).

ESI-MS for C$_{21}$H$_{33}$ClN$_8$O calculated 449.00. found 449.1/451.1 (M+1), 447.4/449.4 (M−1).

| Ex # | Activity | Structure |
|---|---|---|
| 12 | C | 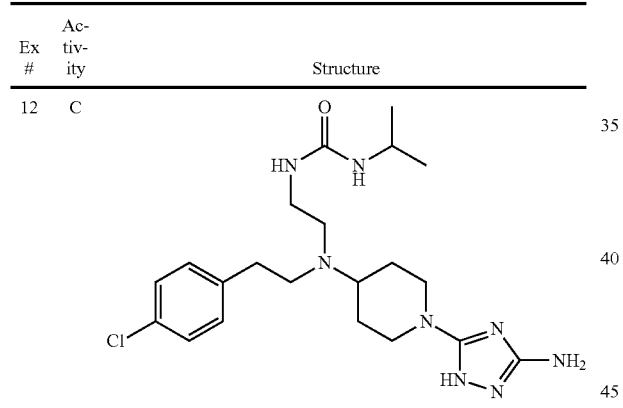 |

Example 13

N-(2-((1-(3-amino-1H-1,2,4-triazol-5-yl)piperidin-4-yl)(4-chlorophenethyl)-amino)ethyl)methanesulfonamide

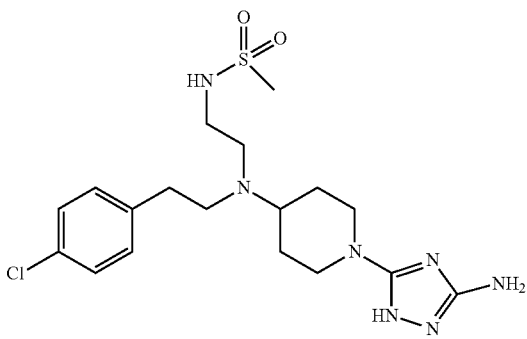 [SMILES: CS(=O)(=O)NCCN(CCc1ccc(Cl)cc1)C1CCN(c2nc(N)n[nH]2)CC1]

Allyl 4-((2-aminoethyl)(4-chlorophenethyl)amino)piperidine-1-carboxylate hydrochloride described in Example 9, Step 2, was carried on to the title compound in a similar manner as described for Example 9, Steps 3-5, using methanesulfonyl chloride instead of benzoyl chloride in the sulfonamide formation step (Step 3).

$^1$H NMR (DMSO-d$_6$, 500 MHz) δ[ppm]: 11.00 (s, 1H), 7.58 (s, 1H), 7.41 (d, 2H, J=10 Hz), 7.37 (d, 2H, J=10 Hz), 3.95-3.93 (m, 2H), 3.69-3.67 (m, 2H), 3.25-3.02 (m, 14H), 2.20-2.16 (m, 2H), 1.81-1.77 (m, 2H).

ESI-MS for C$_{18}$H$_{28}$ClN$_7$O$_2$S calculated 441.99. found 441.9/444.0 (M+1), 441.4/443.4 (M−1).

| Ex # | Activity | Structure |
|---|---|---|
| 13 | B | 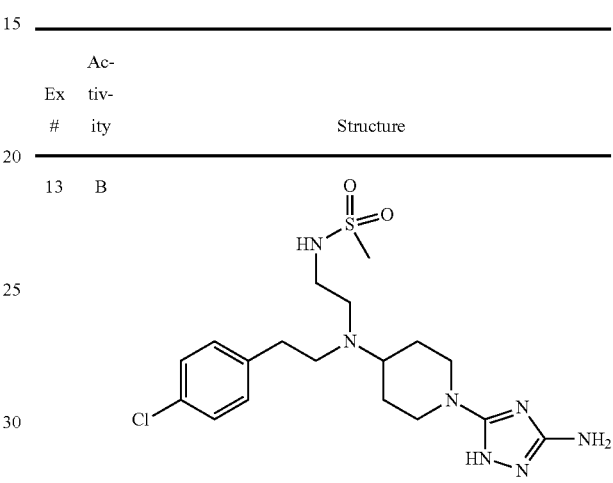 |

Example 14

N-(2-((1-(3-amino-1H-1,2,4-triazol-5-yl)piperidin-4-yl)(4-chlorophenethyl)-amino)ethyl)-2,2,2-trifluoroacetamide

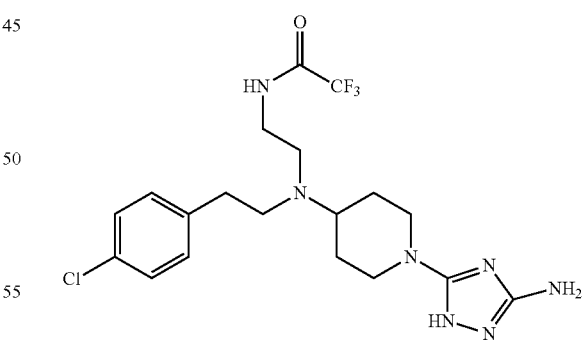

Allyl 4-((2-aminoethyl)(4-chlorophenethyl)amino)piperidine-1-carboxylate hydrochloride described in Example 9, Step 2, was carried on to the title compound in a similar manner as described for Example 9, Steps 3-5, using trifluoroacetic anhydride instead of benzoyl chloride in the acylation step (Step 3).

ESI-MS for C$_{19}$H$_{25}$ClF$_3$N$_7$O calculated 459.91. found 460.2/462.2 (M+1), 458.5/460.5 (M−1).

| Ex # | Activity | Structure |
|---|---|---|
| 14 | C | 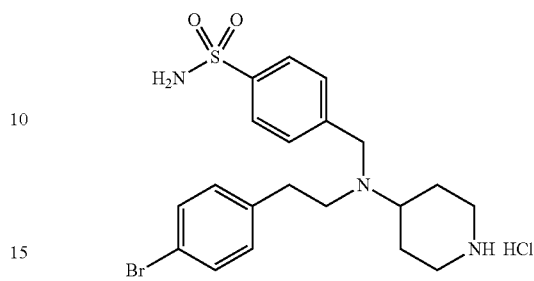 |

Example 15

4-(((1-(3-amino-1H-1,2,4-triazol-5-yl)piperidin-4-yl)(4-bromophenethyl)amino)-methyl)benzenesulfonamide

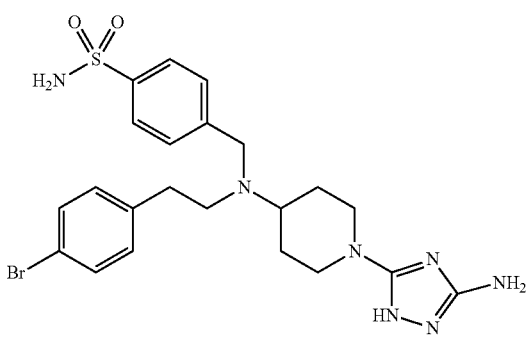 [SMILES: Nc1n[nH]c(N2CCC(N(CCc3ccc(Br)cc3)Cc3ccc(S(N)(=O)=O)cc3)CC2)n1]

Step 1: tert-butyl 4-((4-bromophenethyl)(4-sulfamoylbenzyl)amino)piperidine-1-carboxylate

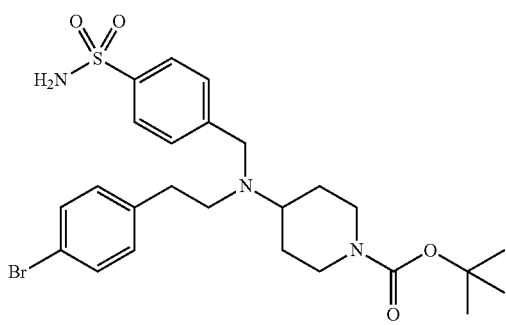 [SMILES: CC(C)(C)OC(=O)N1CCC(N(CCc2ccc(Br)cc2)Cc2ccc(S(N)(=O)=O)cc2)CC1]

The title compound was obtained in a manner described in Procedure 1A from N-Boc-piperid-4-one, (4-bromophenyl)acetaldehyde, and 4-aminomethylbenzenesulfonamide.

ESI-MS for $C_{25}H_{34}BrN_3O_4S$ calculated 552.54. found 552.6/554.6 (M+1), 550.5/552.5 (M−1).

Step 2: 4-(((4-bromophenethyl)(piperidin-4-yl)amino)methyl)benzenesulfonamide hydrochloride tert-Butyl 4-(4-bromophenethyl)(4-sulfamoylbenzyl)amino)piperidine-1-carboxylate obtained in Step 1 was subjected to the deprotection reaction as described in Procedure 2 (4 N HCl in AcOEt).

ESI-MS for $C_{20}H_{26}BrN_3O_2S$ calculated 452.42. found 452.5/454.5 (M+1), 450.5/452.5 (M−1).

Step 3: 4-(((1-(3-amino-1H-1,2,4-triazol-5-yl)piperidin-4-yl)(4-bromophenethyl)amino)-methyl)benzenesulfonamide 4-(((4-Bromophenethyl)(piperidin-4-yl)amino)methyl)benzenesulfonamide hydrochloride obtained in Step 2 was reacted with $K_2CO_3$ and S,S'-dimethyl-N-cyano-dithioiminocarbonate, followed by the cyclization of the intermediate (N-cyanopiperazine-1-carbimidothioate) with hydrazine monohydrate in a manner described in Procedure 3.

$^1$H NMR (DMSO-$d_6$, 500 MHz) δ[ppm]: 7.67 (d, $J_{AB}$=8.2 Hz, 2H), 7.39 (d, $J_{AB}$=8.2 Hz, 2H), 7.38 (d, $J_{AB}$=8.2 Hz, 2H), 7.25 (s, 2H), 7.06 (d, $J_{AB}$=8.2 Hz, 2H), 4.10-4.00 (m, 2H), 3.79-3.76 (brs, 2H), 3.69 (s, 2H), 2.65-2.56 (m, 5H), 1.63-1.60 (m, 2H), 1.43-1.34 (m, 2H).

ESI MS for $C_{22}H_{28}BrN_7O_2S$ calculated 534.48. found 534.5/536.5 (M+1), 532.5/534.5 (M−1).

| Ex # | Activity | Structure |
|---|---|---|
| 15 | A | 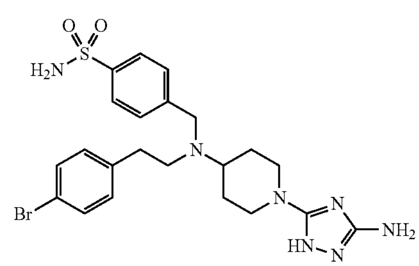 [SMILES: Nc1n[nH]c(N2CCC(N(CCc3ccc(Br)cc3)Cc3ccc(S(N)(=O)=O)cc3)CC2)n1] |

Example 16

N-((4-(((1-(3-amino-1H-1,2,4-triazol-5-yl)piperidin-4-yl)(4-bromophenethyl)-amino)methyl)phenyl)sulfonyl)acetamide

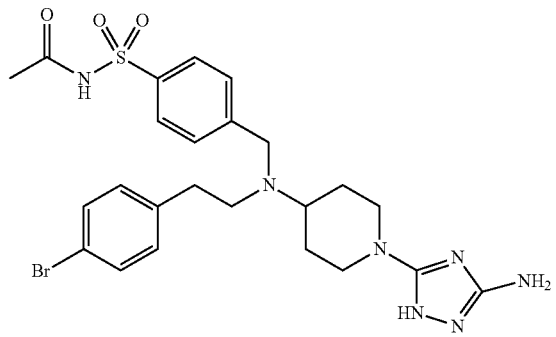 [SMILES: CC(=O)NS(=O)(=O)c1ccc(CN(CCc2ccc(Br)cc2)C2CCN(c3nc(N)n[nH]3)CC2)cc1]

Step 1: tert-butyl 4-((4-(N-acetylsulfamoyl)benzyl)(4-bromophenethyl)amino)piperidine-1-carboxylate

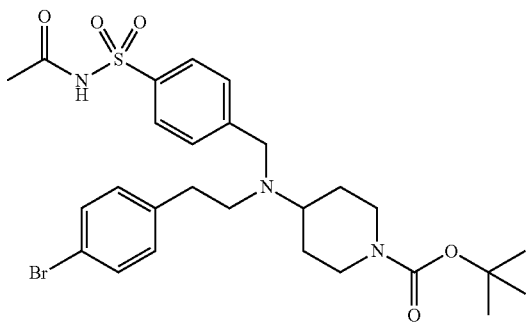 [SMILES: CC(=O)NS(=O)(=O)c1ccc(CN(CCc2ccc(Br)cc2)C2CCN(C(=O)OC(C)(C)C)CC2)cc1]

tert-Butyl 4-((4-bromophenethyl)(4-sulfamoylbenzyl)amino)piperidine-1-carboxylate (see Example 15, step 1) was dissolved in anhydrous THF (5 mL/mmol) under atmosphere of argon and the solution was cooled to 0° C. Sodium hydride (2 equiv) was then added in one portion and after 10 minutes acetyl chloride (2 equiv) was added dropwise by syringe over 10 minutes. The cooling batch was removed and the reaction mixture was allowed to stir for two days after which time the starting material could no longer be detected. The reaction mixture was then diluted with EtOAc (12 mL/mmol of starting material), washed with 1 M NaOH (2×), water (2×) and brine (2×) and dried over anhydrous MgSO$_4$. After filtration of the drying agent the solvent was stripped off and the crude product was purified by column chromatography (yield 65%).

ESI MS for $C_{27}H_{36}BrN_3O_5S$ calculated 594.57. found 594.8/596.8 (M+1), 592.7/594.7 (M−1).

Step 2: N-((4-(((4-bromophenethyl)(piperidin-4-yl)amino)methyl)phenyl)sulfonyl)acetamide hydrochloride

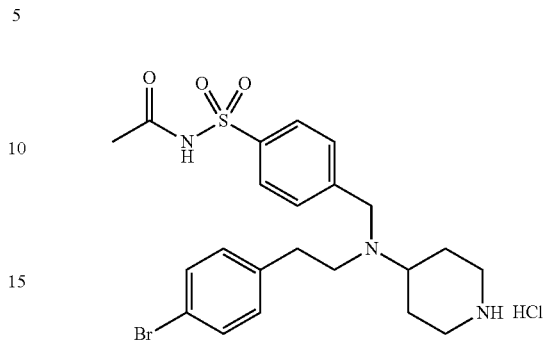

tert-Butyl 4-((4-(N-acetylsulfamoyl)benzyl)(4-bromophenethyl)amino)piperidine-1-carboxylate obtained in Step 1 was subjected to the deprotection reaction as described in Procedure 2 (4 N HCl in EtOAc). The crude product was carried on to the next step without further purification.

ESI MS for $C_{22}H_{28}BrN_3O_3S$ calculated 494.45. found 494.7/496.7 (M+1), 492.6/494.4 (M−1).

Step 3: N-((4-(((1-(3-amino-1H-1,2,4-triazol-5-yl)piperidin-4-yl)(4-bromophenethyl)amino)-methyl)phenyl)sulfonyl)acetamide N-((4-(((4-Bromophenethyl)(piperidin-4-yl)amino)methyl)phenyl)sulfonyl)acetamide hydrochloride obtained in Step 2 was reacted with $K_2CO_3$ and S,S'-dimethyl-N-cyano-dithioiminocarbonate, followed by the cyclization of the intermediate (N-cyanopiperazine-1-carbimidothioate) with hydrazine monohydrate in a manner described in Procedure 3.

$^1$H NMR (DMSO-d$_6$+D$_2$O, 500 MHz) δ[ppm]: 7.93 (d, 2H, J$_{AA'BB'}$=6.2 Hz), 7.77 (brs, 2H,), 7.40 (d, 2H, J$_{AA'BB'}$=6.6 Hz), 7.01 (d, 2H, J$_{AA'BB'}$=6.4 Hz), 4.41 (brs, 2H), 3.51 (brs, 1H), 3.10-3.14 (m, 2H), 2.73-2.90 (m, 4H), 2.08 (brs, 2H), 1.86 (s, 3H), 1.76-1.79 (m, 2H).

ESI-MS for $C_{24}H_{30}BrN_7O_3S$ calculated 576.52. found 576.9/578.9 (M+1), 574.6/576.4 (M−1).

| Ex # | Activity | Structure |
|---|---|---|
| 16 | A | <br> |

Example 17

N-((4-(((1-(3-amino-1H-1,2,4-triazol-5-yl)piperidin-4-yl)(4-bromophenethyl)-amino)methyl)phenyl)sulfonyl)isobutyramide

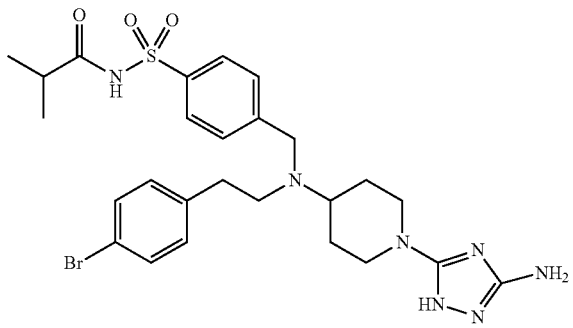 [SMILES: CC(C)C(=O)NS(=O)(=O)c1ccc(CN(CCc2ccc(Br)cc2)C2CCN(c3nc(N)n[nH]3)CC2)cc1]

The title compound was prepared in the same manner as Example 16 (all steps) using isobutyryl chloride instead of acetyl chloride in the acylation step (Step 2).

$^1$H NMR (CD$_3$OD, 500 MHz) δ[ppm]: 7.91 (d, 2H, $J_{AA'BB'}$=8.3 Hz), 7.50 (d, 2H, $J_{AA'BB'}$=8.1 Hz), 7.37 (d, 2H, $J_{AA'BB'}$=8.3 Hz), 7.01 (d, 2H, $J_{AA'BB'}$=8.3 Hz), 3.89-3.91 (m, 4H), 2.82-2.90 (m, 3H), 2.76 (dd, 2H, J=11.9 Hz, J=12.2 Hz), 2.65-2.68 (m, 2H), 2.39-2.45 (m, 1H), 1.83 (brd, 2H, J=11.5 Hz), 1.59-1.66 (m, 2H), 1.00 (d, 6H, J=6.8 Hz).

ESI-MS for C$_{26}$H$_{34}$BrN$_7$O$_3$S calculated 604.57. found 604.2/606.2 (M+1), 602.3/604.3 (M-1).

| Ex # | Activity | Structure |
|---|---|---|
| 17 | A | 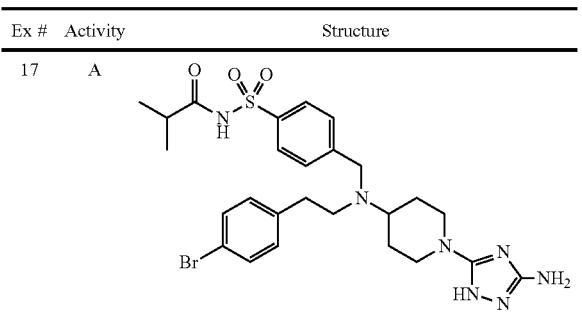 |

Example 18

N-((3-(((1-(3-amino-1H-1,2,4-triazol-5-yl)piperidin-4-yl)(4-bromophenethyl)-amino)methyl)phenyl)sulfonyl)acetamide

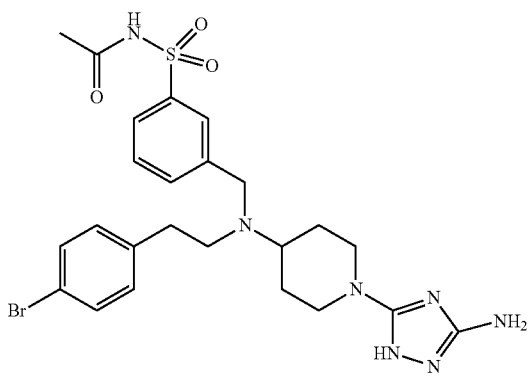 [SMILES: CC(=O)NS(=O)(=O)c1cccc(CN(CCc2ccc(Br)cc2)C2CCN(c3nc(N)n[nH]3)CC2)c1]

The title compound was prepared in the same manner as Example 16 (all steps) starting from N-Boc-piperid-4-one, (4-bromophenyl)acetaldehyde, and 3-aminomethylbenzenesulfonamide in reductive amination Step 1.

1H NMR (DMSO-d$_6$+D$_2$O, 500 MHz) δ[ppm]: 7.75 (s, 1H), 7.58-7.60 (m, 1H), 7.37 (d, 2H, $J_{AA'BB'}$=8.2 Hz), 7.29-7.32 (m, 2H), 7.07 (d, 2H, $J_{AA'BB'}$=8.2 Hz), 3.76 (brd, 2H, J=11.9 Hz), 3.68 (s, 2H), 2.55-2.63 (m, 7H), 1.70 (s, 3H), 1.64 (brd, 2H, J=11.5 Hz), 1.34-1.42 (m, 2H).

ESI-MS for C$_{24}$H$_{30}$BrN$_7$O$_3$S calculated 576.52. found 576.0/578.1 (M+1), 574.1/576.2 (M-1).

| Ex # | Activity | Structure |
|---|---|---|
| 18 | A | 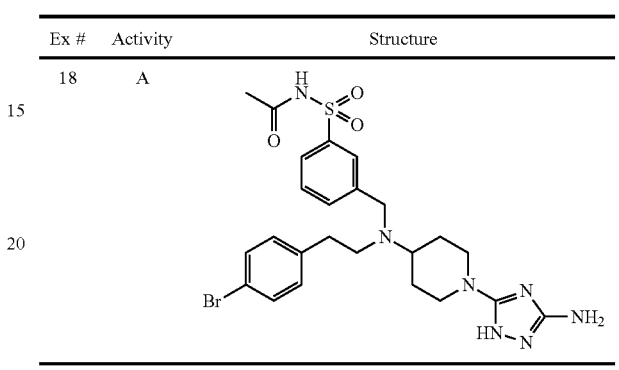 |

Example 19

3-(((1-(3-amino-1H-1,2,4-triazol-5-yl)piperidin-4-yl)(4-chlorophenethyl)amino)-methyl)-N-(2,2,2-trifluoroethyl)benzenesulfonamide

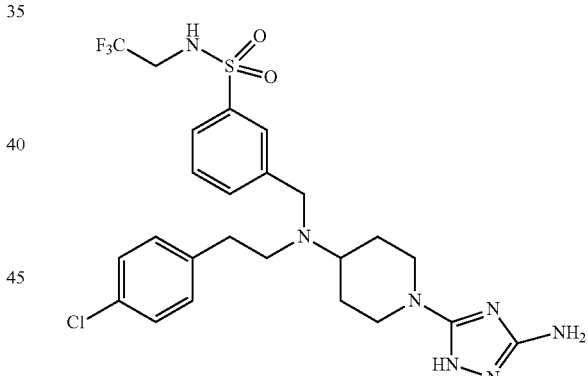

The title compound was prepared as described for Example 15 in a manner described in Procedure 1A from N-Boc-piperid-4-one, (4-chlorophenyl)acetaldehyde, and 3-(aminomethyl)-N-(2,2,2-trifluoroethyl)benzenesulfonamide used in the reductive amination step followed by Procedure 2 and Procedure 3 for N-Boc-deprotection and triazole ring installation, respectively.

$^1$H NMR (DMSO-d$_6$, 500 MHz) δ[ppm]: 10.95 (brs, 1H), 8.62 (t, 1H, J=6.0 Hz), 7.80 (s, 1H), 7.67 (d, 1H, J=7.3 Hz), 7.46-7.52 (m, 2H), 7.27 (d, 2H, $J_{AA'BB'}$=8.3 Hz), 7.15 (d, 2H, $J_{AA'BB'}$=8.3 Hz), 5.51 (brs, 2H), 3.82 (brd, 2H, J=11.9 Hz), 3.75 (s, 2H), 3.63-3.70 (m, 2H), 2.61-2.66 (m, 5H), 2.50-2.57 (m, 2H), 1.65 (brd, 2H, J=10.9 Hz), 1.40-1.47 (m, 2H).

$^{19}$F NMR (DMSO-d$_6$, 500 MHz) -70.39 ppm.

ESI-MS for C$_{24}$H$_{29}$ClF$_3$N$_7$O$_2$S calculated 572.06. found 572.0/574.0 (M+1), 570.2/572.2 (M-1).

| Ex # | Activity | Structure |
|---|---|---|
| 19 | B | 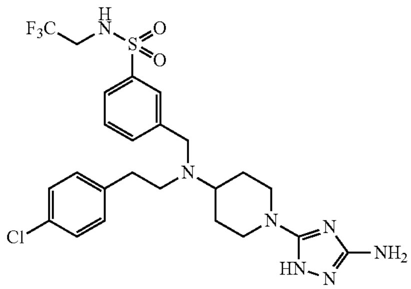 [SMILES: Nc1n[nH]c(N2CCC(N(CCc3ccc(Cl)cc3)Cc3cccc(S(=O)(=O)NCC(F)(F)F)c3)CC2)n1] |

Example 20

2-((1-(3-amino-1H-1,2,4-triazol-5-yl)piperidin-4-yl)(4-chlorophenethyl)amino)-N-methylacetamide

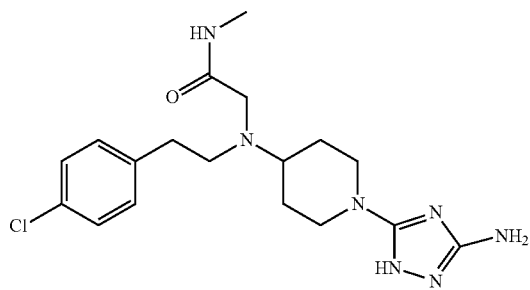 [SMILES: CNC(=O)CN(CCc1ccc(Cl)cc1)C1CCN(c2nc(N)n[nH]2)CC1]

The title compound was prepared as described for Example 15 in a manner described in Procedure 1A from N-Boc-piperid-4-one, (4-chlorophenyl)acetaldehyde, and 2-amino-N-methylacetamide used in the reductive amination step followed by Procedure 2 and Procedure 3 for N-Boc-deprotection and triazole ring installation, respectively.

$^1$H NMR (DMSO-d$_6$, 600 MHz) δ[ppm]: 8.8 (brs, 1H), 7.37 (d, 2H, J=8.3 Hz), 7.29 (d, 2H, J=8.3 Hz), 4.15-4.08 (m, 1H), 3.97 (brs, 1H), 3.95-3.89 (m, 2H), 3.66-3.59 (m, 1H), 3.34 (brs, 2H), 3.02-2.91 (m, 4H), 2.65 (d, 3H, J=4.7 Hz), 2.03 (brs, 2H). 1.76 (brs, 1H), 1.64 (brs, 1H).

ESI MS for C$_{18}$H$_{26}$ClN$_7$O calculated 391.91. found 392.0/394.0 (M+1), 390.2/392.2 (M−1).

| Ex # | Activity | Structure |
|---|---|---|
| 20 | C | 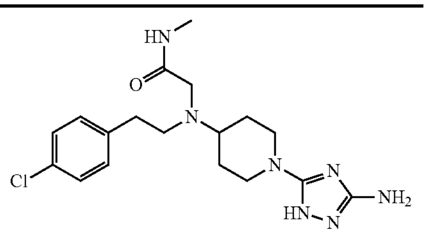 |

Example 21

2-((1-(3-amino-1H-1,2,4-triazol-5-yl)piperidin-4-yl)(4-chlorophenethyl)amino)-N-phenylacetamide

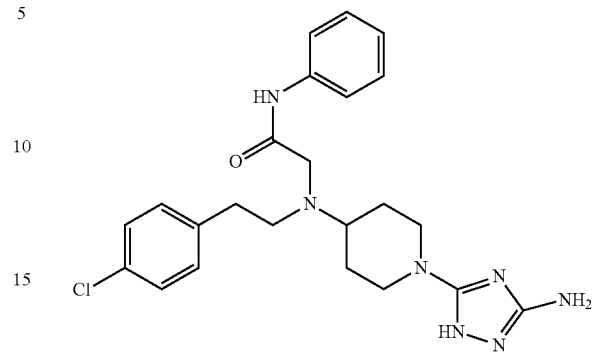

The title compound was prepared as described for Example 15 in a manner disclosed in Procedure 1A from N-Boc-piperid-4-one, (4-chlorophenyl)acetaldehyde, and 2-amino-N-phenylacetamide used in the reductive amination step followed by Procedure 2 and Procedure 3 for N-Boc-deprotection and triazole ring installation, respectively.

$^1$H NMR (DMSO-d$_6$, 600 MHz) δ[ppm]: 9.2 (brs, 1H), 7.36 (d, 2H, J=7.9 Hz), 7.29-7.22 (d, 6H), 7.01 (t, 1H, J=7.3 Hz), 3.81 (brs, 1H), 3.79 (brs, 1H), 3.21 (s, 2H), 2.84-2.79 (m, 2H), 2.76-2.72 (m, 3H), 2.62-2.55 (m, 2H), 1.68-1.64 (m, 2H), 1.41-1.34 (m, 2H).

ESI MS for C$_{23}$H$_{28}$ClN$_7$O calculated 453.98. found 454.0/456.0 (M+1), 452.2/454.2 (M−1).

| Ex # | Activity | Structure |
|---|---|---|
| 21 | C | 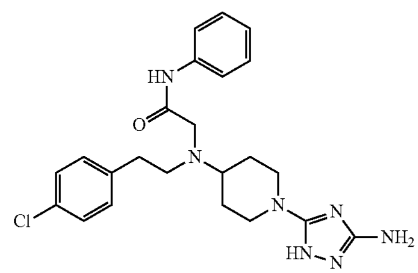 [SMILES: Nc1n[nH]c(N2CCC(N(CCc3ccc(Cl)cc3)CC(=O)Nc3ccccc3)CC2)n1] |

Example 22

2-((1-(3-amino-1H-1,2,4-triazol-5-yl)piperidin-4-yl)(4-chlorophenethyl)amino)-N-isopropylacetamide

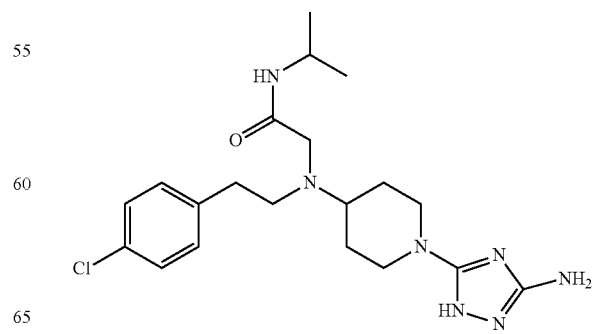

The title compound was prepared as described for Example 15 in a manner described in Procedure 1A from N-Boc-piperid-4-one, (4-chlorophenyl)acetaldehyde, and 2-amino-N-isopropylacetamide, followed by Procedure 2 and Procedure 3 for N-Boc-deprotection and triazole ring installation, respectively.

¹H NMR (DMSO-d₆, 600 MHz) δ[ppm]: 8.76 (brs, 1H), 7.37 (d, 2H, J=8.3 Hz), 7.29 (d, 2H, J=8.3 Hz), 4.09-4.04 (m, 1H), 3.92 (brs, 2H), 3.88-3.83 (m, 1H), 3.65-3.59 (m, 2H), 3.4-3.3 (m, 2H), 3.02-2.09 (m, 4H), 2.1-1.99 (m, 2H), 1.8-1.72 (m, 1H), 1.67-1.58 (m, 1H), 1.06 (d, 6H, J=6.6 Hz).

ESI-MS for $C_{20}H_{30}ClN_7O$ calculated 419.96. found 420.0/422.0 (M+1), 418.2/420.2 (M−1).

| Ex # | Activity | Structure |
|------|----------|-----------|
| 22 | C | 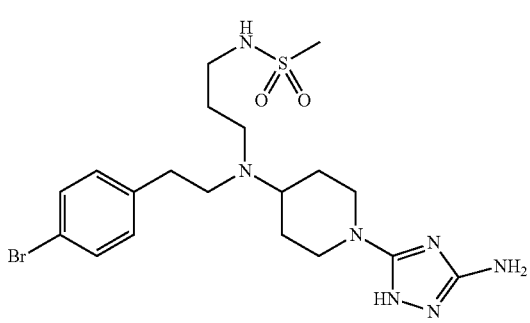 [SMILES: CS(=O)(=O)NCCCN(CCc1ccc(Br)cc1)C1CCN(c2nc(N)n[nH]2)CC1] |

Example 23

N-(3-((1-(3-amino-1H-1,2,4-triazol-5-yl)piperidin-4-yl)(4-bromophenethyl)-amino)propyl)methanesulfonamide

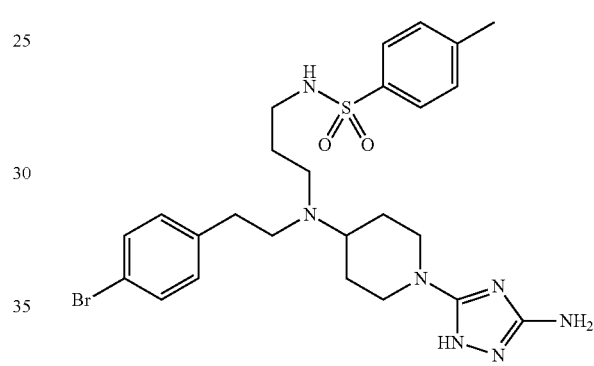

The title compound was prepared as described for Example 15 in a manner disclosed in Procedure 1A from N-Boc-piperid-4-one, (4-bromophenyl)acetaldehyde, and N-(3-aminopropyl)methanesulfonamide, followed by Procedure 2 and Procedure 3 for N-Boc-deprotection and triazole ring installation, respectively.

¹H NMR (CD₃OD, 500 MHz) δ[ppm]: 8.38 (d, 2H, J=10 Hz), 8.15 (d, 2H, J=10 Hz), 4.85-4.83 (m, 2H), 4.61-4.56 (m, 1H), 4.32-4.25 (m, 4H), 4.10-4.07 (m, 2H), 3.98-3.94 (m, 4H), 3.84 (s, 3H), 3.07-3.05 (m, 2H), 2.93-2.92 (m, 2H), 2.83-2.75 (m, 2H).

ESI-MS for $C_{19}H_{30}BrN_7O_2S$ calculated 500.46. found 500.1/502.1 (M+1), 498.2/500.2 (M−1).

| Ex # | Activity | Structure |
|------|----------|-----------|
| 23 | A | 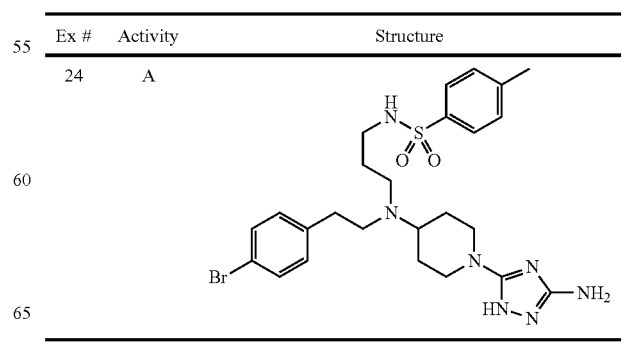 |

Example 24

N-(3-((1-(3-amino-1H-1,2,4-triazol-5-yl)piperidin-4-yl)(4-bromophenethyl)-amino)propyl)-4-methylbenzenesulfonamide The title compound was prepared as described for Example 15 in a manner described in Procedure 1A from N-Boc-piperid-4-one, (4-bromophenyl)acetaldehyde, and N-(3-aminopropyl)-4-methylbenzenesulfonamide, followed by Procedure 2 and Procedure 3 for N-Boc-deprotection and triazole ring installation, respectively.

¹H NMR (D₂O, 500 MHz) δ[ppm]: 7.60 (d, 2H, 10 Hz), 7.41 (d, 2H, 10 Hz), 7.28 (d, 2H, 10 Hz), 7.06 (d, 2H, 10 Hz), 3.69 (dd, 2H), 3.46-2.83 (m, 12H), 2.21 (s, 3H), 1.95-1.92 (m, 2H), 1.65-1.63 (m, 2H).

ESI-MS for $C_{25}H_{34}BrN_7O_2S$ calculated 576.56. found 576.2/578.2 (M+1), 574.3/576.3 (M−1).

| Ex # | Activity | Structure |
|------|----------|-----------|
| 24 | A | 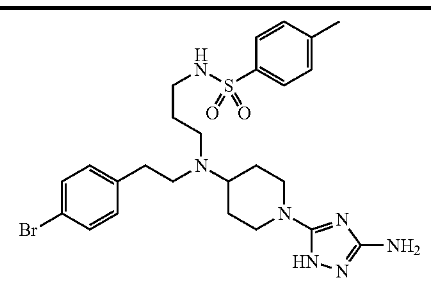 |

Example 25

2-((1-(3-amino-1H-1,2,4-triazol-5-yl)piperidin-4-yl)(4-chlorophenethyl)-amino)acetic acid

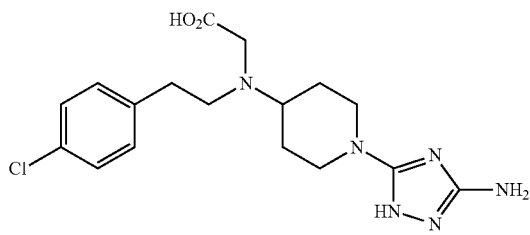 [SMILES: Nc1n[nH]c(N2CCC(N(CCc3ccc(Cl)cc3)CC(=O)O)CC2)n1]

The title compound was prepared as described for Example 1 in a manner described in Procedure 1A from N-Boc-piperid-4-one, (4-chlorophenyl)acetaldehyde, and glycine methyl ester followed by Procedure 2 and Procedure 3 for N-Boc-deprotection and triazole ring installation, respectively. The final hydrolysis of the methyl ester and purification of the title compound were accomplished in a manner similar to Example 2, Step 4.

$^1$H NMR (CD$_3$OD, 500 MHz) δ[ppm]: 7.35 (d, 2H, J=8.5 Hz), 7.30 (d, 2H, J=8.5 Hz), 4.09 (s, 2H), 3.97 (brd, 2H, J=13 Hz), 3.71-3.66 (m, 1H), 3.48-3.44 (m, 2H), 3.10-3.07 (m, 2H), 3.03 (t, 2H, J=12.5 Hz), 2.13 (brd, 2H, J=12 Hz), 1.91-1.83 (m, 2H).

ESI-MS for C$_{17}$H$_{23}$ClN$_6$O$_2$ calculated 378.86. found 379.1/381.1 (M+1), 377.3/379.4 (M−1).

| Ex # | Activity | Structure |
|---|---|---|
| 25 | D | 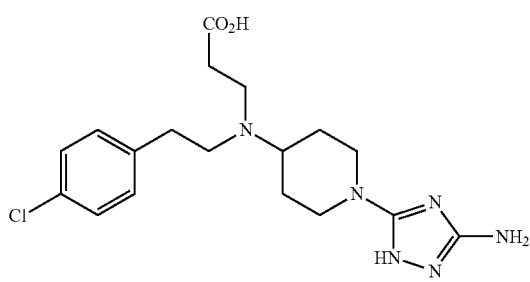 [SMILES: Nc1n[nH]c(N2CCC(N(CCC(=O)O)CCc3ccc(Cl)cc3)CC2)n1] |

Example 26

3-((1-(3-amino-1H-1,2,4-triazol-5-yl)piperidin-4-yl)(4-chlorophenethyl)-amino)propanoic acid The title compound was prepared as described for Example 2 in a manner described in Procedure 1A from N-Boc-piperid-4-one, (4-chlorophenyl)acetaldehyde, and methyl 3-aminopropanoate, followed by Procedure 2 and Procedure 3 for N-Boc-deprotection and triazole ring installation, respectively. The final hydrolysis of the methyl ester and purification of the title compound were accomplished in a manner similar to Example 1, Step 4.

$^1$H NMR (CD$_3$OD, 500 MHz) δ[ppm]: 7.33 (s, 4H), 3.99 (brd, 2H, J=13 Hz), 3.55-3.49 (m, 1H), 3.35-3.30 (m, 4H), 3.09-3.06 (m, 2H), 2.87-2.82 (m, 2H), 2.60-2.58 (m, 2H), 1.95 (brd, 2H, J=11.5 Hz), 1.84-1.76 (m, 2H).

ESI-MS for C$_{18}$H$_{25}$ClN$_6$O$_2$ calculated 392.89. found 393.2/395.2 (M+1), 391.3/393.3 (M−1).

| Ex # | Activity | Structure |
|---|---|---|
| 26 | D | 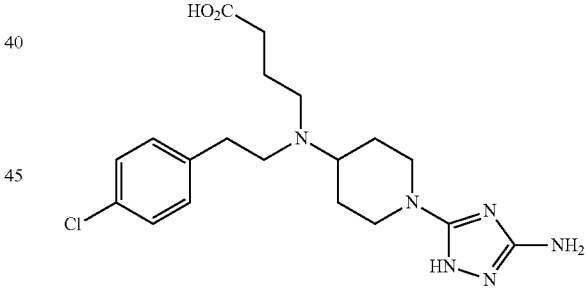 |

Example 27

4-((1-(3-amino-1H-1,2,4-triazol-5-yl)piperidin-4-yl)(4-chlorophenethyl)-amino)butanoic acid The title compound was prepared as described for Example 2 in a manner described in Procedure 1A from N-Boc-piperid-4-one, (4-chlorophenyl)acetaldehyde, and methyl 4-aminobutanoate followed by Procedure 2 and Procedure 3 for N-Boc-deprotection and triazole ring installation, respectively. The final hydrolysis of the methyl ester and purification of the title compound were accomplished in a manner similar to Example 2, Step 4.

$^1$H NMR (CD$_3$OD, 500 MHz) δ[ppm]: 7.33 (s, 4H), 4.00 (brd, 2H, J=13 Hz), 3.49-3.44 (m, 1H), 3.24-3.21 (m, 2H), 3.18-3.15 (m, 2H), 3.09-3.05 (m, 2H) 2.88-2.83 (m, 2H), 2.53-2.50 (m, 2H), 2.02 (br d, 2H, J=11 Hz), 1.96-1.92 (m, 2H), 1.84-1.75 (m, 2H).

ESI-MS for C$_{19}$H$_{27}$ClN$_6$O$_2$ calculated 406.92. found 407.2/409.2 (M+1), 405.3/407.3 (M−1).

| Ex # | Activity | Structure |
|---|---|---|
| 27 | C | ![structure] |

Example 28

3-((1-(3-amino-1H-1,2,4-triazol-5-yl)piperidin-4-yl)(4-chlorophenethyl)amino)-3-(4-chlorophenyl)propanoic acid

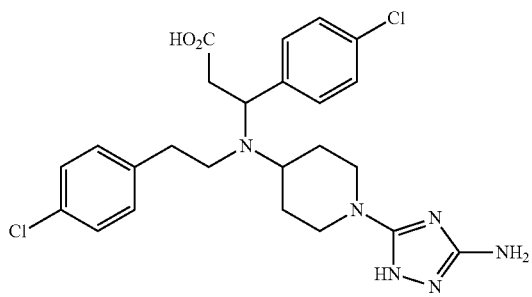 [SMILES: Nc1n[nH]c(N2CCC(N(CCc3ccc(Cl)cc3)C(CC(=O)O)c3ccc(Cl)cc3)CC2)n1]

The title compound was prepared as described for Example 2 in a manner described in Procedure 1A from N-Boc-piperid-4-one, (4-chlorophenyl)acetaldehyde, and methyl 3-amino-3-(4-chlorophenyl)propanoate, followed by Procedure 2 and Procedure 3 for N-Boc-deprotection and triazole ring installation, respectively. The final hydrolysis of the methyl ester and purification of the title compound were accomplished in a manner similar to Example 2, Step 4.

$^1$H NMR (DMSO-$d_6$+$D_2O$, 500 MHz) δ[ppm]: 7.60 (d, 2H, J=8.47 Hz), 7.46 (d, 2H, J=8.5 Hz), 7.24 (d, 2H, J=8 Hz), 6.99 (d, 2H, J=7.5 Hz), 4.76 (dd, 1H, J=4 Hz, J=10 Hz), 3.76 (d, 1H, J=12 Hz), 3.69 (d, 1H, J=12.8 Hz), 3.51-3.49 (m, 1H), 3.24-3.10 (m, 4H), 2.97-2.93 (m, 1H), 2.86-2.81 (m, 1H), 2.60-2.51 (m, 2H), 1.90 (d, 1H, J=11.67), 1.79-1.71 (m, 3H).

ESI-MS for $C_{24}H_{28}Cl_2N_6O_2$ calculated 503.44. found 502.9/504.9 (M+1), 501.2/503.2 (M−1).

| Ex # | Activity | Structure |
|---|---|---|
| 28 | D | ![structure] |

Example 29

3-((1-(3-amino-1H-1,2,4-triazol-5-yl)piperidin-4-yl)(4-chlorophenethyl)amino)-2-(4-chlorophenyl)propanoic acid

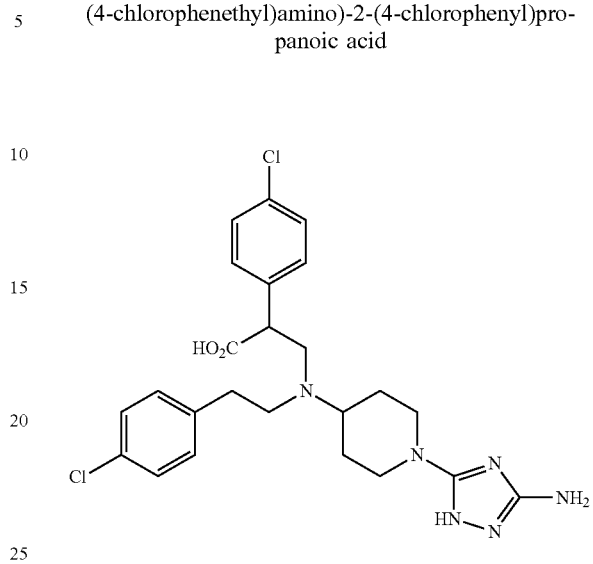

The title compound was prepared as described for Example 2 in a manner described in Procedure 1A from N-Boc-piperid-4-one, (4-chlorophenyl)acetaldehyde, and methyl 3-amino-2-(4-chlorophenyl)propanoate, followed by Procedure 2 and Procedure 3 for N-Boc-deprotection and triazole ring installation, respectively. The final hydrolysis of the methyl ester and purification of the title compound were accomplished in a manner similar to Example 2, Step 4.

$^1$H NMR (DMSO-$d_6$, 500 MHz) δ[ppm]: 7.31 (d, 2H, J=9 Hz), 7.30 (d, 2H, J=9 Hz), 7.22 (d, 2H, J=8 Hz), 4.08-4.05 (m, 1H), 3.90 (dd, 1H, J=9.5 Hz, J=13.5 Hz), 3.76 (m, 2H), 3.59-3.54 (m, 1H), 3.29-3.19 (m, 3H), 2.98-2.82 (m, 4H), 1.93 (d, 2H, J=10 Hz), 1.83-1.75 (m, 1H), 1.66-1.57 (m, 1H).

ESI-MS for $C_{24}H_{28}Cl_2N_6O_2$ calculated 503.44. found 503.1/505.1 (M+1), 501.3/503.3 (M−1).

| Ex # | Activity | Structure |
|---|---|---|
| 29 | B | ![structure] |

Example 30

1-(((1-(3-amino-1H-1,2,4-triazol-5-yl)piperidin-4-yl)(4-chlorophenethyl)amino)-methyl)cyclopropanecarboxylic acid

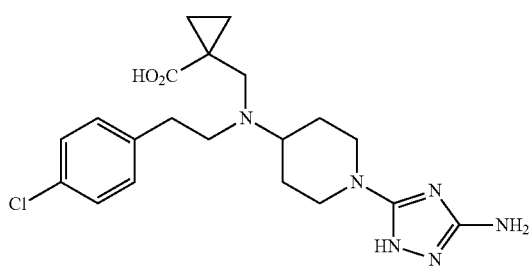 [SMILES: Nc1n[nH]c(N2CCC(N(CCc3ccc(Cl)cc3)CC3(C(=O)O)CC3)CC2)n1]

The title compound was prepared in a similar manner to Example 2, as described in Procedure 1A from N-Boc-piperid-4-one, (4-chlorophenyl)acetaldehyde, and methyl 1-(aminomethyl)cyclopropanecarboxylate followed by Procedure 2 and Procedure 3 for N-Boc-deprotection and triazole ring installation, respectively. The final hydrolysis of the methyl ester and purification of the title compound were accomplished in a manner similar to Example 1, Step 4.

$^1$H NMR (DMSO-d$_6$+D$_2$O, 500 MHz) δ[ppm]: 7.31 (d, 2H, J=8 Hz), 7.24 (d, 2H, J=8 Hz), 3.73 (d, 2H, J=12 Hz, 3.61-3.57 (m, 1H), 3.32 (t, 2H), 2.98-2.94 (m, 2H), 2.88 (m, 2H), 2.51-2.48 (m, 2H), 1.91 (d, 2H, J=12.80 Hz), 1.70 (br s, 2H), 1.30 (s, 2H), 1.04 (brs, 2H).

ESI-MS for C$_{20}$H$_{27}$ClN$_6$O$_7$ calculated 418.93. found 419.1/421.1 (M+1), 417.4/419.3 (M−1).

| Ex # | Activity | Structure |
|---|---|---|
| 30 | D | 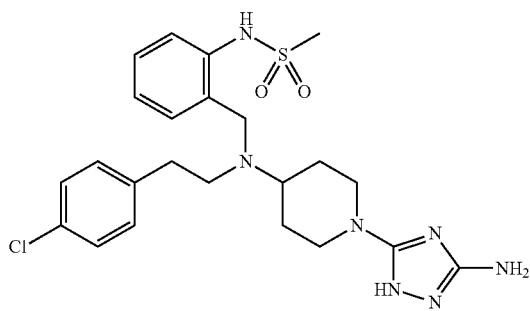 [SMILES: CS(=O)(=O)Nc1ccccc1CN(CCc1ccc(Cl)cc1)C1CCN(c2nc(N)n[nH]2)CC1] |

Example 31

N-(2-(((1-(3-amino-1H-1,2,4-triazol-5-yl)piperidin-4-yl)(4-chlorophenethyl)-amino)methyl)phenyl)methanesulfonamide The title compound was prepared as described for Example 15 in a manner described in Procedure 1A from N-Boc-piperid-4-one, (4-chlorophenyl)acetaldehyde, and 2-(methylsulfonylamino)benzylamine, followed by Procedure 2 and Procedure 3 for N-Boc-deprotection and triazole ring installation, respectively.

$^1$H NMR (CDCl$_3$, 500 MHz) δ[ppm]: 7.42 (d, 2H, J=8 Hz), 7.31-7.28 (m, 2H), 7.19 (s, 1H), 7.10 (d, 2H, J=8 Hz), 7.05-7.02 (m, 2H), 6.95 (s, 1H), 4.51 (br s, 2H), 3.96-3.93 (m, 4H), 3.78 (s, 3H), 2.78-2.72 (m, 3H) 1.86-1.84 (m, 4H), 1.72-1.65 (m, 4H).

ESI-MS for C$_{23}$H$_{30}$ClN$_7$O$_2$S calculated 504.06. found 504.1/506.0 (M+1), 502.2/504.2 (M−1).

| Ex # | Activity | Structure |
|---|---|---|
| 31 | B | 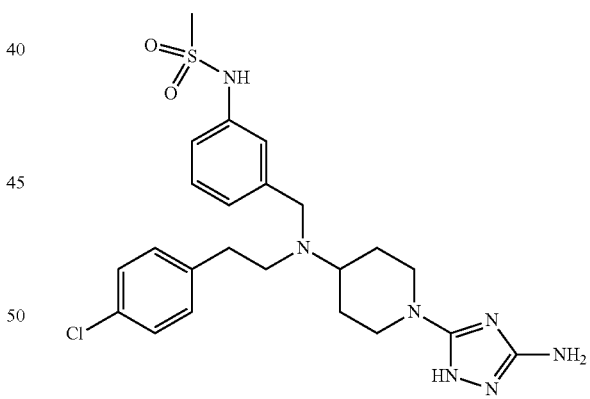 |

Example 32

N-(3-(((1-(3-amino-1H-1,2,4-triazol-5-yl)piperidin-4-yl)(4-chlorophenethyl)-amino)methyl)phenyl)methanesulfonamide The title compound was prepared as described for Example 15 in a manner described in Procedure 1A from N-Boc-piperid-4-one, (4-chlorophenyl)acetaldehyde, and 3-(methylsulfonylamino)benzylamine, followed by Procedure 2 and Procedure 3 for N-Boc-deprotection and triazole ring installation, respectively.

$^1$H NMR (CD$_3$OD, 500 MHz) δ[ppm]: 7.26 (s, 1H), 7.19 (t, 1H, J=8 Hz), 7.16 (d, 2H, J=8 Hz), 7.55 (d, 2H, J=8 Hz), 7.03 (m, 2H), 3.80 (m, 2H), 3.67 (s, 2H), 2.87 (s, 3H), 2.71-2.60 (m, 7H), 1.72 (m, 2H) 1.60 (m, 2H).

ESI-MS for C$_{23}$H$_{30}$ClN$_7$O$_2$S calculated 504.06. found 504.0/506.0 (M+1), 502.1/504.1 (M−1).

| Ex # | Activity | Structure |
|---|---|---|
| 32 | A | 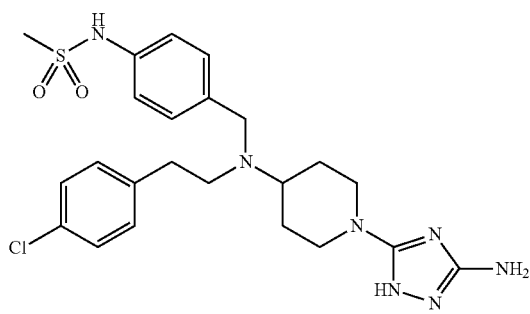 [SMILES: CS(=O)(=O)Nc1ccc(CN(CCc2ccc(Cl)cc2)C2CCN(c3nc(N)n[nH]3)CC2)cc1] |

Example 33

N-(4-(((1-(3-amino-1H-1,2,4-triazol-5-yl)piperidin-4-yl)(4-chlorophenethyl)-amino)methyl)phenyl)methanesulfonamide

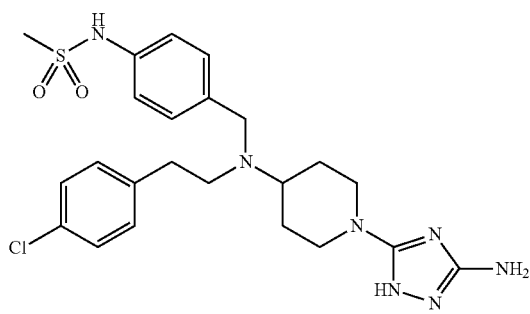 [SMILES: CS(=O)(=O)Nc1ccc(CN(CCc2ccc(Cl)cc2)C2CCN(c3nc(N)n[nH]3)CC2)cc1]

The title compound was prepared as described for Example 15 in a manner described in Procedure 1A from N-Boc-piperid-4-one, (4-chlorophenyl)acetaldehyde, and 4-(methylsulfonylamino)benzylamine, followed by Procedure 2 and Procedure 3 for N-Boc-deprotection and triazole ring installation, respectively.

$^1$H NMR (CD$_3$OD, 500 MHz) δ[ppm]: 7.60 (d, 2H, J=10 Hz), 7.56 (d, 2H, J=10 Hz), 7.50 (d, 2H, J=10 Hz), 7.42 (d, 2H, J=10 Hz), 4.23-4.20 (m, 2H), 4.03 (s, 2H), 3.28 (s, 3H), 3.10-2.99 (m, 7H), 2.12 (m, 2H), 1.91 (m, 2H).

ESI-MS for $C_{23}H_{30}ClN_7O_2S$ calculated 504.06. found 504.1/506.0 (M+1), 502.2/504.2 (M−1).

| Ex # | Activity | Structure |
|---|---|---|
| 33 | A | 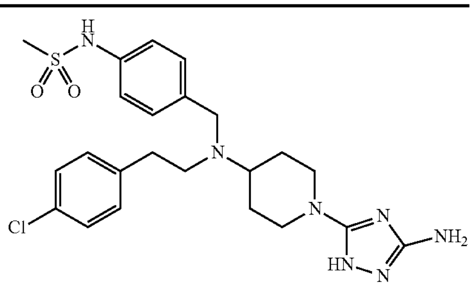 |

Example 34

4-(((1-(3-amino-1H-1,2,4-triazol-5-yl)piperidin-4-yl)(4-bromophenethyl)-amino)methyl)benzamide

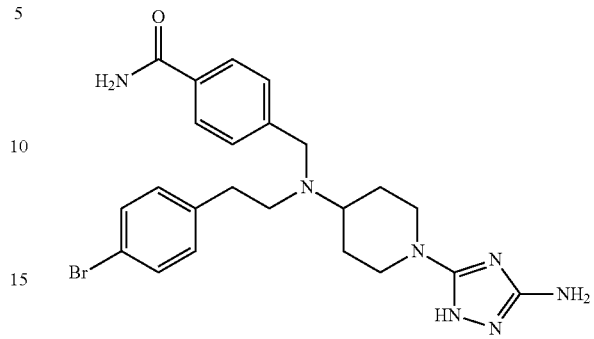

The title compound was prepared as described for Example 15 in a manner described in Procedure 1A from N-Boc-piperid-4-one, (4-bromophenyl)acetaldehyde, and 4-(aminomethyl)benzamide in the reductive amination, followed by Procedure 2 and Procedure 3 for N-Boc-deprotection and triazole ring installation, respectively.

$^1$H NMR (DMSO-d$_6$, 500 MHz) δ[ppm]: 10.88 (brs, 1H), 7.86 (brs, 1H), 7.73 (d, J$_{AB}$=8.2 Hz, 2H), 7.38 (d, J$_{AB}$=8.2 Hz, 2H), 7.28 (d, J$_{AB}$=8.2 Hz, 2H), 7.25 (brs, 1H), 7.06 (d, J$_{AB}$=8.2 Hz, 2H), 5.54 (brs, 2H), 3.80-3.73 (m, 2H), 3.66 (s, 2H), 2.65-2.54 (m, 6H), 2.52-2.48 (m, 1H), 1.63-1.56 (m, 2H), 1.44-1.35 (m, 2H).

ESI-MS for $C_{23}H_{28}BrN_7O$ calculated 498.43. found 498.1/500.1 (M+1), 496.2/498.2 (M−1).

| Ex # | Activity | Structure |
|---|---|---|
| 34 | A | 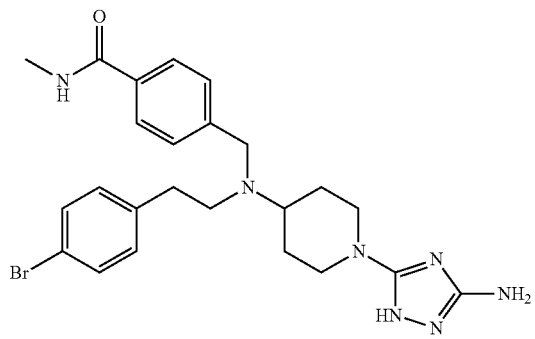 [SMILES: CNC(=O)c1ccc(CN(CCc2ccc(Br)cc2)C2CCN(c3nc(N)n[nH]3)CC2)cc1] |

Example 35

4-(((1-(3-amino-1H-1,2,4-triazol-5-yl)piperidin-4-yl)(4-bromophenethyl)-amino)methyl)-N-methylbenzamide

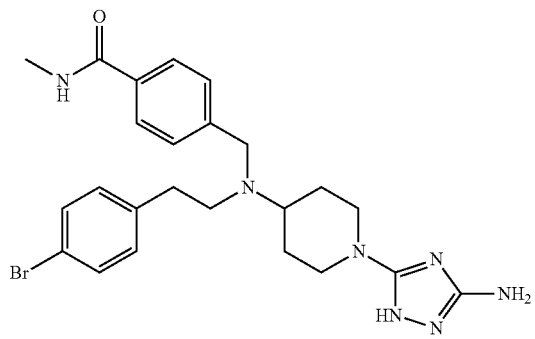 [SMILES: CNC(=O)c1ccc(CN(CCc2ccc(Br)cc2)C2CCN(c3nc(N)n[nH]3)CC2)cc1]

The title compound was prepared as described for Example 15 in a manner disclosed in Procedure 1A from N-Boc-piperid-4-one, (4-bromophenyl)acetaldehyde, and 4-(aminomethyl)-N-methylbenzamide in the reductive amination, followed by Procedure 2 and Procedure 3 for N-Boc-deprotection and triazole ring installation, respectively.

$^1$H NMR (DMSO-d$_6$, 500 MHz) δ[ppm]: 10.89 (brs, 1H), 8.36-8.30 (m, 1H), 7.68 (d, J$_{AB}$=8.0 Hz, 2H), 7.37 (d, J$_{AB}$=8.2 Hz, 2H), 7.28 (d, J$_{AB}$=8.0 Hz, 2H), 7.06 (d, J$_{AB}$=8.2 Hz, 2H), 5.45 (brs, 1H), 3.81-3.75 (m, 2H), 3.67 (s, 2H), 2.73 (d, J=4.5 Hz, 3H), 2.66-2.55 (m, 5H), 2.53-2.48 (m, 2H), 1.65-1.58 (m, 2H), 1.46-1.36 (m, 2H).

ESI MS for C$_{24}$H$_{30}$BrN$_7$O calculated 512.46. found 512.2/514.2 (M+1), 510.3/512.4 (M−1).

| Ex # | Activity | Structure |
|---|---|---|
| 35 | A | 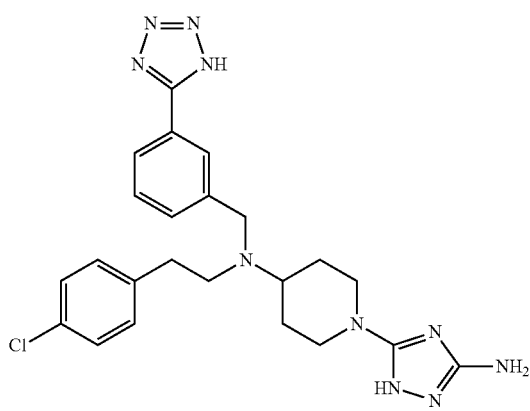 [SMILES: Nc1n[nH]c(N2CCC(N(CCc3ccc(Cl)cc3)Cc3cccc(-c4nnn[nH]4)c3)CC2)n1] |

Example 36

N-(3-(1H-tetrazol-5-yl)benzyl)-1-(3-amino-1H-1,2,4-triazol-5-yl)-N-(4-chlorophenethyl)piperidin-4-amine Step 1: tert-Butyl 4-((4-chlorophenethyl)(3-cyanobenzyl)amino)piperidine-1-carboxylate

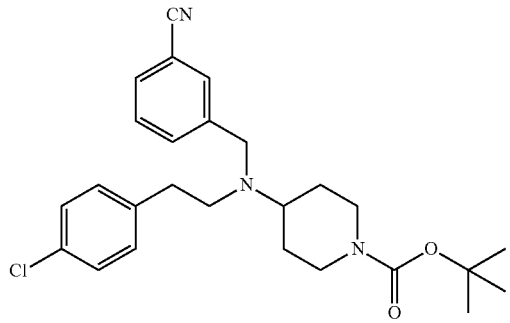 [SMILES: CC(C)(C)OC(=O)N1CCC(N(CCc2ccc(Cl)cc2)Cc2cccc(C#N)c2)CC1]

The title compound was obtained in a manner described in Procedure 1B from N-Boc-piperid-4-one, 2-(4-chlorophenyl)ethylamine, and methyl 3-formylbenzonitrile.

Step 2: tert-Butyl 4-((3-(1H-tetrazol-5-yl)benzyl)(4-chlorophenethyl)amino)piperidine-1-carboxylate

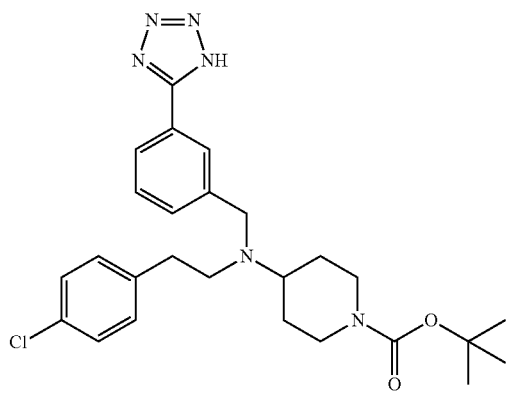 [SMILES: CC(C)(C)OC(=O)N1CCC(N(CCc2ccc(Cl)cc2)Cc2cccc(-c3nnn[nH]3)c2)CC1]

tert-Butyl 4-((4-chlorophenethyl)(3-cyanobenzyl)amino) piperidine-1-carboxylate obtained in Step 1 was dissolved in toluene (5 mL/mmol) and sodium azide (3 equiv) and triethylamine hydrochloride (0.1 equiv) were added to this solution. The heterogeneous mixture was refluxed for 3 days after which time the starting material could no longer be detected. After cooling down to ambient temperature the solids were filtered off and the solvent was stripped off in vacuo. The crude product was purified by silica gel chromatography (yield 60%).

Steps 3-4: 1-(3-amino-1H-1,2,4-triazol-5-yl)-N-[3-(2H-tetrazol-5-yl)benzyl]-N-[2-(4-chlorophenyl)ethyl]piperidin-4-amine tert-Butyl 4-((3-(1H-tetrazol-5-yl)benzyl)(4-chlorophenethyl)amino)piperidine-1-carboxylate obtained in Step 2 was subjected to the N-Boc-deprotection followed by triazole ring formation as described in Procedure 2 and Procedure 3 respectively to provide the title compound.

$^1$H NMR (DMSO-d$_6$+D$_2$O, 500 MHz) δ[ppm]: 8.20 (s, 1H), 8.05 (d, 1H, J=7.7 Hz), 7.67-7.73 (m, 2H), 7.25 (d, 2H, J$_{AA'BB'}$=7.8 Hz), 7.12 (d, 2H, J$_{AA'BB'}$=7.7 Hz), 4.48 (s, 2H), 3.86 (brd, 2H, J=11.7 Hz), 3.55-3.60 (m, 1H), 3.20-3.23 (m, 2H), 2.82-2.87 (m, 4H), 2.12 (brd, 2H, J=10.5 Hz), 1.77-1.85 (m, 2H).

ESI-MS for $C_{23}H_{27}ClN_{10}$ calculated 478.99. found 479.0/481.0 (M+1), 477.2/479.3 (M−1).

| Ex # | Activity | Structure |
|---|---|---|
| 36 | A | 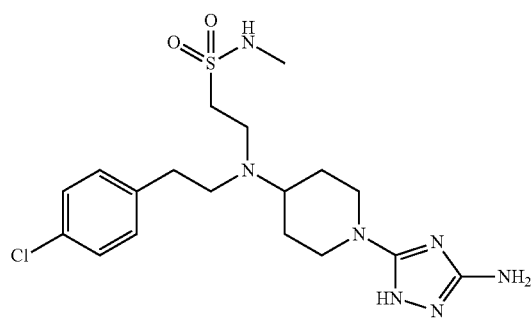 [SMILES: CNS(=O)(=O)CCN(CCc1ccc(Cl)cc1)C1CCN(c2nc(N)n[nH]2)CC1] |

Example 37

2-((1-(3-amino-1H-1,2,4-triazol-5-yl)piperidin-4-yl)(4-chlorophenethyl)amino)-N-methylethanesulfonamide The title compound was prepared as described for Example 15 in a manner disclosed in Procedure 1A from N-Boc-piperid-4-one, (4-chlorophenyl)acetaldehyde, and 2-amino-N-methylethanesulfonamide in the reductive amination, followed by Procedure 2 and Procedure 3 for N-Boc-deprotection and triazole ring installation, respectively.

$^1$H NMR (CDCl$_3$, 500 MHz) δ[ppm]: 7.24 (d, 2H, J$_{AA'BB'}$=8.3 Hz), 7.09 (d, 2H, J$_{AA'BB'}$=8.3 Hz), 5.52 (brs, 1H), 3.85 (d, 2H, J=11.1 Hz), 2.99-3.01 (m, 2H), 2.92-2.93 (m, 2H), 2.61-2.75 (m, 10H), 1.65 (brd, 2H, J=10.9 Hz), 1.46-1.51 (m, 2H).

ESI MS for $C_{18}H_{28}ClN_7O_2S$ calculated 441.99. found 442.1/444.0 (M+1), 440.3/442.3 (M−1).

| Ex # | Activity | Structure |
|---|---|---|
| 37 | B | 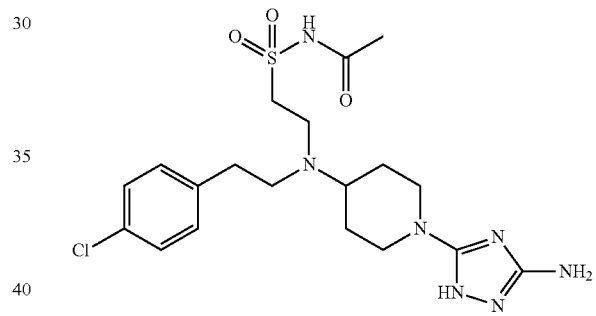 |

Example 38

N-((2-((1-(3-amino-1H-1,2,4-triazol-5-yl)piperidin-4-yl)(4-chlorophenethyl)-amino)ethyl)sulfonyl)acetamide Step 1: tert-butyl 4-((4-chlorophenethyl)(2-sulfamoylethyl)amino)piperidine-1-carboxylate

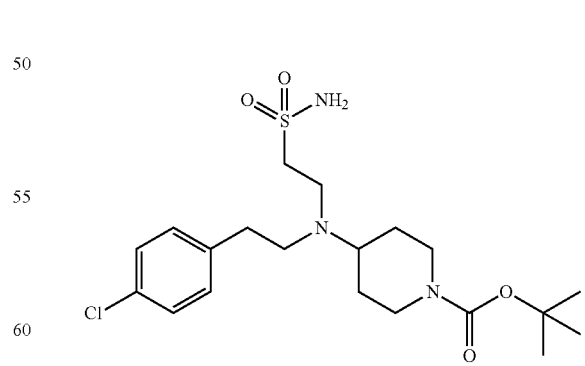

The title compound was obtained in a manner described in Procedure 1A from N-Boc-piperid-4-one, 2-(4-chlorophenyl)acetaldehyde, and 2-aminoethanesulfonamide.

Step 2: tert-butyl 4-((2-(N-acetylsulfamoyl)ethyl)(4-chlorophenethyl)amino)piperidine-1-carboxylate

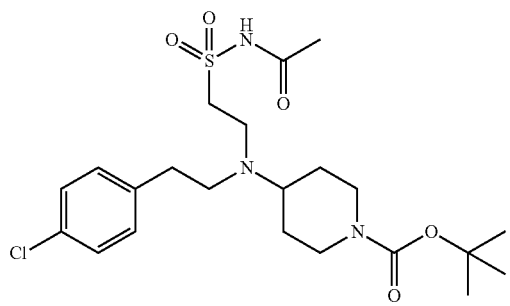 [SMILES: CC(=O)NS(=O)(=O)CCN(CCc1ccc(Cl)cc1)C1CCN(C(=O)OC(C)(C)C)CC1]

The title compound was obtained by acetylation of the sulfonamide group in a manner described for Example 16, Step 1.

Steps 3-4: 1-(3-amino-1H-1,2,4-triazol-5-yl)-N-{2-[(acetylamino)sulfonyl]ethyl}-N-[2-(4-chlorophenyl)ethyl]piperidin-4-amine tert-Butyl 4-((2-(N-acetylsulfamoyl)ethyl)(4-chlorophenethyl)amino)piperidine-1-carboxylate obtained in Step 2 was subjected to the N-Boc-deprotection followed by triazole ring formation as described in Procedure 2 and Procedure 3 respectively, to provide the title compound.

$^1$H NMR (DMSO-d$_6$+D$_2$O, 500 MHz) δ[ppm]: 7.29 (d, 2H, J$_{AA'BB'}$=7.7 Hz), 7.22 (d, 2H, J$_{AA'BB'}$=7.7 Hz), 3.75 (brd, 2H, J=12.6 Hz), 3.35-3.37 (m, 2H), 2.92-2.95 (m, 2H), 2.60-2.70 (m, 7H), 1.92 (brs, 3H), 1.65 (brd, 2H, J=10.9 Hz), 1.29-1.36 (m, 2H).

ESI-MS for C$_{19}$H$_{28}$ClN$_7$O$_3$S calculated 470.00. found 470.0/472.0 (M+1), 468.3/470.3 (M−1).

| Ex # | Activity | Structure |
|---|---|---|
| 38 | B | 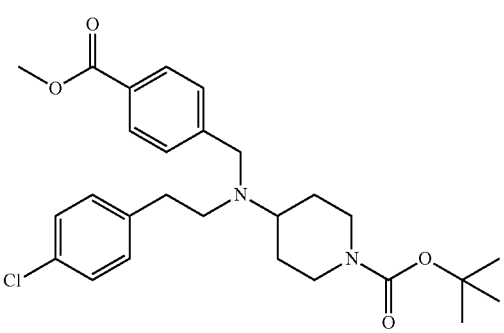 [SMILES: COC(=O)c1ccc(CN(CCc2ccc(Cl)cc2)C2CCN(C(=O)OC(C)(C)C)CC2)cc1] |

Example 39

4-(((1-(3-amino-1H-1,2,4-triazol-5-yl)piperidin-4-yl)(4-chlorophenethyl)-amino)methyl)-N-(methylsulfonyl)benzamide

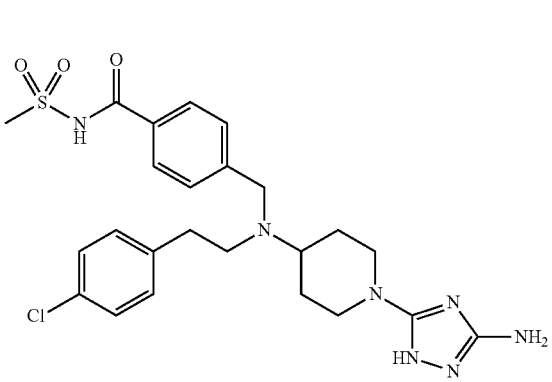 [SMILES: CS(=O)(=O)NC(=O)c1ccc(CN(CCc2ccc(Cl)cc2)C2CCN(c3nc(N)n[nH]3)CC2)cc1]

Step 1: tert-Butyl 4-((4-chlorophenethyl)(4-(methoxycarbonyl)benzyl)amino)piperidine-1-carboxylate

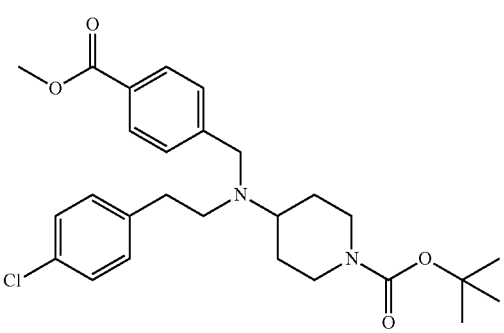 [SMILES: COC(=O)c1ccc(CN(CCc2ccc(Cl)cc2)C2CCN(C(=O)OC(C)(C)C)CC2)cc1]

The title compound was prepared according to Procedure 1B starting from N-Boc-piperid-4-one, 2-(4-chlorophenyl)ethylamine, and methyl 4-formylbenzoate.

Step 2: 4-(((1-(tert-butoxycarbonyl)piperidin-4-yl)(4-chlorophenethyl)amino)methyl)benzoic acid

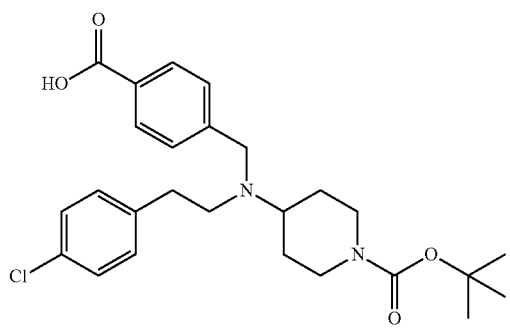 [SMILES: CC(C)(C)OC(=O)N1CCC(N(CCc2ccc(Cl)cc2)Cc2ccc(C(=O)O)cc2)CC1]

tert-Butyl 4-((4-chlorophenethyl)(4-(methoxycarbonyl)benzyl)amino)piperidine-1-carboxylate obtained in Step 1 was dissolved in MeOH (5 mL/mmol), NaOH (5 eqs) (as a 0.5 N aqueous solution) was added and the reaction mixture was stirred at room temperature for 15 hours.). pH of the reaction was made neutral by careful addition of 0.5 N HCl, and methanol was removed in vacuo. The precipitated product was filtered off, washed several times with acetone/diethyl ether mixture (1:2 v/v) and dried in the air. It was found to be of sufficient purity to be used in the next step without further purification.

Step 3: tert-Butyl-4-((4-chlorophenethyl)(4-((methylsulfonyl)carbamoyl)benzyl)amino)-piperidine-1-carboxylate

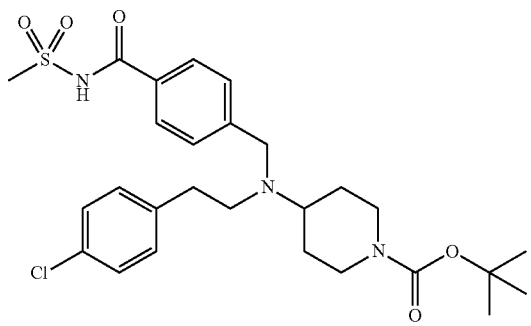 [SMILES: CC(C)(C)OC(=O)N1CCC(N(CCc2ccc(Cl)cc2)Cc2ccc(C(=O)NS(C)(=O)=O)cc2)CC1]

4-(((1-(tert-Butoxycarbonyl)piperidin-4-yl)(4-chlorophenethyl)amino)methyl)benzoic acid synthesized in Step 2 was dissolved in DCM (5 mL/mmol) and DIPEA (3 equiv) and methanesulfonamide (2 eqs) were added. The reaction mixture was cooled to 0° C. and TFFH (1.2 eq) was added in one portion. The reaction mixture was stirred at 0° C. for 6 hours and then for 15 hours at room temperature. Ethyl acetate (15 mL/mmol) was added and the solution was washed sequentially with 5% citric acid (2×), 5% NaHCO$_3$ (2×) and brine (2×) and was dried over MgSO$_4$. The drying agent was filtered off and the solvents were evaporated in vacuo. The crude product was purified by silica gel chromatography.

Steps 4-5: 1-(3-amino-1H-1,2,4-triazol-5-yl)-N-{[4-N-(methylsulfonyl)benzamido]methyl}-N-[2-(4-chlorophenyl)ethyl]piperidin-4-amine tert-Butyl 4-((4-chlorophenethyl)(4-((methylsulfonyl)carbamoyl)benzyl)amino)-piperidine-1-carboxylate obtained in Step 3 was subjected to the N-Boc-deprotection followed by triazole ring formation as described in Procedure 2 and Procedure 3 respectively, to provide the title compound.

$^1$H NMR (DMSO-d$_6$+D$_2$O, 500 MHz) δ[ppm]: 7.89 (d, 2H, J$_{AA'BB'}$=7.5 Hz), 7.45 (d, 2H, J$_{AA'BB'}$=7.5 Hz), 7.25 (d, 2H, J$_{AA'BB'}$=8.3 Hz), 7.08 (d, 2H, J$_{AA'BB'}$=8.5 Hz), 4.24 (brs, 2H), 3.81 (brd, 2H, J=11.9 Hz), 3.30-3.35 (m, 1H), 3.02-3.05 (m, 2H), 2.95 (s, 3H), 2.72-2.75 (m, 2H), 2.63-2.68 (m, 2H), 1.95-1.97 (m, 2H), 1.63-1.67 (m, 2H).

ESI-MS for C$_{24}$H$_{30}$ClN$_7$O$_3$S calculated 532.07. found 532.1/534.1 (M+1), 530.3/532.1 (M−1).

| Ex # | Activity | Structure |
|---|---|---|
| 39 | A | (structure) |

Example 40

3-(((1-(3-amino-1H-1,2,4-triazol-5-yl)piperidin-4-yl)(4-chlorophenethyl)amino)-methyl)-N-(methylsulfonyl)benzamide The title compound was prepared exactly in the same manner as Example 38 (all steps) starting from N-Boc-piperid-4-one, 2-(4-chlorophenyl)ethylamine, and methyl 3-formylbenzoate.

$^1$H NMR (DMSO-d$_6$+D$_2$O, 500 MHz) δ[ppm]: 7.95 (s, 1H), 7.81 (d, 1H, J=7.3 Hz), 7.37 (d, 1H, J=6.2 Hz), 7.30 (d, 1H, J=7.3 Hz), 7.26 (d, 2H, J$_{AA'BB'}$=8.3 Hz), 7.14 (d, 2H, J$_{AA'BB'}$=8.3 Hz), 3.79-3.85 (m, 4H), 2.91 (s, 3H), 2.52-2.77 (m, 7H), 1.75-1.77 (m, 2H), 1.47-1.50 (m, 2H).

ESI-MS for C$_{24}$H$_{30}$ClN$_7$O$_3$S calculated 532.07. found 532.1/534.1 (M+1), 530.2/532.2 (M−1).

| Ex # | Activity | Structure |
|---|---|---|
| 40 | A | (structure) |

Example 41

5-(((1-(3-amino-1H-1,2,4-triazol-5-yl)piperidin-4-yl)(4-chlorophenethyl)amino)-methyl)-2-chloro-N-(methylsulfonyl)benzamide

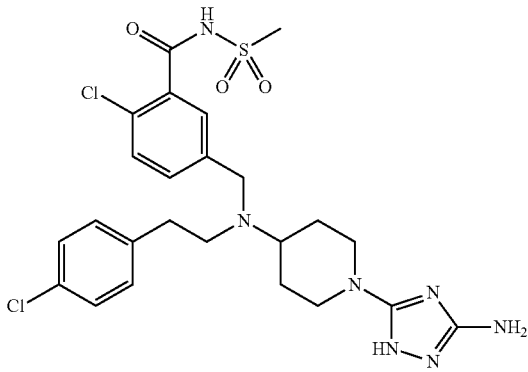 [SMILES: CS(=O)(=O)NC(=O)c1cc(CN(CCc2ccc(Cl)cc2)C2CCN(c3nc(N)n[nH]3)CC2)ccc1Cl]

The title compound was prepared exactly in the same manner as Example 38 (all steps) starting from N-Boc-piperid-4-one, 2-(4-chlorophenyl)ethylamine, and methyl 2-chloro-5-formylbenzoate.

$^1$H NMR (DMSO-d$_6$, 500 MHz) δ[ppm]: 9.85 (brs, 1H), 7.80 (brs, 1H), 7.69 (brs, 1H), 7.64 (brs, 1H), 7.33 (d, J=7.6 Hz, 2H), 7.20 (d, J=7.6 Hz, 2H), 4.55 (brs, 1H), 4.34 (brs, 1H), 3.82 (brs, 2H), 3.61 (brs, 2H), 3.35 (s, 3H), 3.29-3.12 (m, 2H), 2.90 (brs, 3H), 2.77 (brs, 1H), 2.10 (brs, 2H), 1.81 (brs, 2H).

ESI-MS for C$_{24}$H$_{29}$Cl$_2$N$_7$O$_3$S calculated 566.51. found 566.1/568.1 (M+1), 564.3/566.3 (M-1).

| Ex # | Activity | Structure |
|---|---|---|
| 41 | B | 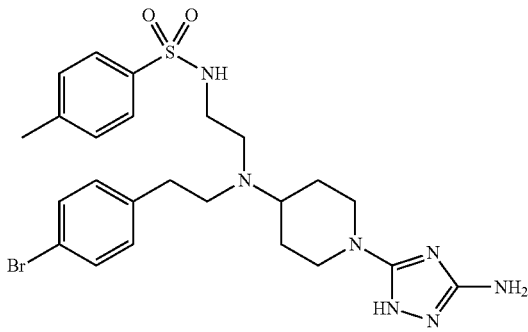 [SMILES: Cc1ccc(S(=O)(=O)NCCN(CCc2ccc(Br)cc2)C2CCN(c3nc(N)n[nH]3)CC2)cc1] |

Example 42

N-(2-((1-(3-amino-1H-1,2,4-triazol-5-yl)piperidin-4-yl)(4-bromophenethyl)-amino)ethyl)-4-methylbenzenesulfonamide The title compound was prepared as described for Example 14 in a manner disclosed in Procedure 1A from N-Boc-piperid-4-one, (4-bromophenyl)acetaldehyde, and N-(2-aminoethyl)-4-methylbenzenesulfonamide in reductive amination step followed by Procedure 2 and Procedure 3 for N-Boc-deprotection and triazole ring installation, respectively.

$^1$H NMR (CDCl$_3$, 500 MHz) δ[ppm]: 7.68 (d, 2H, J=10 Hz), 7.37 (d, 2H, J=10 Hz), 7.28 (d, 2H, J=10 Hz), 6.92 (d, 2H, J=10 Hz), 5.03 (br s, 1H), 4.45 (br s, 2H), 3.48 (s, 1H), 2.83-2.81 (m, 2H), 2.73-2.68 (m, 2H), 2.56-2.47 (m, 7H), 2.39 (s, 3H), 1.59-1.56 (m, 2H), 1.47-1.40 (m, 2H), 1.39-1.37 (m, 2H).

ESI-MS for C$_{24}$H$_{32}$BrN$_7$O$_2$S calculated 562.54. found 562.1/564.1 (M+1), 560.2/562.2 (M-1).

| Ex # | Activity | Structure |
|---|---|---|
| 42 | A | 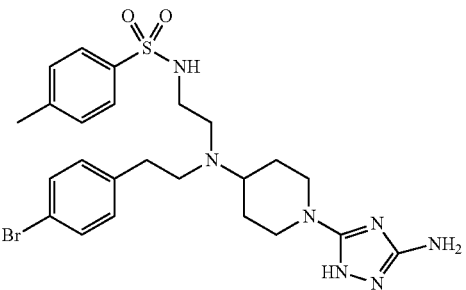 [SMILES: Cc1ccc(S(=O)(=O)NCCN(CCc2ccc(Br)cc2)C2CCN(c3nc(N)n[nH]3)CC2)cc1] |

Example 43

N-((1H-tetrazol-5-yl)methyl)-1-(3-amino-1H-1,2,4-triazol-5-yl)-N-(4-chlorophenethyl)piperidin-4-amine

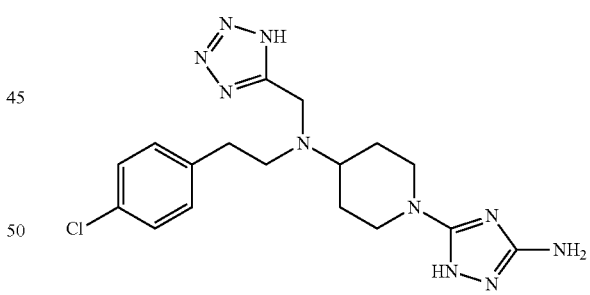

The title compound was prepared as described for Example 15 in a manner disclosed in Procedure 1A from N-Boc-piperid-4-one, (4-chlorophenyl)acetaldehyde, and (1H-tetrazol-5-ylmethyl)amine in reductive amination step followed by Procedure 2 and Procedure 3 for N-Boc-deprotection and triazole ring installation, respectively.

$^1$H NMR (DMSO-d$_6$+D$_2$O, 500 MHz) δ[ppm]: 7.30 (d, 2H, J$_{AA'BB'}$=8.1 Hz), 7.20 (d, 2H, J$_{AA'BB'}$=8.1 Hz), 4.44 (s, 2H), 3.77 (brd, 2H, J=12.4 Hz), 3.24-3.29 (m, 1H), 3.09-3.14 (m, 2H), 2.82-2.86 (m, 2H), 2.79 (t, 2H, J=12.2 Hz), 2.00 (brd, 2H, J=10.9 Hz), 1.57-1.64 (m, 2H).

ESI-MS for C$_{17}$H$_{23}$ClN$_{10}$ calculated 402.89. found 403.1/405.1 (M+1), 401.3/405.3 (M-1).

| Ex # | Activity | Structure |
|---|---|---|
| 43 | B | 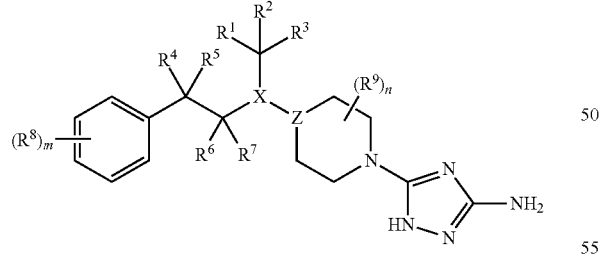 |

INCORPORATION BY REFERENCE

All U.S. patents, U.S. published patent applications, and PCT published patent applications designating the U.S. mentioned herein are hereby incorporated by reference in their entirety as if each individual publication or patent was specifically and individually indicated to be incorporated by reference. In case of conflict, the present application, including any definitions herein, will control.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound represented by formula (I) or a pharmaceutically acceptable salt thereof:

(I)

wherein:
X is N, and Z is CR$^{10}$; or X is CR$^{11}$, and Z is N;
R$^1$ is selected from the group consisting of Y, aryl substituted by Y, and alkyl substituted by Y;
Y is —CO$_2$H, —C(O)O(C$_1$-C$_6$)alkyl, —C(O)N(H)OH, —C(O)N(H)CN, —C(O)NH$_2$, —C(O)NH((C$_1$-C$_6$)alkyl), —C(O)N((C$_1$-C$_6$)alkyl)$_2$, —C(O)NH(aryl), —C(O)N(aryl)((C$_1$-C$_6$)alkyl), —C(O)N(aryl)$_2$, —C(O)NH((C$_1$-C$_6$)haloalkyl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)(C$_1$-C$_6$)alkyl, —S(O)$_2$NHC(O)(C$_1$-C$_6$)haloalkyl, —S(O)$_2$NHC(O)aryl, —N(H)S(O)$_2$(C$_1$-C$_6$)alkyl, —N(H)S(O)$_2$aryl, N(H)S(O)$_2$(C$_1$-C$_6$)haloalkyl, —NHC(O)((C$_1$-C$_6$)alkyl), —NHC(O)((C$_1$-C$_6$)haloalkyl), —NHC(O)(aryl), —NHC(O)NH(C$_1$-C$_6$)alkyl, —NHC(O)NHaryl, —C(O)N(H)S(O)$_2$(C$_1$-C$_6$)alkyl, —C(O)N(H)S(O)$_2$aryl, C(O)N(H)S(O)$_2$((C$_1$-C$_6$)haloalkyl), —P(O)(OH)$_2$,

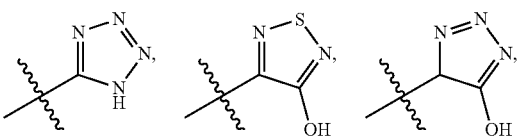

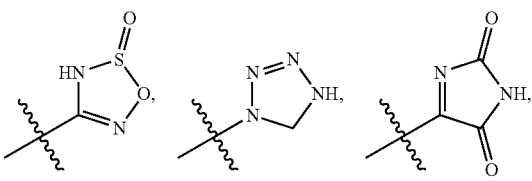

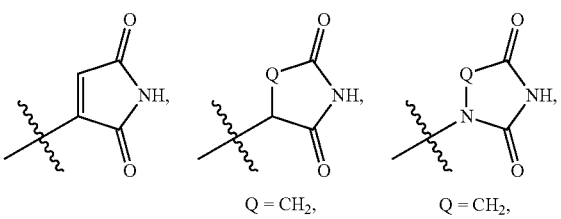

Q = CH$_2$, NH, S, O       Q = CH$_2$, NH, S, O

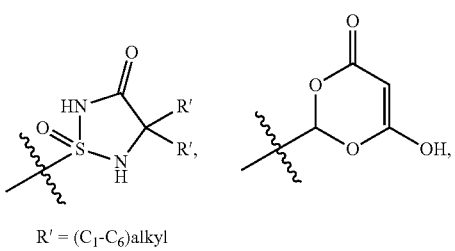

R' = (C$_1$-C$_6$)alkyl

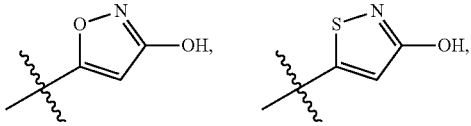

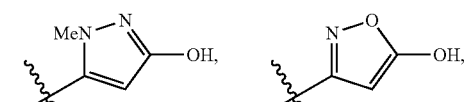

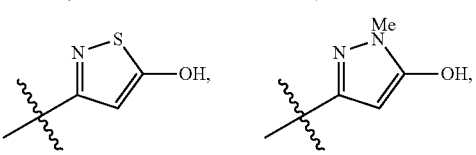

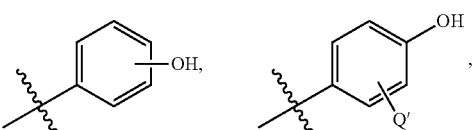

Q' = F, Cl, Br

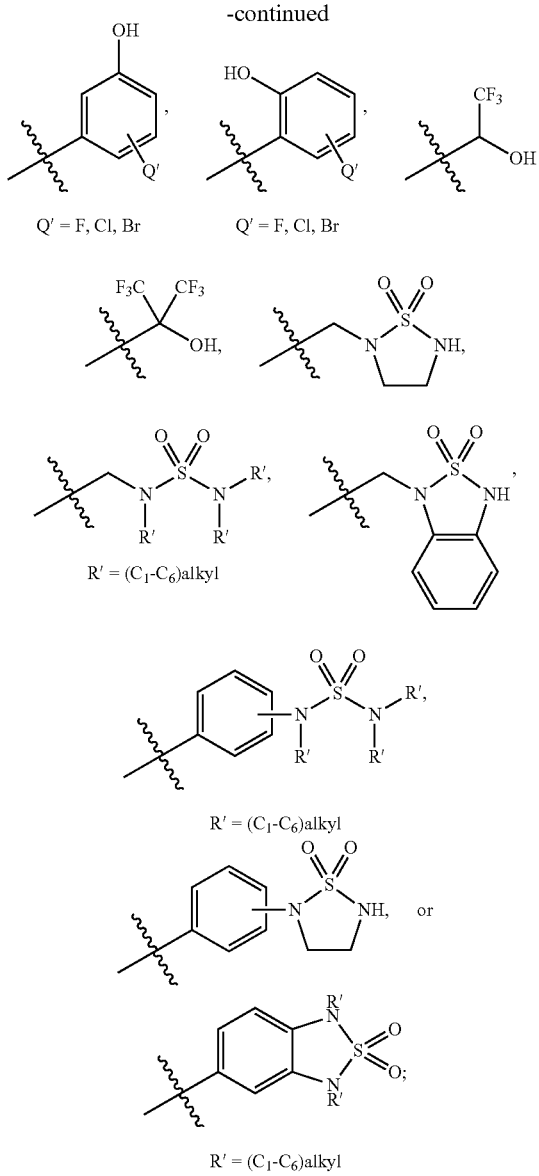

$R^2$, $R^3$, $R^4$, $R^5$, $R^6$, and $R^7$ are each independently H, $(C_1-C_6)$alkyl, aryl$(C_1-C_6)$alkyl, or aryl; or $R^2$, taken together with $R^6$ or $R^7$, forms a 5- or 6-membered ring;

$R^8$ is selected from the group consisting of halo, $(C_1-C_6)$alkyl, $(C_1-C_6)$haloalkyl, and $(C_3-C_6)$cycloalkyl;

$R^9$ is selected from the group consisting of OH, $(C_1-C_6)$alkyl, $(C_3-C_6)$cycloalkyl, aryl$(C_1-C_6)$alkyl, aryl, $(C_1-C_6)$alkoxyl, $(C_1-C_6)$haloalkyl, $(C_1-C_6)$hydroxyalkyl, heteroaryl, and heteroaryl$(C_1-C_6)$alkyl;

$R^{10}$ and $R^{11}$ are each independently selected from H and $(C_1-C_6)$alkyl;

m is an integer from 0-5;

n is an integer from 0-2;

further wherein any occurrence of $(C_1-C_6)$alkyl, aryl$(C_1-C_6)$alkyl, aryl, $(C_3-C_6)$cycloalkyl, $(C_1-C_6)$alkoxyl, $(C_1-C_6)$haloalkyl, $(C_1-C_6)$hydroxyalkyl, heteroaryl, or heteroaryl$(C_1-C_6)$alkyl is optionally and independently substituted by one or more substituents selected from the group consisting of halo, $(C_1-C_6)$alkyl, $(C_1-C_6)$haloalkyl, aryl, —$NH_2$, —$NH((C_1-C_6)$alkyl$)$, —$N((C_1-C_6)$alkyl$)_2$, —OH, $(C_3-C_6)$cycloalkyl, $(C_1-C_6)$alkoxyl, $(C_1-C_6)$haloalkoxyl, —SH, —$S((C_1-C_6)$alkyl$)$, $(C_1-C_6)$hydroxyalkyl, and $(C_1-C_6)$alkoxy$(C_1-C_6)$alkyl, —CN, —$CF_3$, —$C(O)NH_2$, —$C(O)NH(R^{12})$, —$C(O)N(R^{12})_2$, —$N(H)C(O)(R^{12})$, —$N(R^{12})C(O)(R^{12})$, —$S(O)_2NH_2$, —$S(O)_2NH(R^{12})$, —$S(O)_2N(R^{12})_2$, —$N(H)S(O)_2(R^{12})$, —$N(R^{12})S(O)_2(R^{12})$, —$NHC(O)NH_2$, —$NHC(O)NH(R^{12})$, and —$NHC(O)N(R^{12})_2$; and each occurrence of $R^{12}$ is independently selected from the group consisting of $(C_1-C_6)$alkyl$)$, aryl, and aryl$(C_1-C_6)$alkyl.

2. The compound of claim 1, wherein $R^1$ is Y.

3. The compound of claim 1, wherein $R^1$ is aryl substituted by Y.

4. The compound of claim 1, wherein $R^1$ is $(C_1-C_6)$alkyl substituted by Y.

5. The compound of claim 1, wherein Y is —$CO_2H$, —$C(O)NH_2$, —$C(O)NH(C_1-C_6)$alkyl, —$C(O)N((C_1-C_6)$alkyl$)_2$, —$C(O)NH(aryl)$, $C(O)N(aryl)((C_1-C_6)$alkyl$)$, $C(O)N(aryl)_2$, —$C(O)NH((C_1-C_6)$haloalkyl$)$, —$S(O)_2NH_2$, —$S(O)_2NH((C_1-C_6)$alkyl$)$, —$S(O)_2NH((C_1-C_6)$haloalkyl$)$, —$S(O)_2NH(aryl)$, —$S(O)_2NHC(O)(C_1-C_6)$alkyl, —$S(O)_2NHC(O)(C_1-C_6)$haloalkyl, —$S(O)_2NHC(O)aryl$, —$N(H)S(O)_2(C_1-C_6)$alkyl, —$N(H)S(O)_2aryl$, —$N(H)S(O)_2(C_1-C_6)$haloalkyl, —$NHC(O)((C_1-C_6)$alkyl$)$, —$NHC(O)((C_1-C_6)$haloalkyl$)$, —$NHC(O)(aryl)$, —$NHC(O)NH(C_1-C_6)$alkyl, —$NHC(O)NHaryl$, —$C(O)N(H)S(O)_2(C_1-C_6)$alkyl, —$C(O)N(H)S(O)_2aryl$, $C(O)N(H)S(O)_2((C_1-C_6)$haloalkyl$)$, or 1H-tetrazolyl.

6. The compound of claim 1, wherein $R^2$ and $R^3$ are each independently selected from the group consisting of H and aryl.

7. The compound of claim 1, wherein X is N; and Z is CH.

8. The compound of claim 1, wherein X is CH; and Z is N.

9. The compound of claim 1, wherein $R^8$ is selected from the group consisting of halo, $(C_1-C_6)$haloalkyl, and $(C_1-C_6)$alkyl.

10. The compound of claim 1, wherein m is 1.

11. The compound of claim 1, wherein $R^4$, $R^5$, $R^6$, and $R^7$ are each independently selected from the group consisting of H and $(C_1-C_6)$alkyl.

12. The compound of claim 1, wherein $R^9$ is selected from the group consisting of $(C_1-C_6)$alkyl, $(C_3-C_6)$cycloalkyl, and aryl$(C_1-C_6)$alkyl.

13. The compound of claim 1, wherein n is 0.

14. The compound of claim 1, represented by any one of the following structural formulae:

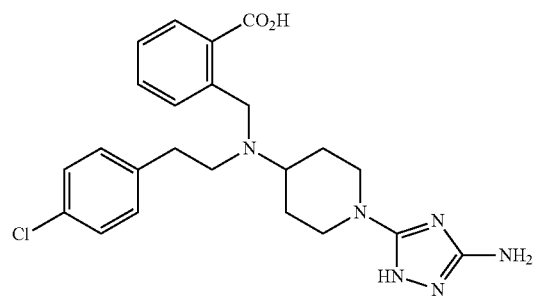

99
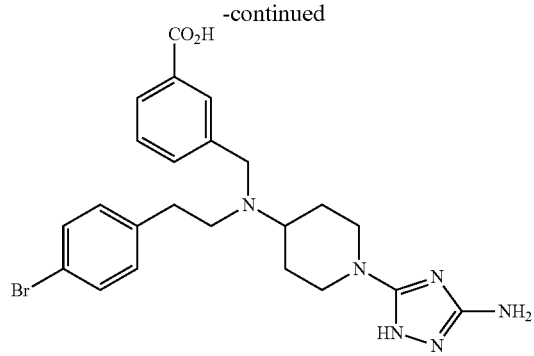
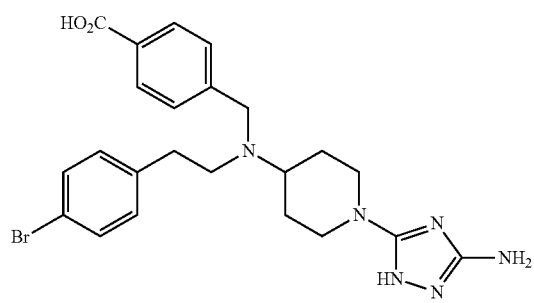
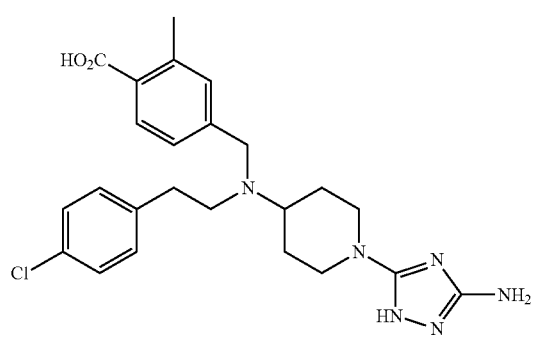
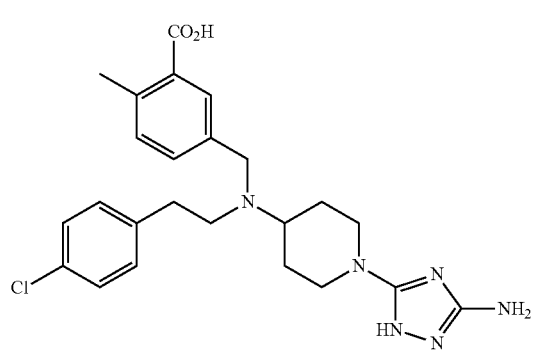
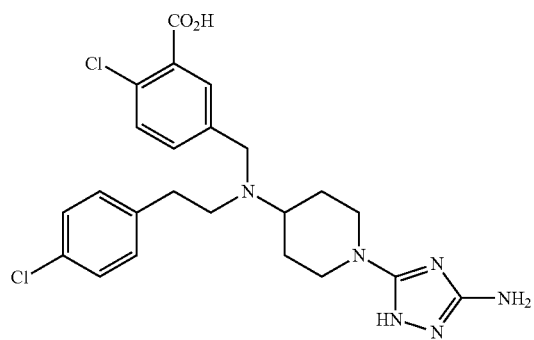
100
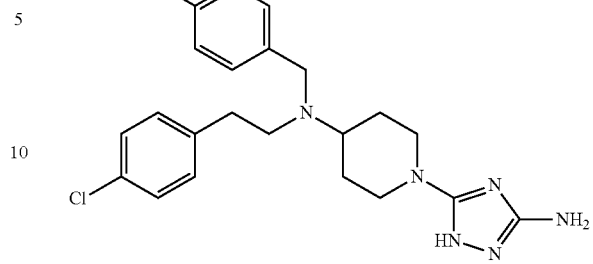
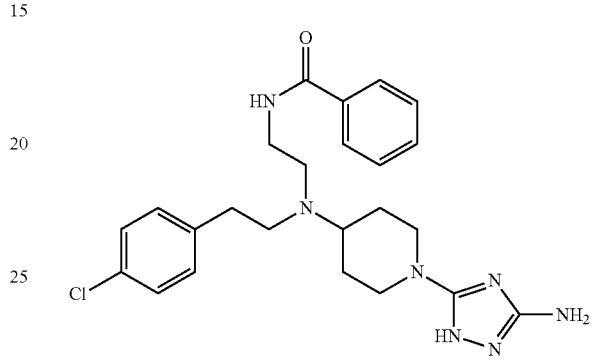
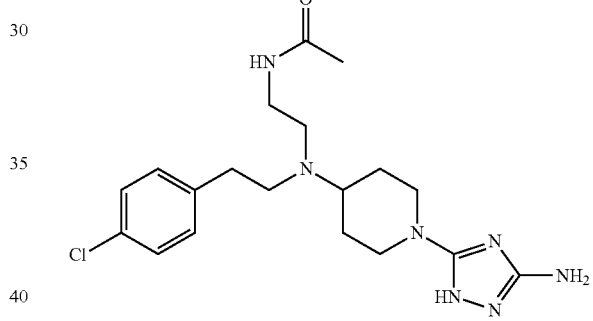
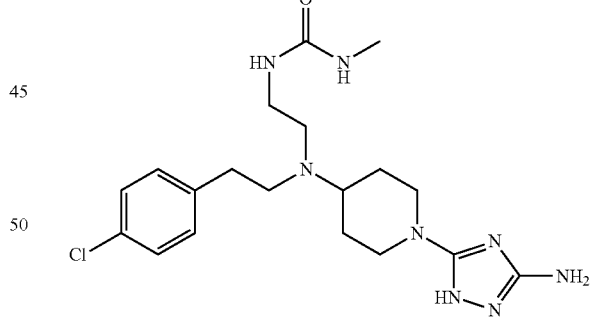
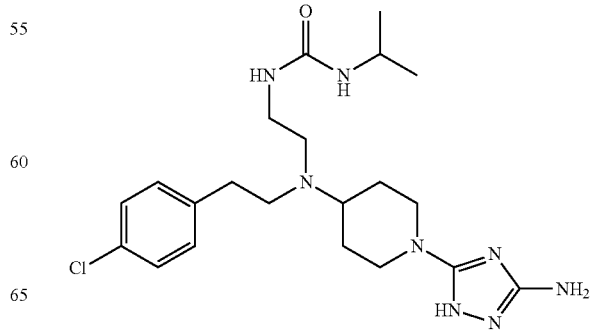

101
-continued
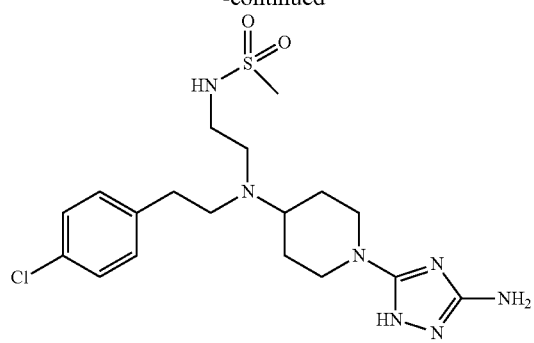
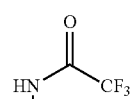
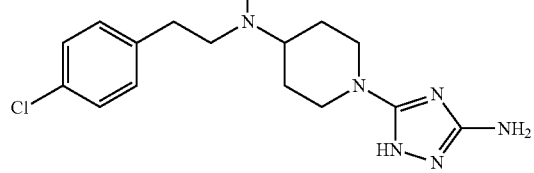
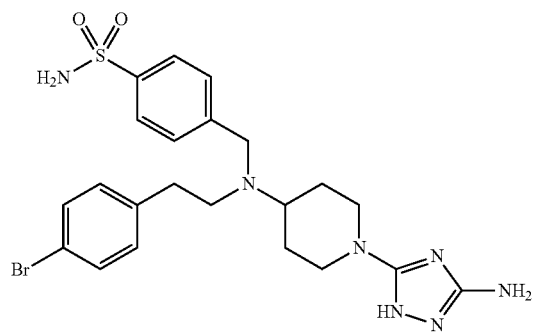
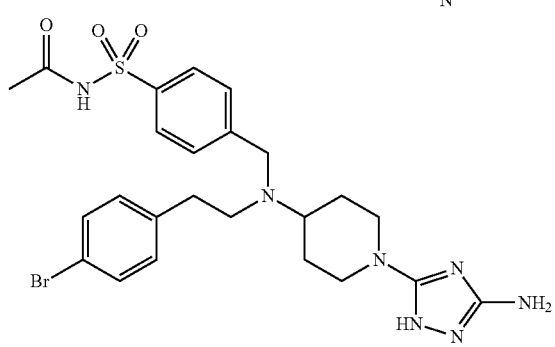
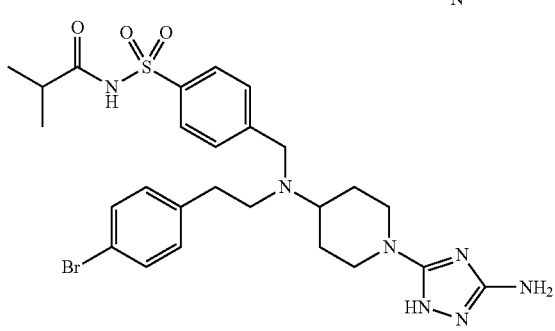
102
-continued
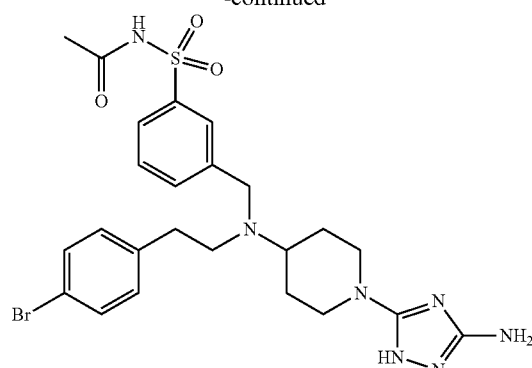
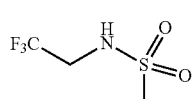
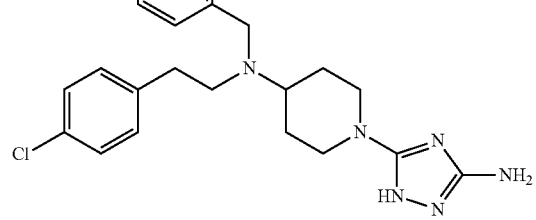
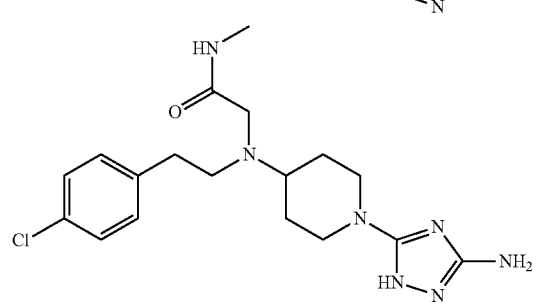
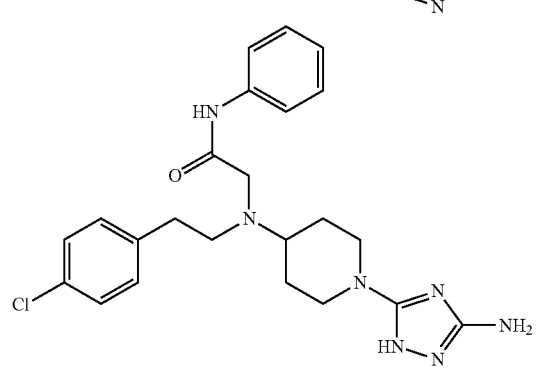
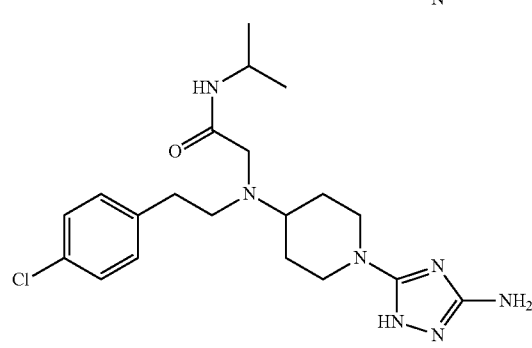

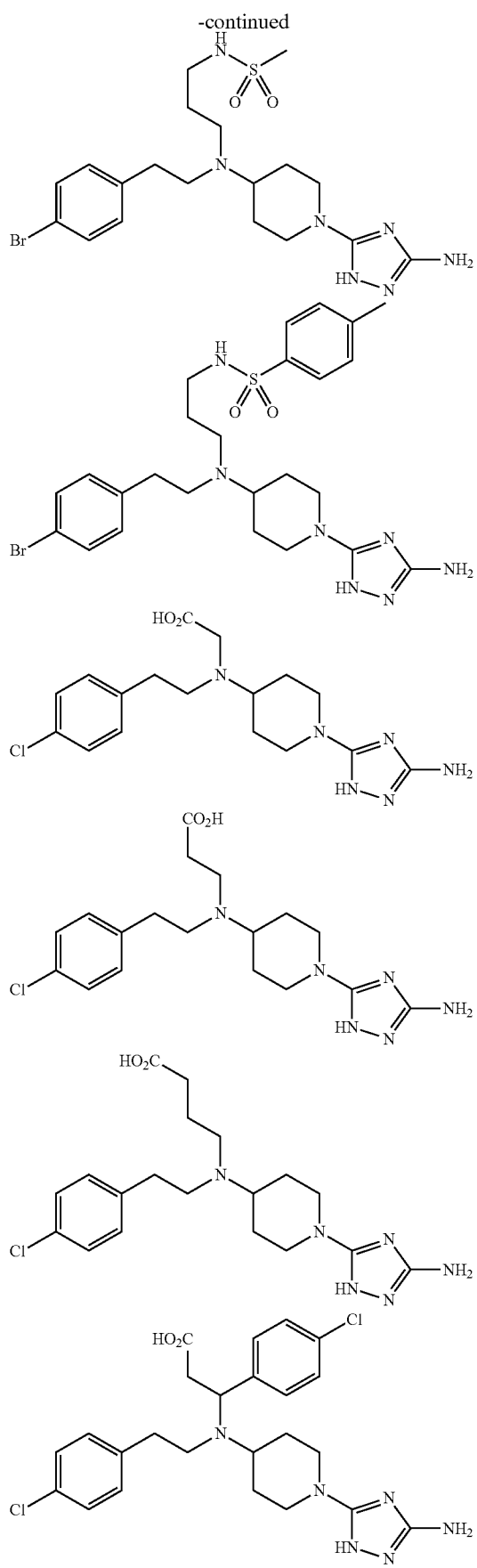
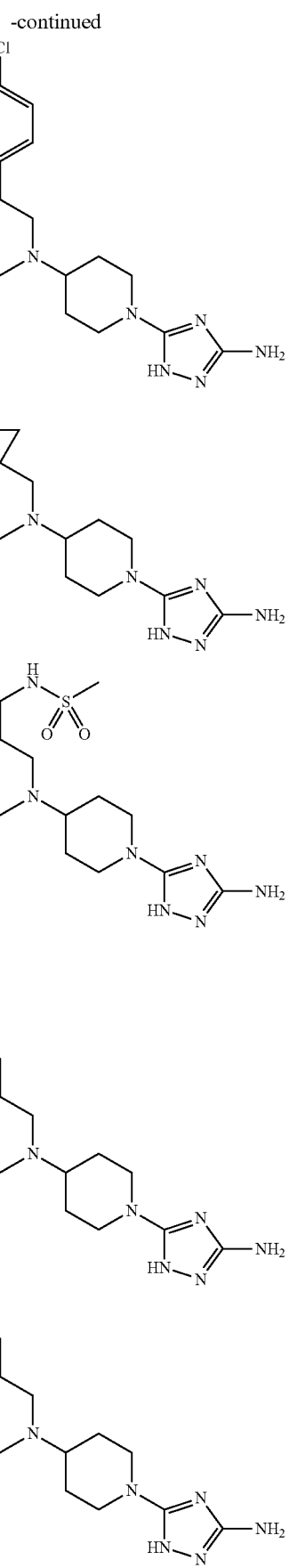

105
-continued
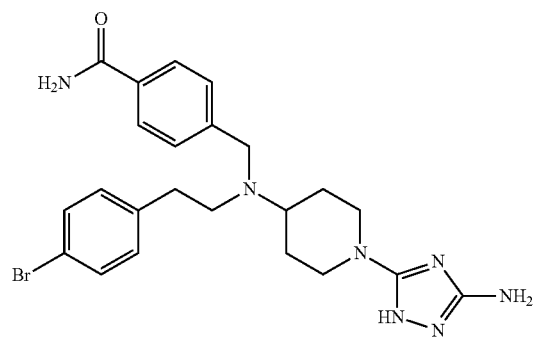
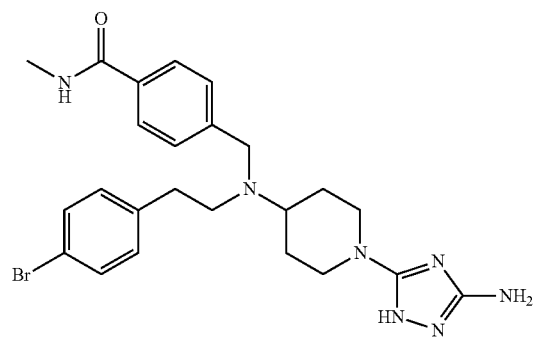
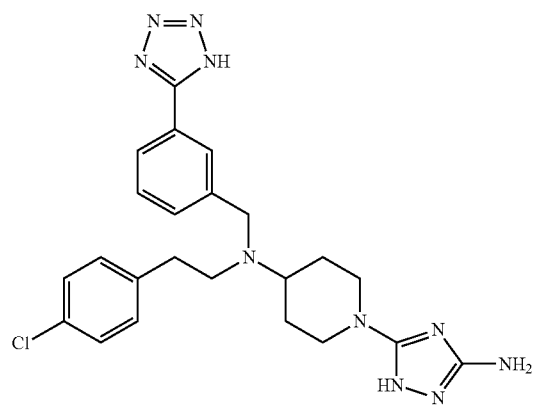
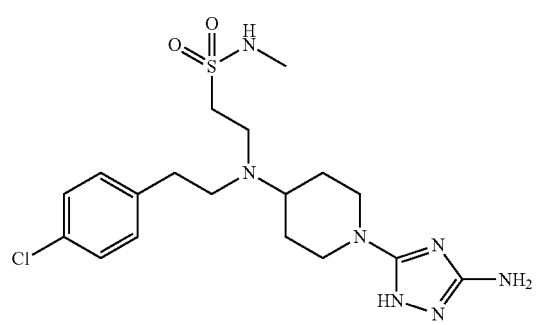
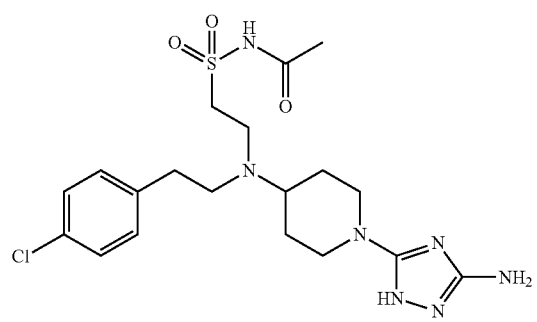
106
-continued
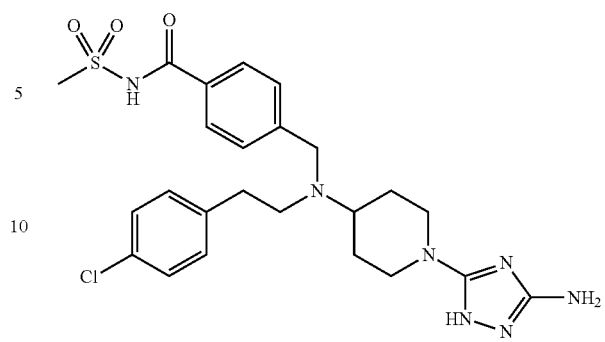
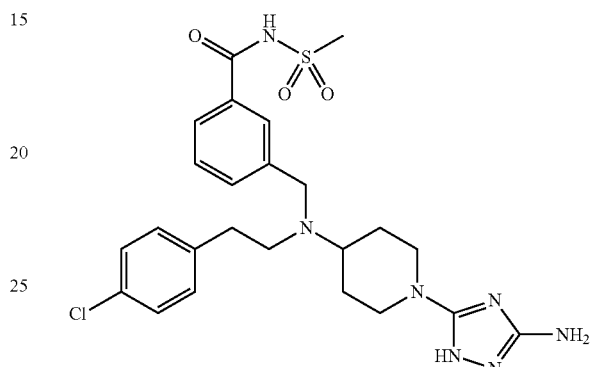
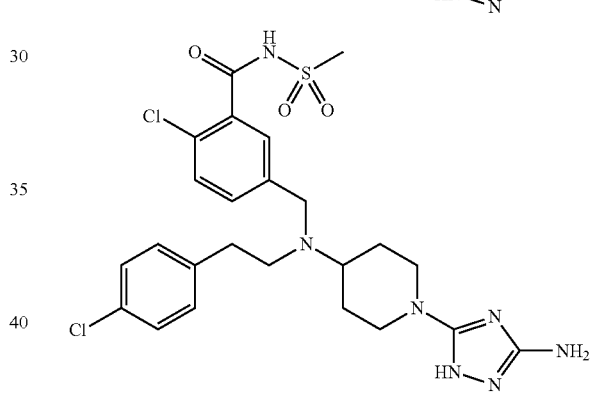
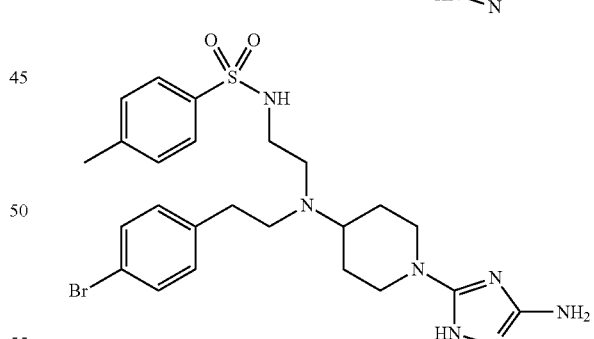
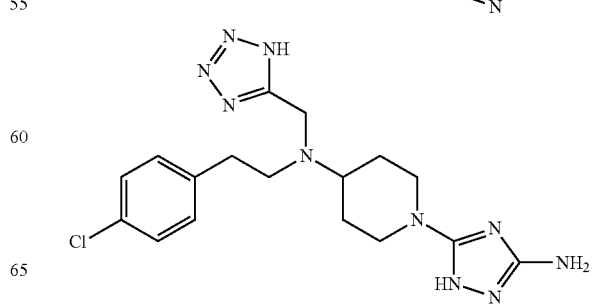

-continued

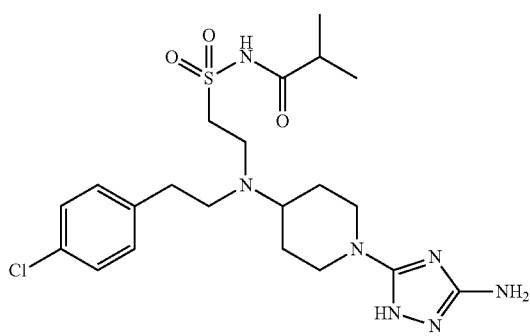

15. A compound represented by formula (II) or a pharmaceutically acceptable salt thereof:

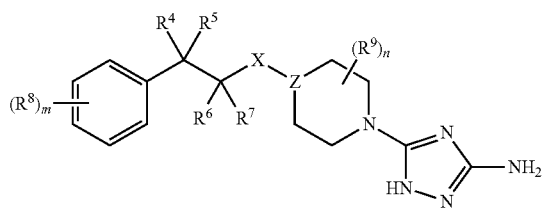

(II)

wherein:

X is NH or N(C(R$^1$)(R$^2$)(R$^3$)), and Z is CR$^{10}$; or X is CHR$^{11}$ or C(R$^{11}$)(C(R$^1$)(R$^2$)(R$^3$)), and Z is N;

R$^1$, R$^2$, R$^3$, R$^4$, R$^5$, R$^6$, and R$^7$ are each independently H, (C$_1$-C$_6$)alkyl, aryl(C$_1$-C$_6$)alkyl, or aryl; or R$^2$, taken together with R$^6$ or R$^7$, forms a 5- or 6-membered ring;

R$^8$ is selected from the group consisting of halo, (C$_1$-C$_6$)alkyl, (C$_1$-C$_6$)haloalkyl, and (C$_3$-C$_6$)cycloalkyl;

R$^9$ is selected from the group consisting of Y, aryl substituted by Y, and (C$_1$-C$_6$)alkyl substituted by Y;

Y is —CO$_2$H, —C(O)O(C$_1$-C$_6$)alkyl, —C(O)N(H)OH, —C(O)N(H)CN, —C(O)NH$_2$, —C(O)NH((C$_1$-C$_6$) alkyl), —C(O)N((C$_1$-C$_6$)alkyl)$_2$, —C(O)NH(aryl), —C(O)N(aryl)((C$_1$-C$_6$)alkyl), —C(O)N(aryl)$_2$, —C(O)NH((C$_1$-C$_6$)haloalkyl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)(C$_1$-C$_6$) alkyl, —S(O)$_2$NHC(O)(C$_1$-C$_6$)haloalkyl, —S(O)$_2$NHC(O)aryl, —N(H)S(O)$_2$(C$_1$-C$_6$)alkyl, —N(H)S(O)$_2$aryl, N(H)S(O)$_2$(C$_1$-C$_6$)haloalkyl, —NHC(O)((C$_1$-C$_6$)alkyl), —NHC(O)((C$_1$-C$_6$)haloalkyl), —NHC(O)(aryl), —NHC(O)NH(C$_1$-C$_6$) alkyl, —NHC(O)NHaryl, —C(O)N(H)S(O)$_2$(C$_1$-C$_6$) alkyl, —C(O)N(H)S(O)$_2$aryl, C(O)N(H)S(O)$_2$((C$_1$-C$_6$) haloalkyl), —P(O)(OH)$_2$,

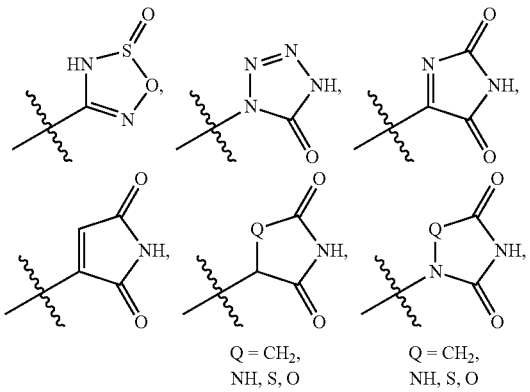

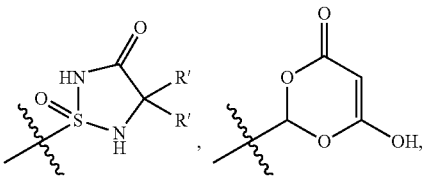

Q = CH$_2$, NH, S, O    Q = CH$_2$, NH, S, O

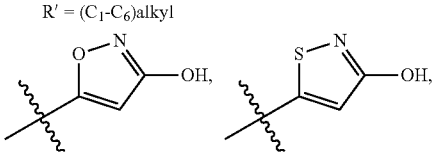

R' = (C$_1$-C$_6$)alkyl

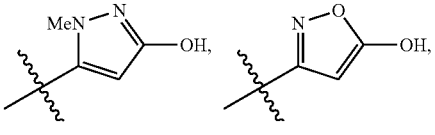

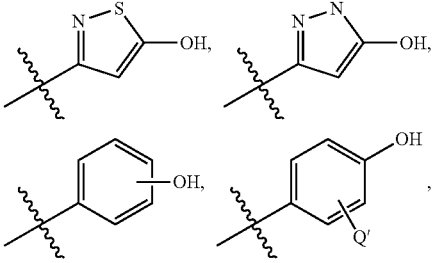

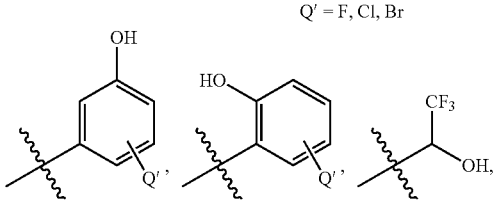

Q' = F, Cl, Br

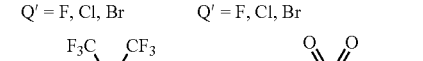

Q' = F, Cl, Br    Q' = F, Cl, Br

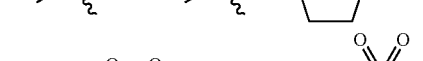

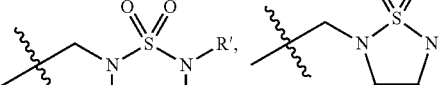

R' = (C$_1$-C$_6$)alkyl

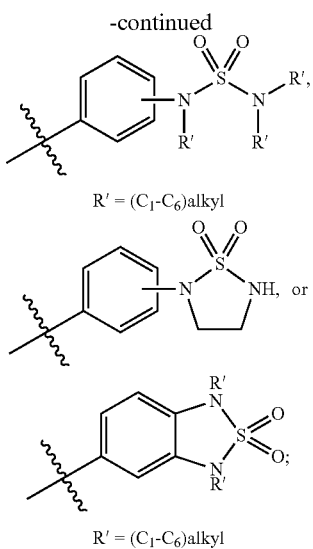

R' = (C₁-C₆)alkyl

R' = (C₁-C₆)alkyl

R$^{10}$ and R$^{11}$ are each independently selected from H and (C$_1$-C$_6$)alkyl;

m is an integer from 0-5;

n is 1 or 2;

further wherein any occurrence of (C$_1$-C$_6$)alkyl, aryl(C$_1$-C$_6$)alkyl, aryl, (C$_3$-C$_6$)cycloalkyl, (C$_1$-C$_6$)alkoxyl, (C$_1$-C$_6$)haloalkyl, (C$_1$-C$_6$)hydroxyalkyl, heteroaryl, or heteroaryl(C$_1$-C$_6$)alkyl is optionally and independently substituted by one or more substituents selected from the group consisting of halo, (C$_1$-C$_6$)alkyl, (C$_1$-C$_6$)haloalkyl, aryl, —NH$_2$, —NH((C$_1$-C$_6$)alkyl), —N((C$_1$-C$_6$)alkyl)$_2$, —OH, (C$_3$-C$_6$)cycloalkyl, (C$_1$-C$_6$)alkoxyl, (C$_1$-C$_6$)haloalkoxyl, —SH, —S((C$_1$-C$_6$)alkyl), (C$_1$-C$_6$)hydroxyalkyl, and (C$_1$-C$_6$)alkoxy(C$_1$-C$_6$)alkyl, —CN, —CF$_3$, —C(O)NH$_2$, —C(O)NH(R$^{12}$), —C(O)N(R$^{12}$)$_2$, —N(H)C(O)(R$^{12}$), —N(R$^{12}$)C(O)(R$^{12}$), —S(O)$_2$NH$_2$, —S(O)$_2$NH(R$^{12}$), —S(O)$_2$N(R$^{12}$)$_2$, —N(H)S(O)$_2$(R$^{12}$), —N(R$^{12}$)S(O)$_2$(R$^{12}$), —NHC(O)NH$_2$, —NHC(O)NH(R$^{12}$), and —NHC(O)N(R$^{12}$)$_2$; and each occurrence of R$^{12}$ is independently selected from the group consisting of (C$_1$-C$_6$)alkyl), aryl, and aryl(C$_1$-C$_6$)alkyl.

16. The compound of claim 15, wherein R$^9$ is Y.

17. The compound of claim 15, wherein R$^9$ is aryl substituted by Y.

18. The compound of claim 15, wherein R$^9$ is (C$_1$-C$_6$)alkyl substituted by Y.

19. The compound of claim 15, wherein Y is —CO$_2$H, —C(O)NH$_2$, —C(O)NH(C$_1$-C$_6$)alkyl, —C(O)N((C$_1$-C$_6$)alkyl)$_2$, —C(O)NH(aryl), C(O)N(aryl)((C$_1$-C$_6$)alkyl), C(O)N(aryl)$_2$, —C(O)NH((C$_1$-C$_6$)haloalkyl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)(C$_1$-C$_6$)alkyl, —S(O)$_2$NHC(O)(C$_1$-C$_6$)haloalkyl, —S(O)$_2$NHC(O)aryl, —N(H)S(O)$_2$(C$_1$-C$_6$)alkyl, —N(H)S(O)$_2$aryl, —N(H)S(O)$_2$(C$_1$-C$_6$)haloalkyl, —NHC(O)((C$_1$-C$_6$)alkyl), —NHC(O)((C$_1$-C$_6$)haloalkyl), —NHC(O)(aryl), —NHC(O)NH(C$_1$-C$_6$)alkyl, —NHC(O)NHaryl, —C(O)N(H)S(O)$_2$(C$_1$-C$_6$)alkyl, —C(O)N(H)S(O)$_2$aryl, C(O)N(H)S(O)$_2$((C$_1$-C$_6$)haloalkyl), or 1H-tetrazolyl.

20. A compound represented by formula (III) or a pharmaceutically acceptable salt thereof:

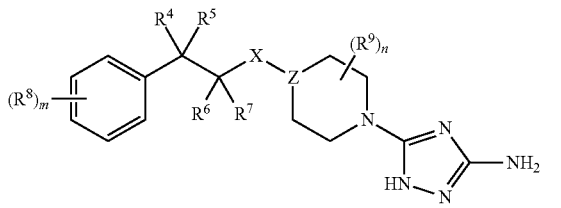

(III)

wherein:
X is NH or N(C(R$^1$)(R$^2$)(R$^3$)), and Z is CR$^{11}$); or X is CHR$^{11}$ or C(R$^{11}$)(C(R$^1$)(R$^2$)(R$^3$)), and Z is N;

R$^1$, R$^2$, R$^3$, R$^4$, R$^5$, and R$^7$ are each independently H, (C$_1$-C$_6$)alkyl, aryl(C$_1$-C$_6$)alkyl, or aryl; or R$^1$ or R$^2$, taken together with or R$^7$, forms a 5- or 6-membered ring;

R$^6$ is selected from the group consisting of Y, aryl substituted by Y, and (C$_1$-C$_6$)alkyl substituted by Y;

Y is —CO$_2$H, —C(O)O(C$_1$-C$_6$)alkyl, —C(O)N(H)OH, —C(O)N(H)CN, —C(O)NH$_2$, —C(O)NH((C$_1$-C$_6$)alkyl), —C(O)N((C$_1$-C$_6$)alkyl)$_2$, —C(O)NH(aryl), —C(O)N(aryl)((C$_1$-C$_6$)alkyl), —C(O)N(aryl)$_2$, —C(O)NH((C$_1$-C$_6$)haloalkyl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)(C$_1$-C$_6$)alkyl, —S(O)$_2$NHC(O)(C$_1$-C$_6$)haloalkyl, —S(O)$_2$NHC(O)aryl, —N(H)S(O)$_2$(C$_1$-C$_6$)alkyl, —N(H)S(O)$_2$aryl, N(H)S(O)$_2$(C$_1$-C$_6$)haloalkyl, —NHC(O)((C$_1$-C$_6$)alkyl), —NHC(O)((C$_1$-C$_6$)haloalkyl), —NHC(O)(aryl), —NHC(O)NH(C$_1$-C$_6$)alkyl, —NHC(O)NHaryl, —C(O)N(H)S(O)$_2$(C$_1$-C$_6$)alkyl, —C(O)N(H)S(O)$_2$aryl, C(O)N(H)S(O)$_2$((C$_1$-C$_6$)haloalkyl), —P(O)(OH)$_2$,

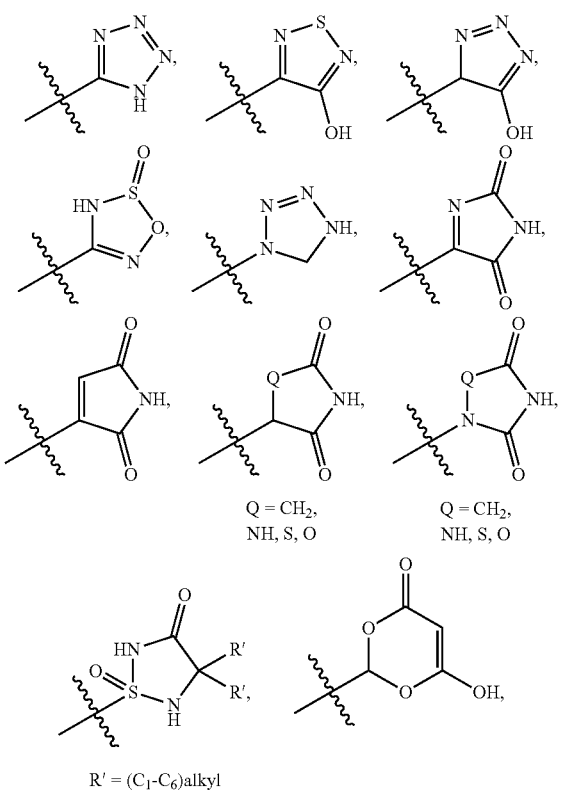

Q = CH$_2$, NH, S, O

Q = CH$_2$, NH, S, O

R' = (C$_1$-C$_6$)alkyl

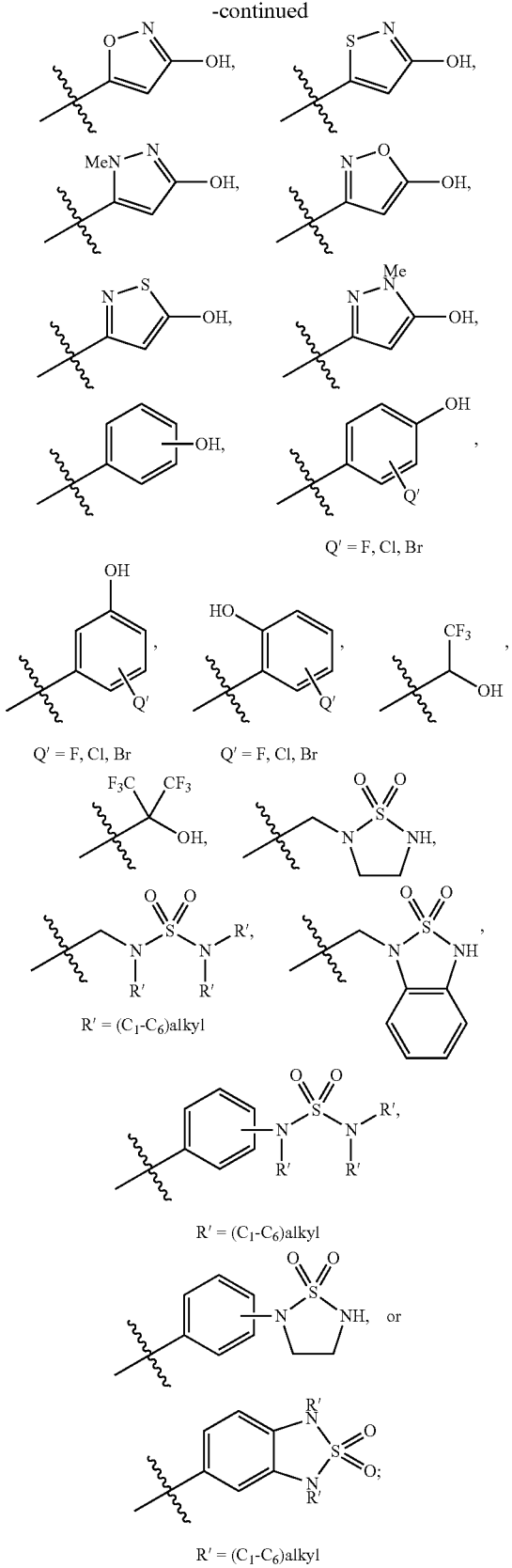

$R^8$ is selected from the group consisting of halo, $(C_1-C_6)$ alkyl, $(C_1-C_6)$haloalkyl, and $(C_3-C_6)$cycloalkyl;

$R^9$ is selected from the group consisting of OH, $(C_1-C_6)$ alkyl, $(C_3-C_6)$cycloalkyl, aryl$(C_1-C_6)$alkyl, aryl, $(C_1-C_6)$alkoxyl, $(C_1-C_6)$haloalkyl, $(C_1-C_6)$hydroxyalkyl, heteroaryl, and heteroaryl$(C_1-C_6)$alkyl;

$R^{10}$ and $R^{11}$ are each independently selected from H and $(C_1-C_6)$alkyl;

m is an integer from 0-5;

n is an integer from 0-2;

further wherein any occurrence of $(C_1-C_6)$alkyl, aryl$(C_1-C_6)$alkyl, aryl, $(C_3-C_6)$cycloalkyl, $(C_1-C_6)$alkoxyl, $(C_1-C_6)$haloalkyl, $(C_1-C_6)$hydroxyalkyl, heteroaryl, or heteroaryl$(C_1-C_6)$alkyl is optionally and independently substituted by one or more substituents selected from the group consisting of halo, $(C_1-C_6)$alkyl, $(C_1-C_6)$haloalkyl, aryl, —NH$_2$, —NH(($C_1-C_6$)alkyl), —N(($C_1-C_6$)alkyl)$_2$, —OH, $(C_3-C_6)$cycloalkyl, $(C_1-C_6)$alkoxyl, $(C_1-C_6)$haloalkoxyl, —SH, —S(($C_1-C_6$)alkyl), $(C_1-C_6)$hydroxyalkyl, and $(C_1-C_6)$alkoxy$(C_1-C_6)$alkyl, —CN, —CF$_3$, —C(O)NH$_2$, —C(O)NH(R$^{12}$), —C(O)N(R$^{12}$)$_2$, —N(H)C(O)(R$^{12}$), —N(R$^{12}$)C(O)(R$^{12}$), —S(O)$_2$NH$_2$, —S(O)$_2$NH(R$^{12}$), —S(O)$_2$N(R$^{12}$)$_2$, —N(H)S(O)$_2$(R$^{12}$), —N(R$^{12}$)S(O)$_2$(R$^{12}$), —NHC(O)NH$_2$, —NHC(O)NH(R$^{12}$), and —NHC(O)N(R$^{12}$)$_2$; and each occurrence of $R^{12}$ is independently selected from the group consisting of $(C_1-C_6)$alkyl), aryl, and aryl$(C_1-C_6)$alkyl.

21. The compound of claim 20, wherein $R^6$ is Y.

22. The compound of claim 20, wherein $R^6$ is aryl substituted by Y.

23. The compound of claim 20, wherein $R^6$ is $(C_1-C_6)$ alkyl substituted by Y.

24. The compound of claim 20, wherein Y is —CO$_2$H, —C(O)NH$_2$, —C(O)NH$(C_1-C_6)$alkyl, —C(O)N(($C_1-C_6$) alkyl)$_2$, —C(O)NH(aryl), C(O)N(aryl)(($C_1-C_6$)alkyl), C(O)N(aryl)$_2$, —C(O)NH(($C_1-C_6$)haloalkyl), —S(O)$_2$NH$_2$, —S(O)$_2$NH(($C_1-C_6$)alkyl), —S(O)$_2$NH(($C_1-C_6$)haloalkyl), —S(O)$_2$NH(aryl), —S(O)$_2$NHC(O)($C_1-C_6$)alkyl, —S(O)$_2$NHC(O)($C_1-C_6$)haloalkyl, —S(O)$_2$NHC(O)aryl, —N(H)S(O)$_2$($C_1-C_6$)alkyl, —N(H)S(O)$_2$aryl, —N(H)S(O)$_2$($C_1-C_6$)haloalkyl, —NHC(O)(($C_1-C_6$)alkyl), —NHC(O)(($C_1-C_6$)haloalkyl), —NHC(O)(aryl), —NHC(O)NH($C_1-C_6$)alkyl, —NHC(O)NHaryl, —C(O)N(H)S(O)$_2$($C_1-C_6$)alkyl, —C(O)N(H)S(O)$_2$aryl, C(O)N(H)S(O)$_2$(($C_1-C_6$)haloalkyl), or 1H-tetrazolyl.

25. A pharmaceutical composition, comprising a compound of claim 1; and a pharmaceutically acceptable carrier.

26. A pharmaceutical composition, comprising a compound of claim 15; and a pharmaceutically acceptable carrier.

27. A pharmaceutical composition, comprising a compound of claim 20; and a pharmaceutically acceptable carrier.

28. A method for treating asthma, comprising administering to a subject in need thereof a therapeutically effective amount of a compound of claim 1.

29. A method for treating a reaction caused by an allergen, comprising administering to a subject in need thereof a therapeutically effective amount of a compound of claim 1.

30. A method for treating asthma, comprising administering to a subject in need thereof a therapeutically effective amount of a compound of claim 15.

31. A method for treating a reaction caused by an allergen, comprising administering to a subject in need thereof a therapeutically effective amount of a compound of claim 15.

32. A method for treating asthma, comprising administering to a subject in need thereof a therapeutically effective amount of a compound of claim 20.

33. A method for treating a reaction caused by an allergen, comprising administering to a subject in need thereof a therapeutically effective amount of a compound of claim 20.

\* \* \* \* \*